United States Patent
Greene et al.

(10) Patent No.: US 12,282,028 B2
(45) Date of Patent: *Apr. 22, 2025

(54) ATOMIC DESCRIPTION OF IMMUNE COMPLEX THAT CAUSES HEPARIN-INDUCED THROMBOCYTOPENIA

(71) Applicant: The Trustees of the University of Pennsylvania, Philadelphia, PA (US)

(72) Inventors: Mark I. Greene, Penn Valley, PA (US); Douglas B. Cines, Wynnewood, PA (US); Zheng Cai, Wynnewood, PA (US); Zhiqiang Zhu, Philadelphia, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/420,177

(22) Filed: Jan. 23, 2024

(65) Prior Publication Data

US 2024/0241132 A1 Jul. 18, 2024

Related U.S. Application Data

(63) Continuation of application No. 17/929,524, filed on Sep. 2, 2022, now Pat. No. 11,913,963, which is a continuation of application No. 16/446,902, filed on Jun. 20, 2019, now Pat. No. 11,435,362, which is a continuation of application No. 15/524,511, filed as application No. PCT/US2015/059283 on Nov. 5, 2015, now Pat. No. 10,371,705.

(60) Provisional application No. 62/221,485, filed on Sep. 21, 2015, provisional application No. 62/076,213, filed on Nov. 6, 2014.

(51) Int. Cl.
| | |
|---|---|
| *G01N 33/577* | (2006.01) |
| *A61K 38/19* | (2006.01) |
| *A61K 39/395* | (2006.01) |
| *C07K 14/52* | (2006.01) |
| *C07K 16/18* | (2006.01) |
| *C07K 16/24* | (2006.01) |
| *G01N 33/53* | (2006.01) |
| *G01N 33/68* | (2006.01) |
| *G01N 33/86* | (2006.01) |
| *A61K 39/00* | (2006.01) |

(52) U.S. Cl.
CPC ....... *G01N 33/6863* (2013.01); *A61K 38/195* (2013.01); *A61K 39/3955* (2013.01); *C07K 14/522* (2013.01); *C07K 16/24* (2013.01); *G01N 33/86* (2013.01); *A61K 2039/505* (2013.01); *G01N 2333/522* (2013.01); *G01N 2400/40* (2013.01); *G01N 2800/222* (2013.01); *G01N 2800/50* (2013.01); *G01N 2800/52* (2013.01)

(58) Field of Classification Search
CPC .............. G01N 33/6863; G01N 33/86; G01N 2333/522; G01N 2400/40; G01N 2800/222; G01N 2800/50; G01N 2800/52; A61K 38/195; A61K 39/3955; A61K 2039/505; C07K 14/522; C07K 16/24

See application file for complete search history.

(56) References Cited

U.S. PATENT DOCUMENTS

| | | | |
|---|---|---|---|
| 4,816,567 | A | 3/1989 | Cabilly et al. |
| 5,225,539 | A | 7/1993 | Winter |
| 5,585,089 | A | 12/1996 | Queen et al. |
| 5,693,761 | A | 12/1997 | Queen et al. |
| 5,693,762 | A | 12/1997 | Queen et al. |
| 5,739,103 | A | 4/1998 | Rollins et al. |
| 5,859,205 | A | 1/1999 | Adair et al. |
| 5,939,598 | A | 8/1999 | Kucherlapati et al. |
| 10,371,705 | B2 | 8/2019 | Greene et al. |
| 11,435,362 | B2 | 9/2022 | Greene et al. |
| 2006/0040323 | A1 | 2/2006 | Arepally et al. |

FOREIGN PATENT DOCUMENTS

CA    2204731 A1    7/1996

OTHER PUBLICATIONS

Presta, "Antibody engineering," Current Opinion in Structural Biology, 1992, vol. 2, No. 4, pp. 593-596.
Rauova et al., "Monocytebound PF4 In The Pathogenesis Of Heparin-Induced Thrombocytopenia", Blood, 2010, vol. 116, pp. 5021-5031.
Rauova et al., "Role Of Platelet Surface PF4 Antigenic Complexes In Heparin-Induced Thrombocytopenia Pathogenesis: Diagnostic And Therapeutic Implications", Blood, 2006, vol. 107, pp. 2346-2353.
Rauova et al., "Ultralarge complexes of PF4 and heparin are central to the pathogenesis of heparin-induced thrombocytopenia", Blood, 2005, vol. 105, pp. 131-138.

(Continued)

*Primary Examiner* — Julie Ha
*Assistant Examiner* — Kristina M Hellman
(74) *Attorney, Agent, or Firm* — BakerHostetler

(57) ABSTRACT

The present invention provides a mutant protein which has the same amino acid sequence of a wild type PF4 monomer except that (i) at least one amino acid of the wild type PF4 monomer has been deleted, (ii) at least one amino acid of the wild type PF4 monomer has been replaced by another amino acid, or (iii) a combination of such changes has been made. The present invention also provides methods of treating or reducing the likelihood of HIT, treating angiogenesis, treating abnormal cell growth, or affecting coagulation pathologies that lead to thrombus formation, by administering such mutant proteins to a patient.

5 Claims, 26 Drawing Sheets
Specification includes a Sequence Listing.

(56) References Cited

OTHER PUBLICATIONS

Reilly et al., "Heparin-Induced Thrombocytopenia/Thrombosis In A Transgenic Mouse Model Requires Human Platelet Factor 4 And Platelet Activation Through FcgammaRIIA", Blood, 2001, vol. 98, pp. 2442-2447.
Riechmann et al., "Reshaping human antibodies for therapy", Nature, 1988, vol. 332, pp. 323-327.
Rota et al., "Fondaparinux-Related Thrombocytopenia In A Previous Low-Molecular-Weight Heparin (LMWH)-Induced Heparin-Induced Thrombocytopenia (HIT)", Thromb Haemost, 2008, vol. 99, pp. 779-781.
Sachais et al., "Dynamic antibody-binding properties in the pathogenesis of HIT", Blood, 2012, vol. 120, pp. 1137-1142.
Sachais et al., "Rational Design And Characterization Of Platelet Factor 4 Antagonists For The Study Of Heparin-Induced Thrombocytopenia", Blood, 2012, vol. 119, pp. 5955-5962.
Schroder et al., Superresolution Biomolecular Crystallography With Low-Resolution Data, Nature, 2010, vol. 464, pp. 1218-1222.
Strog et al., "Toward The Structural Genomics Of Complexes: Crystal Structure Of A PE/PPE Protein Complex From *Mycobacterium tuberculosis*", Proc Natl Acad Sci USA, 2006, vol. 103, No. 21, pp. 8060-8065.
Stuckey et al., "A Model Of The Platelet Factor 4 Complex With Heparin", Proteins, 1992, vol. 14, pp. 277-287.
Turpie et al., "Postoperative Fondaparinux Versus Postoperative Enoxaparin For Prevention Of Venous Thromboembolism After Elective Hip-Replacement Surgery: A Randomised Double-Blind Trial", Lancet, 2002, vol. 359, pp. 1721-1726.
UnitProt Accession No. P02776, accessed at URL www.uniprot.org/uniprot/P02776, Apr. 10, 2021 (Year: 2021).
Vagin et al., "Molecular replacement with MOLREP", Acta Crystallogr D Biol Crystallogr, 2010, vol. 66, pp. 22-25.
Visentin et al., "Heparin Is Not Required For Detection Of Antibodies Associated With Heparin-Induced Thrombocytopenia/Thrombosis", J Lab Clin Med, 2001, vol. 138, pp. 22-31.
Warkentin et al., "Anti-Platelet Factor 4/Heparin Antibodies In Orthopedic Surgery Patients Receiving Antithrombotic Prophylaxis With Fondaparinux Or Enoxaparina", Blood, 2005, vol. 106, pp. 3791-3796.
Warkentin et al., "Can Heparin-Induced Thrombocytopenia Be Associated With Fondaparinux Use? Reply To A Rebuttal", J Thromb Haemost, 2008, vol. 6, pp. 1243-1246.
Warkentin et al., "Heparininduced Thrombocytopenia Associated With Fondaparinux", N Engl J Med, 2007, vol. 356, pp. 2653-2655.
Winn et al., "Overview Of The CCP4 Suite And Current Developments", Acta Crystallogr D Biol Crystallogr, 2011, vol. 67, pp. 235-242.
Xiao et al., "Immune Complexes Formed Following The Binding Of Anti-Platelet Factor 4 (CXCL4)", Blood, 2008, vol. 112, pp. 1091-1100.
Xiao et al., "Supplemental Materials and Methods", Blood, 2008, vol. 112, pp. S1-S3.
Zhang et al., "Crystal Structure Of Recombinant Human Platelet Factor4", Biochemistry, 1994, vol. 33, pp. 8361-8366.
Ziporen et al., "Defining An Antigenic Epitope On Platelet Factor 4 Associated With Heparin-Induced Thrombocytopenia", Blood, 1998, vol. 92, pp. 3250-3259.
U.S. Appl. No. 17/929,524, filed Sep. 2, 2022.
U.S. Appl. No. 16/446,902, filed Jun. 20, 2019.
U.S. Appl. No. 15/524,511, filed May 4, 2017.
Afonine et al., "Towards Automated Crystallographic Structure Refinement With Phenix.Refine", Acta Crystallogr D Biol Crystallogr, 2012, vol. 68, pp. 352-367.
Amiral et al., "Antibodies To Macromolecular Platelet Factor 4-Heparin Complexes In Heparin-Induced Thrombocytopenia: A Study Of 44 Cases", Thromb Haemost, 1995, vol. 73, pp. 21-28.
Arepally et al., "Characterization Of A Murine Monoclonal Antibody That Mimics Heparin-Induced Thrombocytopenia Antibodies", Blood, 2000, vol. 95, pp. 1533-1540.
Baker et al., "Electrostatics Of Nanosystems: Application To Microtubules And The Ribosome", Proc Natl Acad Sci USA, 2001, vol. 98, pp. 10037-10041.
Bauer et al., "Fondaparinux Compared With Enoxaparin For The Prevention Of Venous Thromboembolism After Elective Major Knee Surgery", N Engl J Med, 2001, vol. 345, pp. 1305-1310.
Bhatt et al., "Fondaparinux-Associated Heparin-Induced Thrombocytopenia", Eur J Haematol, 2013, vol. 91, pp. 437-441.
Block et al., "Characterization Of Bonds Formed Between Platelet Factor 4 And Negatively Charged Drugs Using Single Molecule Force Spectroscopy", Soft Matter, 2014, vol. 10, pp. 2775-2784.
Brandt et al., "Characterisation Of The Conformational Changes In Platelet Factor 4 Induced By Polyanions: Towards In Vitro Prediction Of Antigenicity", Thromb Haemost, 2014, vol. 112, pp. 53-64.
Burch et al., "Fondaparinux-Associated Heparininduced Thrombocytopenia", Proc Bayl Univ Med Cent, 2012, vol. 25, pp. 13-15.
Chen et al., "Molprobity: All-Atom Structure Validation For Macromolecular Crystallography", Acta Crystallogr D. Biol Crystallogr, 2010, vol. 66, pp. 12-21.
Chothia et al., "Canonical Structures for the Hypervariable Regions of Immunoglobulins", J. Mol. Biol., 1987, vol. 196, pp. 901-917.
Clackson et al, "Making antibody fragments using phage display libraries", Nature, 1991, vol. 352, pp. 624-628.
Cole et al., Monoclonal Antibodies and Cancer Therapy, Alan R. Liss, Inc., 1985, pp. 77-96.
Cowan et al., "Binding Of Heparin To Human Platelet Factor 4", Biochem J., 1986, vol. 234, pp. 485-488.
Cuker et al., "How I Treat Heparin-Induced Thrombocytopenia", Blood, 2012, vol. 119, pp. 2209-2218.
Cuker et al., "Novel Diagnostic Assays For Heparin-Induced Thrombocytopenia", Blood, 2013, vol. 121, pp. 3727-3732.
Eisman et al., "Structural And Functional Comparison Of The Genes For Human Platelet Factor 4 And PF4," Blood, 1990, vol. 76, No. 2, pp. 336-344.
Eke et al., "Heparin-Induced Thrombocytopenia", Medscape, Ed. Emmanuel Besa, 2014, pp. 1-18, Available at: Ernedicine.Medscape.Com/Article/135784 6-Overview.
Emsley et al., "Features And Development Of Coot", Acta Crystallogr D Biol Crystallogr, 2010, vol. 66, pp. 486-501.
Falati et al., "Real-Time In Vivo Imaging Of Platelets, Tissue Factor And Fibrin During Arterial Thrombus Formation In The Mouse", Nat Med., 2002, vol. 8, pp. 1175-1181.
Funatsu et al., "Stimulation And Inhibition Of Angiogenesis In Diabetic Retinopathy", Jpn J Ophthalmol. 2001, vol. 45, No. 6, pp. 577-584.
Greinacher et al., "Characterization Of The Structural Requirements For A Carbohydrate Based Anticoagulant With A Reduced Risk Of Inducing The Immunological Type Of Heparin-Associated Thrombocytopenia", Thromb Haemost, 1995, vol. 74, pp. 886-892.
Greinacher et al., "Close Approximation of Two Platelet Factor 4 Tetramers by Charge Neutralization Forms the Antigens Recognized by HIT Antibodies", Arterioscler Thromb Vase Biol., 2006, vol. 26, pp. 2386-2393.
Gupta et al., "A Potent Inhibitor Of Endothelial Cell Proliferation Is Generated By Proteolytic Cleavage Of The Chemokine Platelet Factor 4," PNAS 1995, vol. 92, pp. 7799-7803.
Jones et al., "Replacing the complementarity determining regions in a human antibody with those from a mouse", Nature, 1986, vol. 321, pp. 522-525.
Kang et al., "Fondaparinux For The Treatment Of Suspected Heparin-Induced Thrombocytopenia: A Propensity Score-Matched Study", Blood, 2015, vol. 125, pp. 924-929.
Kohler et al., "Continuous cultures of fused cells secreting antibody of predefined specificity", Nature, 1975, vol. 256, No. 5517, pp. 495-497.
Kozbor et al., "The production of monoclonal antibodies from human lymphocytes", Immunology Today, 1983, vol. 4, No. 3, pp. 72-79.

(56) References Cited

OTHER PUBLICATIONS

Kreimann et al., "Binding Of Anti-Platelet Factor 4/Heparin Antibodies Depends On The Thermodynamics Of Conformational Changes In Platelet Factor 4", Blood, 2014, vol. 124, pp. 2442-2449.

Laskowski et al., "PROCHECK: a program to check the stereochemical quality of protein structures", J. Appl Cryst, 1993, vol. 26, pp. 283-291.

Lecomte et al., "New Insights Into the Negative Regulation of Hematopoiesis by Chemokine Platelet Factor 4 and Related Peptides," Blood, 1998, vol. 91, pp. 2772-2780.

Lee et al., "Heparin-Induced Thrombocytopenia", Hematology Am Soc Hematol Educ Program, 2013, vol. 2013, pp. 668-674.

Lewis et al., "Argatroban Anticoagulation In Patients With Heparin-Induced Thrombocytopenia", Arch Intern Med. 2003, vol. 163, pp. 1849-1856.

Li et al., "Defining A Second Epitope For Heparin-Induced Thrombocytopenia/Thrombosis Antibodies Using KKO, A Murine Hitlike Monoclonal Antibody", Blood, 2002, vol. 99, pp. 1230-1236.

Linkins et al., "Treatment And Prevention Of Heparin-Induced Thrombocytopenia: Antithrombotic Therapy And Prevention Of Thrombosis, 9th Ed: American College Of Chest Physicians Evidence-Based Clinical Practice Guidelines", Chest, 2012, vol. 141, pp. E495s-E530S.

Lippi et al., "Recombinant Platelet Factor 4: A Therapeutic, Antineoplastic Chimera?", Semin Thromb Hemost., 2010, vol. 36, No. 5, pp. 558-569. Doi: 10.1055/S-0030-1255450. Epub Jul. 14, 2010.

Liu et al., "Identification Of Critical Amino Acids In Human Platelet Factor 4 (PF4) Required For Its Modulatory Effects On CD4+CD 25+ Regulatory T Cells," Blood, 2004, vol. 104, Issue. 11, pp. 3.

Lu et al., "A New Method For Coarse-Grained Elastic Normal-Mode Analysis", J Chem Theory Compu, 2006, vol. 2, pp. 464-471.

Maione et al., "Inhibition Of Angiogenesis By Recombinant Human Platelet Factor-4 And Related Peptides", Science, Jan. 1990, vol. 247, No. 4938, pp. 77-79, DOI: 10.1126/science.1688470.

Marks et al., "By-passing Immunization Human Antibodies from V-gene Libraries Displayed on Phage", J. Mol. Biol., 1991, vol. 222, pp. 581-597.

Mayo et al., "Human Platelet Factor 4 Monomerdimertetramer Equilibria Investigated By 1H NMR Spectroscopy", Biochemistry, 1989, vol. 28, pp. 9469-9478.

Mayo et al., "Heparin Binding To Platelet Factor-4. An NMR And Sitedirected Mutagenesis Study: Arginine Residues Are Crucial For Binding", Biochem J, 1995, vol. 312, pp. 357-365.

Mayo et al., "NMR Solution Structure Of The 32-Kda Platelet Factor 4 ELR-Motif N-Terminal Chimera: A Symmetric Tetramer", Biochemistry, 1995, vol. 34, pp. 11399-11409.

McCoy et al., "Phaser Crystallographic Software", J Appl Crystallogr, 2007, vol. 40, pp. 658-674.

Murshudov et al., "Refinement of macromolecular structures by the maximum-likelihood method", Acta Crystallogr D Biol Crystallogr, 1997, vol. 53, pp. 240-255.

Murshudov et al., "REFMAC5 for the refinement of macromolecular crystal structures", Acta Crystallogr D Biol Crystallogr, 2011, vol. 67, pp. 355-367.

Nesmelova et al., "CXC and CC chemokines form mixed heterodimers: association free energies from molecular dynamics simulations and experimental correlations", J Biol Chem, 2008, vol. 283, pp. 24155-24166.

Nguyen et al., "Quantitative Description Of Thermodynamic And Kinetic Properties Of The Platelet Factor 4/Heparin Bonds", Nanoscale, 2015, vol. 7, pp. 10130-10139.

Otwinowski et al., "Processing Of X-Ray Diffraction Data Collected In Oscillation Mode", Methods In Enzymology, 1997, vol. 276, pp. 307-326.

Phillips et al., "Considerations In Using Anticoagulant Therapy In Special Patient Populations", Am J Health Syst Pharm, 2008, vol. 65, pp. S13-S21.

```
hPF4    EAEEDGDLQCLCVKTTSQ-VRPRHITSLEVIKAGPHCPTAQLIATLKNGRKICLDLQAPL  59
mPF4    PEESDGDISCVCVKTISSGIHLKHITSLEVIKAGRHCAVPQLIATLKNGRKICLDRQAPL  60
        *.****.*;****  *. ;; ;********* ...*********** ** hPF4    YKRIIKKLLES  70
mPF4    YKKVIKKILES  71
        **;;***;***
```

FIG. 6

FIG. 7A

Light Chain RTO-Fab:
ELDIELTQSPKSMSMSVGERVTLTC KASENVVTYVS WYQQKPEQSPKLLIY GASNRYT G
VPDRFTGSGSATDFTLTISSVQAEDLADYHC GQGYSYPYT PGGGTKLEIKRADAAPTVS
IFPPSSEQLTSGGASVVCFLNNFYPKDINVKWKIDGSERQNGVLNSWTDQDSKDSTYSM
SSTLTLTKDEYERHNSYTCEATHKTSTSPIVKSFNRNEC*

Heavy Chain RTO-Fab:
SLEVQLVESGGGLVKPGGSLKLSCAAS GFAFSRYDMS WVRQTPEKRLEWVA TITSGDNY
YYPDSVKG RFTISRDNARNTLYLQMSRLRSEDTALYYCTR QGLLYYAMDY WGQGTSVN
VFSAKTTPPSVYPLAPGCGDTTGSSVTLGCLVKGYFPESVTVTWNSGSLSSSVHTFPAL
LQSGLYTMSSSVTVPSSTWPSQTVTCSVAHPASSTTVDKKLEPSGPISTINPCPPCKEC
HKCPAPNLEGGPSVFIFPPNIKDVLMISLTPKVTCVVVDVSEDDPDVQISWFVNNVEVH
TAQTQTHREDYNSTIRVVSTLPIQHQDWMSGKEFKCKVNNKDLPSPIERTISKIKGLVR
APQVYILPPPAEQLSRKDVSLTCLVVGFNPGDISVEWTSNGHTEENYKDTAPVLDSDGS
YFIYSKLNMKTSKWEKTDSFSCNVRHEGLKNYYLKKTISRSPGK RTO CDRs
CDR-L1:  KASENVVTYVS
CDR-L2:  GASNRYT
CDR-L3:  GQGYSYPYT

CDR-H1:  GFAFSRYDMS
CDR-H2:  TITSGDNYTYYPDSVKG
CDR-H3:  QGLLYYAMDY

FIG. 7B

RTO epitopes on PF4 (underlined sequence, also shown in the structure below)

```
 4  6   11   16   21   26   31   36   41   46   51   56   61   66
EDGDLQCLCVKTTSQVRPRHITSLEVIKAGPHCPTAQLIATLKNGRKICLDLQAPLYKKIIKKLL
```

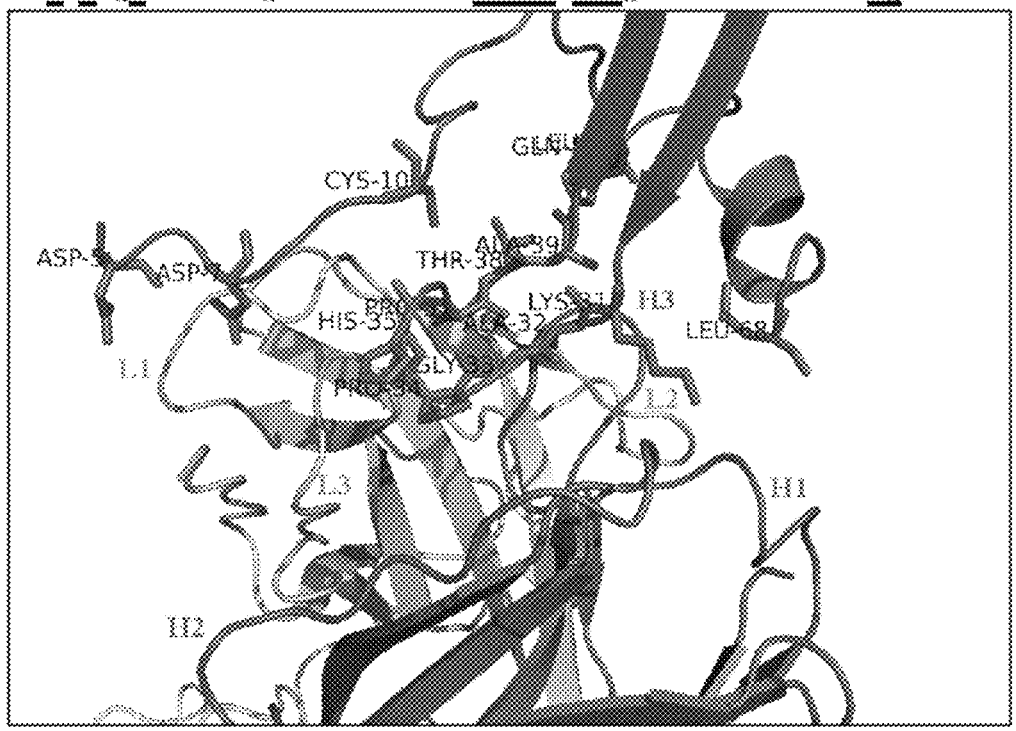

FIG. 8

Humanized RTO (huRTO) sequences

| | |
|---|---|
| huRTO-H | EVQLVESGGGLVQPGGSLRLSCAASGFAFSRYDMSWVRQAPGKGLEWVATITSGDNYT |
| huRTO-H | YYPDSVKGRFTISRDNSKNTLYLQMNSLRAEDTAVYYCTRQGLLYYAMDYWGQGTLVT |
| huRTO-H | VSSASTKGPSVFPLAPSSKSTSGGTAALGCLVKDYFPEPVTVSWNSGALTSGVHTFPAVL |
| huRTO-H | QSSGLYSLSSVVTVPSSSLGTQTYICNVNHKPSNTKVDKKVEPK |
| huRTO-L | DIQMTQSPSSLSASVGDRVTITCKASENVVTYVSWYQQKPGKAPKLLIYGASNRYTGV |
| huRTO-L | PSRFSGSGSGTDFTLTISSLQPEDFATYYCGQGYSYPYTFGQGTKVEIKRTVAAPSVFIF |
| huRTO-L | PPSDEQLKSGTASVVCLLNNFYPREAKVQWKVDNALQSGNSQESVTEQDSKDSTYSLSST |
| huRTO-L | LTLSKADYEKHKVYACEVTHQGLSSPVTKSFNRGEC |

Underline: CDRs

FIG. 10B
```
A/6   11   16   21   26   31   36   41   46   51   56   61   66
      GDLQCLCVKTTSQVRPRHITSLEVIKAGPHCPTAQLIATLKNGRKICLDLQAPLYKKIIKKLLES
B/6   11   16   21   26   31   36   41   46   51   56   61   66
      GDLQCLCVKTTSQVRPRHITSLEVIKAGPHCPTAQLIATLKNGRKICLDLQAPLYKKIIKKLLES
C/6   11   16   21   26   31   36   41   46   51   56   61   66
      GDLQCLCVKTTSQVRPRHITSLEVIKAGPHCPTAQLIATLKNGRKICLDLQAPLYKKIIKKLLES
D/6   11   16   21   26   31   36   41   46   51   56   61   66
      GDLQCLCVKTTSQVRPRHITSLEVIKAGPHCPTAQLIATLKNGRKICLDLQAPLYKKIIKKLLES
```
FIG. 10C
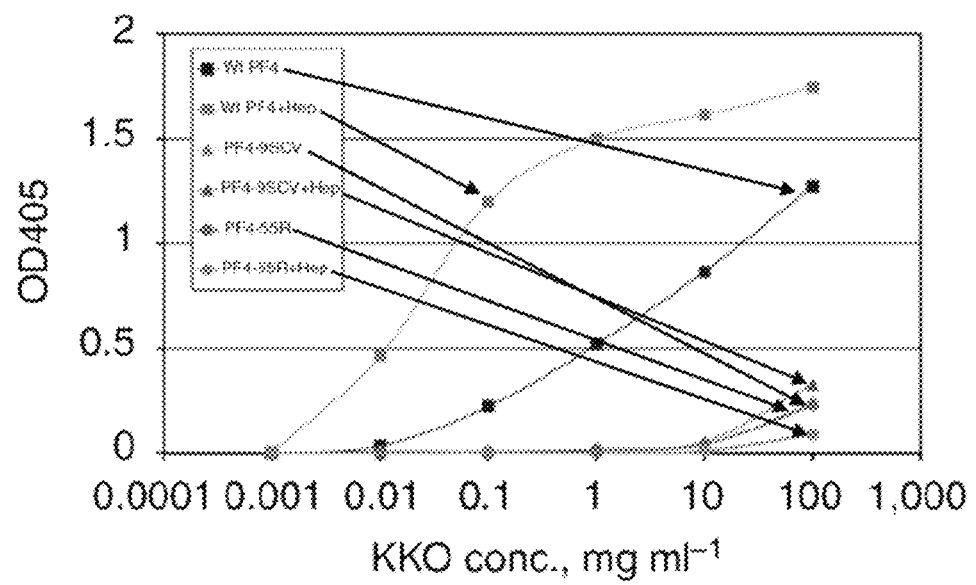
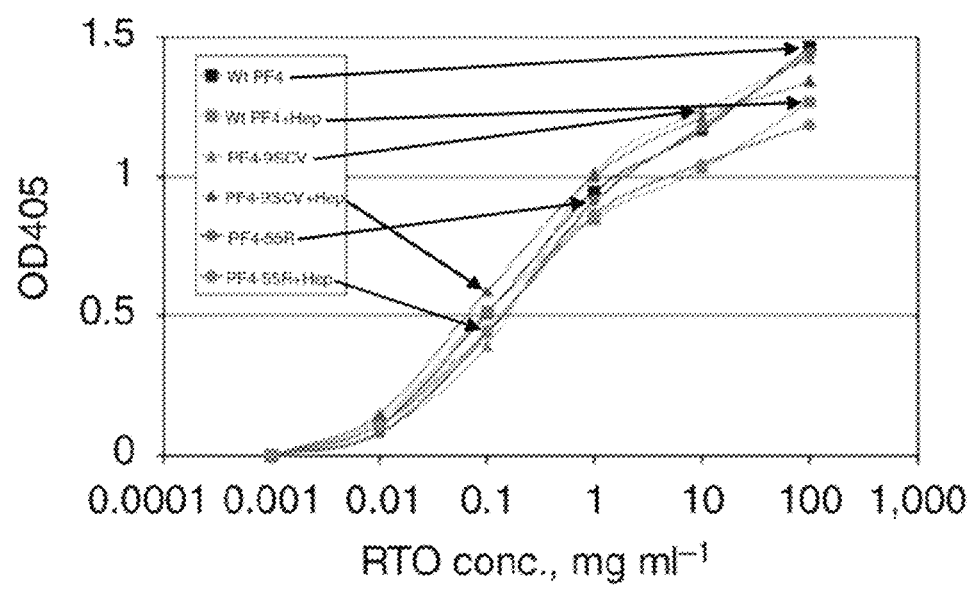

```
 4 6    11   16   21   26   31   36   41   46   51   56   61   66
EDGDLQCLCVKTTSQVRPRHITSLEVIKAGPHCPTAQLIATLKNGRKICLDLQAPLYKKIIKKLL
```

```
PF4-wt      EAEEDGDLQCLCVKTTSQVRPRHITSLEVIKAGPHCPTAQLIATLKNGRKICLDLQAPLY 60
PF4-del8aa  --------QCLCVKTTSQVRPRHITSLEVIKAGPHCPTAQLIATLKNGRKICLDLQAPLY 52
                    ****************************************************

PF4-wt      KKIIKKLLES 70
PF4-del8aa  KKIIKKLLES 62
            **********
```

PF4-wt, tetramer | PF4-del8aa, monomer

ATOMIC DESCRIPTION OF IMMUNE COMPLEX THAT CAUSES HEPARIN-INDUCED THROMBOCYTOPENIA

CROSS-REFERENCE TO RELATED APPLICATIONS

This application is a continuation of U.S. patent application Ser. No. 17/929,524 filed Sep. 2, 2022, which is a continuation of U.S. application Ser. No. 16/446,902 filed Jun. 20, 2019, now U.S. Pat. No. 11,435,362, which is a continuation of U.S. patent application Ser. No. 15/524,511 filed May 4, 2017, now U.S. Pat. No. 10,371,705, which is the National Stage Application of International Patent Application No. PCT/US2015/059283, filed Nov. 5, 2015, which claims the priority of U.S. Provisional Application No. 62/221,485, filed on Sep. 21, 2015, and U.S. Provisional Application No. 62/076,213, filed Nov. 6, 2014, the contents of each of which are hereby incorporated by reference in their entirety.

GOVERNMENT RIGHTS

This invention was made with government support under HL110860 awarded by the National Institutes of Health. The government has certain rights in the invention.

SEQUENCE LISTING

The instant application contains a Sequence Listing XML, which has been submitted electronically as an XML formatted sequence listing with a file name "103241_007028_SL.xml" and a creation date of Jan. 20, 2024, and having a size of 26,499 bites. The sequence listing submitted electronically is part of the specification and is herein incorporated by reference in its entirety.

Throughout this application, various publications are referenced, including referenced in parenthesis. Full citations for publications referenced in parenthesis may be found listed at the end of the specification immediately preceding the claims. The disclosures of all referenced publications in their entireties are hereby incorporated by reference into this application in order to more fully describe the state of the art to which this invention pertains.

BACKGROUND OF INVENTION

Heparin is a commonly used anti-coagulant. It prevents the formation of new blood clots and stops the enlargement of existing clots. Heparin can sometimes bind to and form a complex with platelet factor 4 (PF4), a protein made by platelets (cell fragments that aggregate to form blood clots). Roughly 12 million patients are exposed to heparin annually (Sankar Eke 2014) and up to 1% of these patients will develop heparin-induced thrombocytopenia (HIT), a life-threatening complication where patients make antibodies that bind to the heparin/PF4 complex. These antibodies trigger the activation and aggregation of platelets, resulting in blood clots ("thrombosis") and the depletion of platelets ("thrombocytopenia").

HIT leads to longer hospital stays and increased morbidity and mortality, resulting in significant additional treatment costs. For example, among US medical patients who developed HIT, hospital costs were reported to be higher by an average of ~$41,000 compared to patients without HIT (Udeh et al. (2013) Heparin-induced thrombocytopenia: a clinical and economic review. *OA Anaesthetics* 1(1):3). Healthcare institutions and insurance companies incur additional costs when HIT is falsely diagnosed, as these misdiagnosed patients are given unnecessary anti-coagulants (which can be more expensive and which can increase the risk of bleeding, leading to subsequent complications).

Typically management of HIT consists of stopping the heparin and using an alternative anti-coagulant. These alternative drugs are often inhibitors of thrombin, a protein that promotes coagulation. Two direct thrombin inhibitors are available in the United States: lepirudin and argatroban.

There is a need for novel compounds, compositions, and methods for diagnosing, monitoring, and treating HIT.

SUMMARY OF THE INVENTION

The present invention provides a humanized antibody or antibody fragment comprising
 (a) a humanized light chain comprising
  1) Complementarity Determining Region (CDR)-L1, the sequence of which is identical to the sequence of SEQ ID NO: 3 (KASENVVTYVS);
  2) CDR-L2, the sequence of which is identical to the sequence of SEQ ID NO: 4 (GASNRYT); and
  3) CDR-L3, the sequence of which is identical to the sequence of SEQ ID NO: 5 (GQGYSYPYT), and
 (b) a humanized heavy chain comprising
  1) CDR-H1, the sequence of which is identical to the sequence of SEQ ID NO: 6 (GFAFSRYDMS);
  2) CDR-H2, the sequence of which is identical to the sequence of SEQ ID NO: 7 (TITSGDNYTYYPDSVKG); and
  3) CDR-H3, the sequence of which is identical to the sequence of SEQ ID NO: 8 (QGLLYYAMDY).

Aspects of the present invention relate to a vector encoding a humanized antibody or antibody fragment described herein, or a heavy chain or light chain of a humanized antibody or antibody fragment of the invention.

The present invention also provides a cell or virus comprising the vector of the invention, wherein if the cell is a human cell, then the cell is a cultured human cell.

The present invention also provides a method for diagnosing heparin-induced thrombocytopenia (HIT) in a subject, comprising
 i) obtaining a plasma or serum sample from the subject;
 ii) determining the ratio of
  (1) the reactivity of antibodies in the sample to wild-type PF4, to
  (2) the reactivity of antibodies in the sample to a mutant PF4 monomer that remains in a monomeric state; and
 iii) diagnosing the subject as having HIT based on the ratio of (1) to (2).

The present invention also provides a method for determining whether a subject receiving the administration of heparin or a heparin-mimic is at risk of becoming afflicted with heparin-induced thrombocytopenia (HIT), comprising
 i) obtaining a plasma or serum sample from the subject;
 ii) determining the ratio of
  (1) the reactivity of antibodies in the sample to wild-type PF4, to
  (2) the reactivity of antibodies in the sample to a mutant PF4 monomer that remains in a monomeric state; and
 iii) identifying the subject as at risk of becoming afflicted with HIT based on the ratio of (1) to (2).

The present invention also provides a method for monitoring the progression of heparin-induced thrombocytopenia (HIT) in a subject, comprising
  i) obtaining a first plasma or serum sample from the subject;
  ii) obtaining a second plasma or serum sample from the subject;
  iii) determining in each of the first and second samples of the subject the ratio of
    (1) the reactivity of antibodies in the sample to wild-type PF4, to
    (2) the reactivity of antibodies in the sample to a mutant PF4 monomer that remains in a monomeric state; and
  iv) determining that HIT has progressed in the subject if the ratio of (1) to (2) is higher in the second sample than in the first sample, and determining that the HIT has not progressed in the subject if the ratio of (1) to (2) is lower in the second sample than in the first sample or if the ratio of (1) to (2) is the same in the first and second samples.

Aspects of the present invention relate to a method for treating a subject afflicted with heparin-induced thrombocytopenia (HIT) comprising administering to the subject an effective amount of an antibody or antibody fragment that is capable of binding at least a portion of the same epitope as the epitope to which RTO binds so as to reduce platelet factor 4 (PF4) oligomerization.

The present invention also provides a method for reducing the likelihood that a subject receiving the administration of heparin or a heparin-mimic will become afflicted with heparin-induced thrombocytopenia (HIT) comprising administering to the subject an effective amount of an antibody or antibody fragment that is capable of binding at least a portion of the same epitope as the epitope to which RTO binds so as to reduce platelet factor 4 (PF4) oligomerization.

The present invention also provides a method for assessing the antigenicity of an anionic anticoagulant comprising
  i) obtaining a plasma or serum sample from a subject who has received administration of the anionic anticoagulant;
  ii) determining the ratio of
    (1) the reactivity of antibodies in the sample to wild-type PF4, to
    (2) the reactivity of antibodies in the sample to a mutant PF4 monomer that remains in a monomeric state; and
  iii) assessing the antigenicity of the anionic anticoagulant based on the ratio of (1) to (2).

Aspects of the present invention relate to a method for assessing whether an anionic anticoagulant is capable of causing heparin-induced thrombocytopenia (HIT) comprising
  i) obtaining a plasma or serum sample from a subject who has received administration of the anionic anticoagulant;
  ii) determining the ratio of
    (1) the reactivity of antibodies in the sample to wild-type PF4, to
    (2) the reactivity of antibodies in the sample to a mutant PF4 monomer that remains in a monomeric state; and
  iii) assessing whether the anionic anticoagulant is capable of causing HIT based on the ratio of (1) to (2).

The present invention also provides a mutant platelet factor 4 (PF4) monomer which has the same amino acid sequence of a wild type PF4 monomer except that
  (i) at least one amino acid of the wild type PF4 monomer has been deleted,
  (ii) at least one amino acid of the wild type PF4 monomer has been replaced by another amino acid, or
  (iii) a combination of such changes has been made.

The present invention also provides a method for treating a subject afflicted with heparin-induced thrombocytopenia (HIT), treating angiogenesis, treating abnormal cell growth, or affecting coagulation pathologies that lead to thrombus formation, comprising administering to the subject an effective amount of a mutant platelet factor 4 (PF4) monomer so as to interfere with PF4 tetramer oligomerization.

The present invention also provides a method for reducing the likelihood that a subject receiving the administration of heparin or a heparin-mimic will become afflicted with heparin-induced thrombocytopenia (HIT) comprising administering to the subject an effective amount of a mutant platelet factor 4 (PF4) monomer so as to interfere with PF4 tetramer oligomerization.

BRIEF DESCRIPTION OF THE DRAWINGS

FIG. 1A—The 2Fo-Fc electron density map (at 1.4a contour level) fitted with a fondaparinux in the PF4/fondaparinux complex. FIG. 1B—the 2Fo-Fc OMIT electron density in the fondaparinux binding site, contoured at 1.4σ. The positions of the ordered sulfate groups are confirmed by the anomalous signals of sulfur.

FIG. 6. Comparison of the RTO epitope on a PF4 monomer and the KKO epitope on a PF4 tetramer. Arrows on the bottom denote overlapping sites of interactions on PF4. The RTO epitope on PF4 (SEQ ID NO: 10) overlaps with the KKO epitope (SEQ ID NO: 9), especially within the A32-A39 loop.

FIG. 7A and FIG. 7B. RTO Sequences and Epitopes. FIG. 7A—RTO Sequences (Light Chain RTO-Fab, SEQ ID NO: 1; Heavy Chain RTO-Fab, SEQ ID NO: 2; CDR-L1, SEQ ID NO: 3; CDR-L2, SEQ ID NO: 4; CDR-L3, SEQ ID NO: 5; CDR-H1, SEQ ID NO: 6; CDR-H2, SEQ ID NO: 7; CDR-H3, SEQ ID NO: 8). FIG. 7B RTO binding to PF4 (SEQ ID NO: 10).

FIG. 8. Humanized RTO (huRTO) sequences. huRTO-L (SEQ ID NO: 13) and huRTO-H (SEQ ID NO: 14).

FIG. 9A—Overall structure of the PF4/pentasaccharide complex. Fondaparinux makes contacts with a single PF4 tetramer in the groove among the monomers on one side of the asymmetric tetramer. Monomers A, B, C and D in one PF4 tetramer are indicated. FIG. 9B—Fondaparinux (stick representations) stabilizes the PF4 tetramer by binding in the groove among 3 monomers in a PF4 tetramer. Dotted line indicates the polar interactions between Fondaparinux and three PF4 monomers. FIG. 9C—One fondaparinux (spheres) denoted in the smaller box binds in the groove of one tetramer (cartoon representation on the left), and also binds to the C-terminal helix of a second tetramer (cartoon representation on the right), thereby bridging PF4 tetramers. FIG. 9D—Electrostatic potential surface representation of the PF4 tetramer shows that fondaparinux binds along a continuous positively charged surface on the "closed" side of PF4 tetramer. FIG. 9E—Detailed representation of the positively charged residues (labeled) on the fondaparinux binding interface between two PF4 tetramers. FIG. 9F—Analysis of crystal lattice reveals a molecular pathway of the formation of antigenic complexes. A fragment of heparin first binds within the groove of one PF4 tetramer (left); binding of the first PF4 tetramer imparts a local linearized structure on heparin, which enhances the binding of a second tetramer (middle); progression of this process eventuates in the formation of ultralarge antigenic complexes (right).

FIG. 10A, FIG. 10B, FIG. 10C, FIG. 10D, and FIG. 10E. Crystal structure of PF4/KKO-Fab complex. FIG. 10A—Overall structure of the PF4/KKO-Fab complex (upper panel: cartoon representations of the complex; lower panel: molecular surface representations). The heavy chain and light chain of KKO-Fab are depicted. FIG. 10B—Detailed binding interface of HIT antibody KKO to a PF4 tetramer. Residues within a PF4 tetramer that are less than 5 Å away from KKO-Fab molecule are underlined. PF4 monomers are labeled (i.e. Chain A, B, C, D) as in FIG. 9A. The sequence shown is SEQ ID NO: 9. FIG. 10C—Binding of KKO and RTO to structure-based PF4 mutants. FIG. 10D—Platelet aggregation by wild-type PF4 and PF4 mutants. KKO induced platelet aggregation in the presence of wild-type PF4 and heparin whereas an isotype matched non-pathogenic antibody RTO described below did not. The panel also demonstrates that PF4 mutants bearing mutations along the KKO binding interface were unable to mediate KKO-induced platelet aggregation. FIG. 10E—Model of the KKO-Fab/PF4/heparin ternary complex. Surface representations of KKO-Fab are depicted. The model assumes the heparin molecule is composed of about 7 structures similar to fondaparinux depicted in the figure as a non-continuous chain. Intact UFH may further enhance the stability of the holo complex compared with the fondaparinux fragment, thereby rendering it more antigenic and more capable of binding multiple IgG antibodies.

FIG. 11A—Overall structure of the PF4/RTO-Fab complex (left panel: cartoon representations of the complex; right panel: molecular surface representations). The heavy chain and light chain of RTO-Fab are depicted. FIG. 11B—Detailed binding interface of the non-HIT antibody RTO to a PF4 monomer. Residues of a PF4 monomer that are less than 5 Å away from RTO-Fab molecule are underlined. The sequence shown is SEQ ID NO: 10. FIG. 11C—Superposition of the PF4 monomer (on the left) in the RTO-Fab/PF4 complex with that in the unbound PF4 (on the right) indicates that binding of RTO-Fab causes a dramatic structural change in the PF4 monomer: the C-terminal helices are shifted ~60°. FIG. 11D—Superposition of the PF4 monomer (middle) in complex with RTO-Fab (labeled) with the unbound PF4 tetramer (right). The three arrows on the left of the diagram indicate the sites where binding of RTOFab (left) to one PF4 monomer causes steric clashes with a second PF4 monomer in the tetramer, thereby preventing tetramer formation.

FIG. 12A—Inhibition of KKO/PF4 mediated platelet activation by RTO. Samples of whole blood were incubated with the indicated concentrations of RTO in the presence of PF4 (10 µg/ml) for 15 min before adding the platelet-activating anti-PF4 antibody KKO or human IgG. Activation of platelets was followed by expression of P-selectin; the effect of RTO is expressed as % of geometric mean fluorescent intensity (MFI) of P-selectin expression on platelets relative to MFI in the absence of RTO. FIG. 12B—In vitro platelet activation assay demonstrated that preincubation of PF4 with RTO prevented KKO-induced platelet aggregation. FIG. 12C—Representative composite images of platelet fluorescence overlaid on brightfield snapshots of injuries in mice receiving either RTO or the IgGk2B isotype control TRA are shown. Pre KKO images show thrombi 15 minutes after initial injury and injection of RTO or TRA. Post KKO images represent the same thrombus 15 minutes after KKO had been injected intravenously. Arrows represent the direction of blood flow. FIG. 12D—Each dot denotes the percent change in the size of a single injury based on binding of fluorescently labeled platelets in mice receiving either RTO or the IgGK2B isotype control TRA followed by KKO. Error bars show the standard deviation. N=18 injuries in 3 mice for RTO, N=19 injuries in 3 mice for TRA. p<0.0001.

FIG. 14A—The protein sequence alignment of wild type PF4 (SEQ ID NO: 11) and Del 8AA mutant (SEQ ID NO: 16). FIG. 14B—structures of wild type PF4 (PDB id:1RHP, as tetramer) and Del 8AA mutant (modeled from RTOFab/PF4 monomer complex, PDB code 4RAU, as monomer) are shown.

DETAILED DESCRIPTION OF THE INVENTION

Figure 1A:
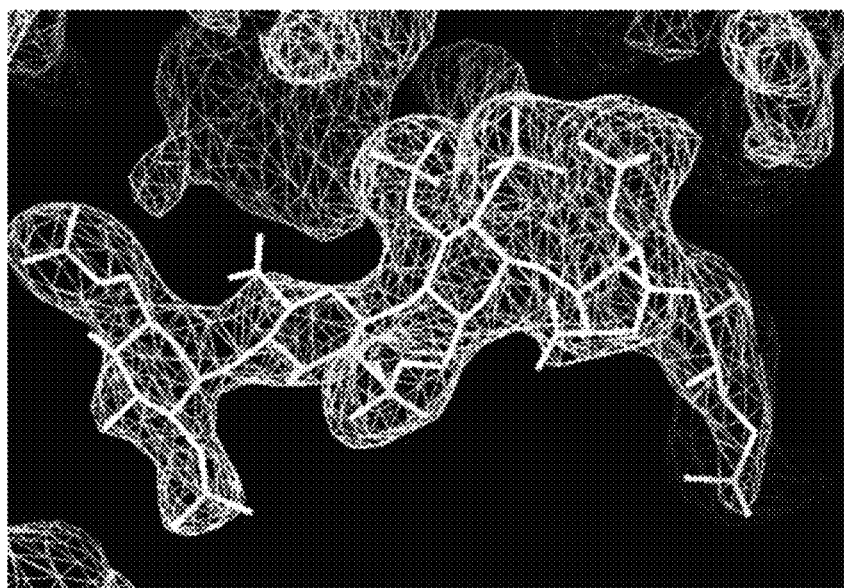
FIG. 1A and FIG. 1B. Well-defined fondaparinux electron density.

The present invention provides a humanized antibody or antibody fragment comprising
(a) a humanized light chain comprising
  1) Complementarity Determining Region (CDR)-L1, the sequence of which is identical to the sequence of SEQ ID NO: 3 (KASENVVTYVS);
  2) CDR-L2, the sequence of which is identical to the sequence of SEQ ID NO: 4 (GASNRYT); and
  3) CDR-L3, the sequence of which is identical to the sequence of SEQ ID NO: 5 (GQGYSYPYT), and
(b) a humanized heavy chain comprising
  1) CDR-H1, the sequence of which is identical to the sequence of SEQ ID NO: 6 (GFAFSRYDMS);
  2) CDR-H2, the sequence of which is identical to the sequence of SEQ ID NO: 7 (TITSGDNYTYYPDSVKG); and
  3) CDR-H3, the sequence of which is identical to the sequence of SEQ ID NO: 8 (QGLLYYAMDY).

In some embodiments, the humanized antibody or antibody fragment is capable of binding at least a portion of the same epitope as the epitope to which RTO binds so as to reduce platelet factor 4 (PF4) oligomerization.

In some embodiments, the humanized antibody or antibody fragment is capable of binding to a portion of the same epitope as the epitope to which RTO binds that overlaps with a portion of the same epitope as the epitope to which KKO binds.

In some embodiments, the humanized antibody or antibody fragment is capable of binding to the same epitope as the epitope to which RTO binds.

In some embodiments, the humanized antibody or antibody fragment is capable of reducing PF4 oligomerization.

In some embodiments, the oligomerization is dimerization or tetramerization.

In some embodiments, the humanized antibody or antibody fragment is capable of reducing the binding of KKO to PF4.

In some embodiments, the humanized antibody or antibody fragment is capable of binding between the PF4 AB dimer interface.

In some embodiments, the humanized antibody comprises a human IgG1, IgG2, IgG3, IgG4, IgM, IgE, or IgA heavy chain immunoglobulin constant domain.

In some embodiments, the fragment is a Fv, Fab, Fab', Fab'-SH, F(ab')$_2$ or a single-chain antibody molecule, or part of a diabody or a multispecific antibody formed from more than one antibody fragment.

In some embodiments, the humanized antibody or antibody fragment comprises
(a) a humanized light chain having amino acids in the sequence of SEQ ID NO: 13; and
(b) a humanized heavy chain having amino acids in the sequence of SEQ ID NO: 14.

In some embodiments, the humanized antibody or antibody fragment is an isolated humanized antibody or antibody fragment.

The present invention also provides a pharmaceutical composition comprising a humanized antibody or antibody fragment of the invention.

Aspects of the present invention relate to a vector encoding a humanized antibody or antibody fragment described herein, or a heavy chain or light chain of a humanized antibody or antibody fragment of the invention.

The present invention also provides a cell or virus comprising the vector of the invention, wherein if the cell is a human cell, then the cell is a cultured human cell.

The present invention also provides a method for diagnosing heparin-induced thrombocytopenia (HIT) in a subject, comprising
  i) obtaining a plasma or serum sample from the subject;
  ii) determining the ratio of
    (1) the reactivity of antibodies in the sample to wild-type PF4, to
    (2) the reactivity of antibodies in the sample to a mutant PF4 monomer that remains in a monomeric state; and
  iii) diagnosing the subject as having HIT based on the ratio of (1) to (2).

In some embodiments, the subject is diagnosed as having HIT if the ratio of (1) to (2) in the sample is equal to or greater than a reference ratio of (1) to (2) obtained from a plasma or serum sample from a subject or group of subjects afflicted with HIT.

The present invention also provides a method for determining whether a subject receiving the administration of heparin or a heparin-mimic is at risk of becoming afflicted with heparin-induced thrombocytopenia (HIT), comprising
  i) obtaining a plasma or serum sample from the subject;
  ii) determining the ratio of
    (1) the reactivity of antibodies in the sample to wild-type PF4, to
    (2) the reactivity of antibodies in the sample to a mutant PF4 monomer that remains in a monomeric state; and
  iii) identifying the subject as at risk of becoming afflicted with HIT based on the ratio of (1) to (2).

In some embodiments, the subject is identified as at risk of becoming afflicted with HIT if the ratio of (1) to (2) in the sample is equal to or greater than a reference ratio of (1) to (2) obtained from a plasma or serum sample from a subject or group of subjects not afflicted with HIT, or if the ratio of (1) to (2) in the sample is equal to or greater than a reference ratio of (1) to (2) obtained from a serum or plasma sample taken from the subject before the heparin or the heparin-mimic was administered to the subject.

The present invention also provides a method for monitoring the progression of heparin-induced thrombocytopenia (HIT) in a subject, comprising
- i) obtaining a first plasma or serum sample from the subject;
- ii) obtaining a second plasma or serum sample from the subject;
- iii) determining in each of the first and second samples of the subject the ratio of
  - (1) the reactivity of antibodies in the sample to wild-type PF4, to
  - (2) the reactivity of antibodies in the sample to a mutant PF4 monomer that remains in a monomeric state; and
- iv) determining that HIT has progressed in the subject if the ratio of (1) to (2) is higher in the second sample than in the first sample, and determining that the HIT has not progressed in the subject if the ratio of (1) to (2) is lower in the second sample than in the first sample or if the ratio of (1) to (2) is the same in the first and second samples.

In some embodiments, determining the ratio of (1) and (2) comprises ELISA.

In some embodiments, the ratio of (1) to (2) is obtained using the optical density for (1) and the optical density for (2) obtained using ELISA.

Aspects of the present invention relate to a method for treating a subject afflicted with heparin-induced thrombocytopenia (HIT) comprising administering to the subject an effective amount of an antibody or antibody fragment that is capable of binding at least a portion of the same epitope as the epitope to which RTO binds so as to reduce platelet factor 4 (PF4) oligomerization.

The present invention also provides a method for reducing the likelihood that a subject receiving the administration of heparin or a heparin-mimic will become afflicted with heparin-induced thrombocytopenia (HIT) comprising administering to the subject an effective amount of an antibody or antibody fragment that is capable of binding at least a portion of the same epitope as the epitope to which RTO binds so as to reduce platelet factor 4 (PF4) oligomerization.

In some embodiments, the antibody or antibody fragment is
- (a) RTO or a fragment of RTO;
- (b) a humanized antibody or antibody fragment;
- (c) capable of binding to the same epitope as the epitope to which RTO binds;
- (d) capable of binding to a portion of the same epitope as the epitope to which RTO binds that overlaps with a portion of the same epitope as the epitope to which KKO binds;
- (e) capable of reducing the binding of KKO to PF4; or
- (f) capable of binding between the PF4 AB dimer interface.

In some embodiments, heparin is being or has been administered to the subject.

In some embodiments, the heparin is low-molecular-weight heparin or unfractionated heparin.

In some embodiments, a heparin mimic is being or has been administered to the subject.

In some embodiments, the heparin mimic is fondaparinux.

In some embodiments, HIT has been diagnosed in the subject according to a method of the present invention.

In some embodiments, the subject has been identified as at risk of becoming afflicted with HIT according to a method of the present invention.

In some embodiments, the progression of HIT has been monitored in the subject according to a method of the present invention.

In some embodiments, a method of treating a subject comprises monitoring the progression of HIT in the subject according to a method of the present invention.

The present invention also provides a method for assessing the antigenicity of an anionic anticoagulant comprising
- i) obtaining a plasma or serum sample from a subject who has received administration of the anionic anticoagulant;
- ii) determining the ratio of
  - (1) the reactivity of antibodies in the sample to wild-type PF4, to
  - (2) the reactivity of antibodies in the sample to a mutant PF4 monomer that remains in a monomeric state; and
- iii) assessing the antigenicity of the anionic anticoagulant based on the ratio of (1) to (2).

In some embodiments, the anionic anticoagulant is identified to be capable of increasing the production of pathogenic antibodies in subjects if the ratio of (1) to (2) in the sample is equal to or greater than a reference ratio of (1) to (2) obtained from a plasma or serum sample from a subject or group of subjects not afflicted with HIT, or if the ratio of (1) to (2) in the sample is equal to or greater than a reference ratio of (1) to (2) obtained from a serum or plasma sample taken from the subject before the heparin or the heparin-mimic was administered to the subject.

Aspects of the present invention relate to a method for assessing whether an anionic anticoagulant is capable of causing heparin-induced thrombocytopenia (HIT) comprising
- i) obtaining a plasma or serum sample from a subject who has received administration of the anionic anticoagulant;
- ii) determining the ratio of
  - (1) the reactivity of antibodies in the sample to wild-type PF4, to
  - (2) the reactivity of antibodies in the sample to a mutant PF4 monomer that remains in a monomeric state; and
- iii) assessing whether the anionic anticoagulant is capable of causing HIT based on the ratio of (1) to (2).

In some embodiments, the anionic anticoagulant is identified to be capable of causing HIT if the ratio of (1) to (2) in the sample is equal to or greater than a reference ratio of (1) to (2) obtained from a plasma or serum sample from a subject or group of subjects not afflicted with HIT, or if the ratio of (1) to (2) in the sample is equal to or greater than a reference ratio of (1) to (2) obtained from a serum or plasma sample taken from the subject before the heparin or the heparin-mimic was administered to the subject.

In some embodiments, determining the ratio of (1) and (2) comprises ELISA.

In some embodiments, the ratio of (1) to (2) is obtained using the optical density for (1) and the optical density for (2) obtained using ELISA.

In some embodiments, the subject is a mammalian subject.

In some embodiments, the subject is a human subject.

The present invention provides a mutant protein which has the same amino acid sequence of a wild type PF4 monomer except that
   (i) at least one amino acid of the wild type PF4 monomer has been deleted,
   (ii) at least one amino acid of the wild type PF4 monomer has been replaced by another amino acid, or
   (iii) a combination of such changes has been made.

In some embodiments, the mutant protein the at least one amino acid that has been deleted or replaced is on the N-terminal end of the mutant PF4 monomer.

In some embodiments, at least 8 amino acids are deleted from the N-terminal end of a wild type PF4 monomer.

In one embodiment, the mutant PF4 monomer is a K53E mutant.

In some embodiments, the amino acid sequence of the mutant protein is set forth is SEQ ID NO: 15.

In some embodiments, the mutant protein interferes with wild type PF4 tetramer oligomerization.

The present invention also provides a method for treating a subject afflicted with heparin-induced thrombocytopenia (HIT) comprising administering to the subject an effective amount of a mutant PF4 monomer so as to interfere with PF4 tetramer oligomerization.

The present invention also provides a method for reducing the likelihood that a subject receiving the administration of heparin or a heparin-mimic will become afflicted with heparin-induced thrombocytopenia (HIT) comprising administering to the subject an effective amount of a mutant PF4 monomer so as to interfere with PF4 tetramer oligomerization.

The present invention also provides a method for treating coagulation pathologies that lead to thrombus formation, angiogenesis or abnormal cell growth comprising administering to the subject an effective amount of a mutant platelet factor 4 (PF4) monomer so as to interfere with PF4 tetramer oligomerization.

Each embodiment disclosed herein is contemplated as being applicable to each of the other disclosed embodiments. Thus, all combinations of the various elements described herein are within the scope of the invention.

Diagnostic and Screening Assays

Patients have pathogenic and non-pathogenic anti-PF4 antibodies in their plasmas. The proportion of each type of antibodies varies among patients but this difference cannot be detected using current ELISAs because the wells contain PF4 monomers, tetramers and various sized oligomers.

Identifying antibodies that bind to monomers, i.e. are nonpathogenic, helps to eliminate the detection of clinically irrelevant antibodies that current cause false positive diagnoses, label patients as allergic to heparin and cause them to receive expensive anticoagulants that cannot be reversed if bleeding occurs. Therefore there is a need to develop a new assay that provides a higher true positive result rate than is currently available.

The logic for diagnostic assays provided in the present invention is as follows.
   1. Oligomerization of PF4 is a fundamental step in the pathogenesis of HIT
   2. PF4 is synthesized as a monomer but oligomerizes at high concentrations, a process that is enhanced to a variable extent by anionic polysaccharides, some of which are used as anticoagulants, e.g. heparins
   3. KKO identifies the oligomeric (pathogenic) state of PF4
   4. A mutant PF4 monomer that does not oligomerize (e.g. by deletion of 8 amino acids from the N-terminal) prevents the formation of a tetramer with a KKO binding site, therefore KKO binds to wild type PF4 but not to the mutant monomer;
   5. RTO or other non-pathogenic antibodies bind to monomeric PF4 and monomeric wild type (wt) PF4 to the same or similar extent Based on this the present invention provides a test in which one target is wt PF4 and one target is a mutant PF4 monomer that remains in the monomeric state. Pathogenic antibodies in plasma will bind to wt PF4 but not the mutant PF4 monomer. In contrast, non-pathogenic antibodies will bind to wt PF4 and the mutant PF4 monomer. Therefore the OD wtPF4/OD M11 can be used to distinguish patients at high risk of HIT from the far greater number of individuals who develop clinically irrelevant antibodies that now give false positive results.

Mutant PF4 monomers that remain in the monomeric state can also be used for this purpose.

Another variation on this concept is that the increase in the OD wtPF4/OD mutant PF4 monomer ratio can be used to assess the antigenicity of existing and potential new anionic anticoagulants.

```
WT-PF4: sequence
                                (SEQ ID NO: 11)
EAEEDGDLQCLCVKTTSQVRPRHITSLEVIKAGPH

CPTAQLIATLKNGRKICLDLQAPLYKKIIKKLLES
```

Terms

Unless otherwise defined, all technical and scientific terms used herein have the same meaning as commonly understood by a person of ordinary skill in the art to which this invention belongs.

As used herein, and unless stated otherwise or required otherwise by context, each of the following terms shall have the definition set forth below.

As used herein, "about" in the context of a numerical value or range means ±10% of the numerical value or range recited or claimed, unless the context requires a more limited range.

It is understood that where a parameter range is provided, all integers within that range, and tenths thereof, are also provided by the invention. For example, "0.2-5 mg/kg/day" is a disclosure of 0.2 mg/kg/day, 0.3 mg/kg/day, 0.4 mg/kg/day, 0.5 mg/kg/day, 0.6 mg/kg/day etc. up to 5.0 mg/kg/day.

The terms "treating" or "treatment" refer to any success or indicia of success in the attenuation or amelioration of an injury, pathology or condition, including any objective or subjective parameter such as abatement, remission, diminishing of symptoms or making the injury, pathology, or condition more tolerable to the patient, slowing in the rate of degeneration or decline, making the final point of degeneration less debilitating, improving a subject's physical or mental well-being, or prolonging the length of survival. The treatment or amelioration of symptoms can be based on objective or subjective parameters; including the results of a physical examination, neurological examination, and/or psychiatric evaluations.

"Effective amount" and "therapeutically effective amount" are used interchangeably herein, and refer to an amount of a compound effective to achieve a particular biological or therapeutic result such as, but not limited to, biological or therapeutic results disclosed, described, or exemplified herein. A therapeutically effective amount of the compound may vary according to factors such as the disease state, age, sex, and weight of the subject, and the ability of the antibody or antigen-binding fragment thereof to elicit a desired response in the subject. In embodiments of the invention, such results may include, but are not limited to, the treatment of heparin-induced thrombocytopenia (HIT), as determined by any means suitable in the art.

Antibodies

The term "antibody" is used in the broadest sense and specifically covers monoclonal antibodies (including full length monoclonal antibodies), polyclonal antibodies, multispecific antibodies (e.g., bispecific antibodies), monovalent antibodies, and multivalent antibodies. Additionally, the term "antibody" refers to all isotypes of immunoglobulins (IgG, IgA, IgE, IgM, IgD, and IgY) including various monomeric and polymeric forms of each isotype, unless otherwise specified.

"Antibody fragments" comprise a portion of a full length antibody, generally the antigen binding or variable region thereof. Examples of antibody fragments include but are not limited to Fv, Fab, Fab', Fab'-SH, F(ab')$_2$; diabodies; linear antibodies; single-chain antibody molecules (e.g., scFv); and multispecific antibodies formed from antibody fragments. Various techniques have been developed for the production of antibody fragments, including proteolytic digestion of antibodies and recombinant production in host cells; however, other techniques for the production of antibody fragments will be apparent to the skilled practitioner. In some embodiments, the antibody fragment of choice is a single chain Fv fragment (scFv). "Single-chain Fv" or "scFv" antibody fragments comprise the V H and V L domains of antibody, wherein these domains are present in a single polypeptide chain. Generally, the Fv polypeptide further comprises a polypeptide linker between the V H and V L domains which enables the scFv to form the desired structure for antigen binding. For a review of scFv and other antibody fragments, see James D. Marks, Antibody Engineering, Chapter 2, Oxford University Press (1995) (Carl K. Borrebaeck, Ed.).

The term "epitope" refers to a portion of a molecule (the antigen) that is capable of being bound by a binding agent, e.g., an antibody, at one or more of the binding agent's antigen binding regions. Epitopes usually consist of specific three-dimensional structural characteristics, as well as specific charge characteristics.

As used herein, "monoclonal antibody" means an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations that typically include different antibodies directed against different determinants, each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler and Milstein, Nature 256:495-97 (1975), or may be made by recombinant DNA methods (see, e.g., U.S. Pat. No. 4,816,567). The monoclonal antibodies may also be isolated from phage display libraries using the techniques described, for example, in Clackson et al., Nature 352:624-28 (1991) and Marks et al., J. Mol. Biol. 222(3): 581-97 (1991).

The term "hybridoma" or "hybridoma cell line" refers to a cell line derived by cell fusion, or somatic cell hybridization, between a normal lymphocyte and an immortalized lymphocyte tumor line. In particular, B cell hybridomas are created by fusion of normal B cells of defined antigen specificity with a myeloma cell line, to yield immortal cell lines that produce monoclonal antibodies. In general, techniques for producing human B cell hybridomas, are well known in the art (Kozbor et al., Immunol. Today 4:72 (1983); Cole et al., in Monoclonal Antibodies and Cancer Therapy, Alan R. Liss, Inc. 77-96 (1985)).

The term "humanized antibodies" means antibodies that contain minimal sequence derived from non-human immunoglobulin sequences. For the most part, humanized antibodies are human immunoglobulins (recipient antibody) in which residues from a hyper variable region of the recipient are replaced by residues from a hypervariable region of a non-human species (donor antibody) such as mouse, rat, rabbit or nonhuman primate having the desired specificity, affinity, and capacity. See, for example, U.S. Pat. Nos. 5,225,539; 5,585,089; 5,693,761; 5,693,762; 5,859,205, each herein incorporated by reference. In some instances, framework residues of the human immunoglobulin are replaced by corresponding non-human residues (see, for example, U.S. Pat. Nos. 5,585,089; 5,693,761; 5,693,762, each herein incorporated by reference). Furthermore, humanized antibodies may comprise residues that are not found in the recipient antibody or in the donor antibody. These modifications are made to further refine antibody performance (e.g., to obtain desired affinity). In general, the humanized antibody will comprise substantially all of at least one, and typically two, variable domains, in which all or substantially all of the hypervariable regions correspond to those of a non-human immunoglobulin and all or substantially all of the framework regions are those of a human immunoglobulin sequence. The humanized antibody optionally also will comprise at least a portion of an immunoglobulin constant region (Fc), typically that of a human immunoglobulin. For further details see Jones et al., Nature 331:522-25 (1986); Riechmann et al., Nature 332:323-27 (1988); and Presta, Curro Opin. Struct. Biol. 2:593-96 (1992), each of which is incorporated herein by reference.

An immunoglobulin light or heavy chain variable region consists of a "framework" region interrupted by three hypervariable regions. Thus, the term "hypervariable region" refers to the amino acid residues of an antibody which are responsible for antigen binding. The hypervariable region comprises amino acid residues from a "Complementarity Determining Region" or "CDR" and/or those residues from a "hypervariable loop" in the heavy chain variable domain; Chothia and Lesk, 1987, J. Mol. Biol. 196: 901-917). "Framework Region" or "FR" residues are those variable domain residues other than the hypervariable region residues as herein defined. The sequences of the framework regions of different light or heavy chains are relatively conserved within a species. Thus, a "human framework region" is a framework region that is substantially identical (about 85% or more, usually 90-95% or more, such as 100%) to the framework region of a naturally occurring human immunoglobulin. The framework region of an antibody, that is the combined framework regions of the constituent light and heavy chains, serves to position and align the CDR's. The CDR's are primarily responsible for binding to an epitope of an antigen. Antibodies of the invention also include antibodies produced in a non-human mammalian host, more particularly a transgenic mouse, characterized by inactivated endogenous immunoglobulin (Ig) loci. In such transgenic animals, competent endogenous genes for the expression of light and heavy subunits of host immunoglobulins are rendered non-functional and substituted with the analogous human immunoglobulin loci. These transgenic animals produce human antibodies in the substantial absence of light or heavy host immunoglobulin subunits. See, for example, U.S. Pat. No. 5,939,598, the entire contents of which are incorporated herein by reference.

Those skilled in the art will be aware of how to produce antibody molecules of the present invention. For example, polyclonal antisera or monoclonal antibodies can be made using standard methods. A mammal, (e.g., a mouse, hamster, or rabbit) can be immunized with an immunogenic form of the protein which elicits an antibody response in the mammal. For instance, a mammal can be immunized with irradiated cells that were transfected with a nucleic acid encoding the protein such that high levels of the protein were expressed on the cell surface. The progress of immunization can be monitored by detection of antibody titers in plasma or serum. Standard ELISA or other immunoassay can be used with the immunogen as antigen to assess the levels of antibodies. Following immunization, antisera can be obtained, and, if desired IgG molecules corresponding to the polyclonal antibodies may be isolated from the sera.

To produce monoclonal antibodies, antibody producing cells (lymphocytes) can be harvested from an immunized animal and fused with myeloma cells by standard somatic cell fusion procedures thus immortalizing these cells and yielding hybridoma cells. Such techniques are well known in the art. Hybridoma cells can be screened immunochemically for production of antibodies which are specifically reactive with the oligopeptide, and monoclonal antibodies isolated.

Polynucleotides and Expression

The proteins and fragments thereof described herein can be made by recombinant processes and, therefore, may include amino acid sequences derived from more than one species (i.e. chimeric constructs) or may be engineered to have a human, or human-like, amino acid composition (i.e., a humanized construct). Accordingly, provided herein are vectors comprising polynucleotides capable of encoding the described proteins and fragments thereof. The vectors can be expression vectors. Recombinant expression vectors containing a sequence encoding a polypeptide of interest are thus provided. The expression vector may contain one or more additional sequences such as, but not limited to, regulatory sequences (e.g., promoter, enhancer), a selection marker, and a polyadenylation signal. Vectors for transforming a wide variety of host cells are well known to those of skill in the art. They include, but are not limited to, plasmids, phagemids, cosmids, baculoviruses, bacmids, bacterial artificial chromosomes (BACs), yeast artificial chromosomes (YACs), as well as other bacterial, yeast and viral vectors. The vectors described herein may be integrated into the host genome or maintained independently in the cell or nucleus.

A "vector" is a replicon, such as plasmid, phage, cosmid, or virus in which another nucleic acid segment may be operably inserted so as to bring about the replication or expression of the segment.

The term "operably linked" or "operably inserted" means that the regulatory sequences necessary for expression of the coding sequence are placed in a nucleic acid molecule in the appropriate positions relative to the coding sequence so as to enable expression of the coding sequence. By way of example, a promoter is operably linked with a coding sequence when the promoter is capable of controlling the transcription or expression of that coding sequence. Coding sequences can be operably linked to promoters or regulatory sequences in a sense or antisense orientation. The term "operably linked" is sometimes applied to the arrangement of other transcription control elements (e.g., enhancers) in an expression vector.

The terms "express" and "produce" are used synonymously herein, and refer to the biosynthesis of a gene product. These terms encompass the transcription of a gene into RNA. These terms also encompass translation of RNA into one or more polypeptides, and further encompass all naturally occurring post-transcriptional and post-translational modifications. The expression/production of an antibody or antigen-binding fragment can be within the cytoplasm of the cell, and/or into the extracellular milieu such as the growth medium of a cell culture.

Recombinant expression vectors contemplated to be within the scope of the description include synthetic, genomic, or cDNA-derived nucleic acid fragments that encode at least one recombinant protein which may be operably linked to suitable regulatory elements. Such regulatory elements may include a transcriptional promoter, sequences encoding suitable mRNA ribosomal binding sites, and sequences that control the termination of transcription and translation. Expression vectors, especially mammalian expression vectors, may also include one or more nontranscribed elements such as an origin of replication, a suitable promoter and enhancer linked to the gene to be expressed, other 5' or 3' flanking nontranscribed sequences, 5' or 3' nontranslated sequences (such as necessary ribosome binding sites), a polyadenylation site, splice donor and acceptor sites, or transcriptional termination sequences. An origin of replication that confers the ability to replicate in a host may also be incorporated. Such vectors may be integrated into the host genome or maintained independently in the cell or nucleus.

The vectors described herein can be used to transform various cells with the genes encoding the disclosed proteins. For example, the vectors may be used to generate scaffold or antigen-binding protein-producing cells or cell lines. Thus, another aspect features host cells transformed with vectors comprising a nucleic acid sequence encoding a protein. The host cells disclosed herein can be prokaryotic or eukaryotic cells, For example the host cell can be a bacteria. In a preferred embodiment, the bacterial host cell is *E. coli*. Of course, the host cell can also be a mammalian cell, such as a Chinese hamster ovary (CHO) cell line. Numerous other such host cells, prokaryotic and eukaryotic, are known in the art and are considered to be within the scope of this disclosure.

Numerous techniques are known in the art for the introduction of foreign genes into cells and may be used to construct the recombinant cells for purposes of carrying out the inventive methods and producing proteins as described herein, in accordance with the various embodiments described and exemplified herein. The technique used should provide for the stable transfer of the heterologous gene sequence to the host cell, such that the heterologous gene sequence is heritable and expressible by the cell progeny, and so that the necessary development and physiological functions of the recipient cells are not disrupted. Techniques which may be used include but are not limited to chromosome transfer (e.g., cell fusion, chromosome mediated gene transfer, micro cell mediated gene transfer), physical methods (e.g., transfection, spheroplast fusion, microinjection, electroporation, liposome carrier), viral vector transfer (e.g., recombinant DNA viruses, recombinant RNA viruses) and the like. Calcium phosphate precipitation and polyethylene glycol (PEG)-induced fusion of bacterial protoplasts with mammalian cells can also be used to transform cells.

It is fully contemplated that the vectors such as those described herein can be used to transform prokaryotic and/or eukaryotic cells to facilitate expression of the described proteins. In some embodiments the described vectors are used to facilitate protein expression in bacteria, such as E. coli. While any E. coli strain can be used to express the proteins described herein, some preferred strains include: BL21 (DE3), BL21-CodonPlus® (DE3)-RP, BL21-Codon Plus® (DE3)-RIL, BL21-(DE3)-pLysS (Stratagene). Eukaryotic cells can also be used with vectors to facilitate protein expression. While those of skill in the art will recognize that a wide variety of eukaryotic cells will be suitable for this purpose, some preferred embodiments include mammalian cells and insect cells. For example, in one embodiment Chinese hamster ovary (CHO) cells can be used with the vectors to facilitate expression of the protein constructs provided herein. In alternative embodiments, insect cells, such as Sf9 cells or S2 cells, can be used to with the described vectors to facilitate expression of the protein constructs provided herein. Furthermore, those of skill in the art will understand that vectors, not expressly disclosed herein, can be used for the same purpose of expressing, or replicating nucleic acids encoding, the described antigen binding proteins.

The described proteins can be encoded by a variety of polynucleotides capable of encoding the amino acid sequences provided herein. These polynucleotides can also be incorporated into vectors useful for the maintenance, replication, and/or expression of the polynucleotides encoding the described antigen-binding proteins or the described portions thereof. The vectors described above can be used to engineer cells to express the antigen-binding proteins or the described portions thereof encoded by the polynucleotides disclosed herein.

Compositions

Also described herein are compositions containing a protein or proteins of the invention and a pharmaceutically acceptable carrier. Such compositions can be used to administer the described proteins to a subject or store or to maintain the described proteins. Any of the described proteins can be used to produce such compositions, which may include more than one of the disclosed proteins. In addition, such compositions can include other agents, such as therapeutic agents, preservatives, antimicrobial agents, and the like.

Described herein are compositions comprising at least one disclosed protein and a pharmaceutically acceptable carrier. The compositions can be formulated as any of various preparations that are known and suitable in the art, including those described and exemplified herein. In some embodiments, the compositions are aqueous formulations. Aqueous solutions can be prepared by admixing the antigen-binding proteins in water or suitable physiologic buffer, and optionally adding suitable colorants, flavors, preservatives, stabilizing and thickening agents and the like as desired. Aqueous suspensions can also be made by dispersing the antigen-binding proteins in Water or physiologic buffer with viscous material, such as natural or Synthetic gums, resins, methylcellulose, sodium carboxymethylcellulose, and other well-known suspending agents.

Also included are liquid formulations and solid form preparations which are intended to be converted, shortly before use, to liquid preparations. Such liquids include solutions, suspensions, syrups, slurries, and emulsions. Liquid preparations may be prepared by conventional means with pharmaceutically acceptable additives such as suspending agents (e.g., sorbitol syrup, cellulose derivatives or hydrogenated edible fats or oils); emulsifying agents (e.g., lecithin or acacia); non-aqueous vehicles (e.g., almond oil, oily esters, or fractionated vegetable oils); and preservatives (e.g., methyl or propyl-p-hydroxybenzoates or sorbic acid). These preparations may contain, in addition to the active agent, colorants, flavors, stabilizers, buffers, artificial and natural sweeteners, dispersants, thickeners, solubilizing agents, and the like. The compositions may be in powder or lyophilized form for constitution With a suitable vehicle such as sterile water, physiological buffer, saline solution, or alcohol, before use.

The compositions can be formulated for injection into a subject. For injection, the compositions described can be formulated in aqueous solutions such as water or alcohol, or in physiologically compatible buffers such as Hanks's solution, Ringer's solution, or physiological saline buffer. The solution may contain formulatory agents such as suspending, stabilizing and/or dispersing agents. Injection formulations may also be prepared as solid form preparations which are intended to be converted, shortly before use, to liquid form preparations suitable for injection, for example, by constitution with a suitable vehicle, such as sterile water, saline solution, or alcohol, before use.

The compositions can be formulated in sustained release vehicles or depot preparations. Such long acting formulations may be administered by implantation (for example subcutaneously or intramuscularly) or by intramuscular injection. Thus, for example, the compositions may be formulated with suitable polymeric or hydrophobic materials (for example, as an emulsion in an acceptable oil) or ion exchange resins, or as sparingly soluble derivatives, for example, as a sparingly soluble salt. Liposomes and emulsions are well-known examples of delivery vehicles suitable for use as carriers for hydrophobic drugs.

The proteins described herein may be administered orally in any acceptable dosage form such as capsules, tablets, aqueous suspensions, solutions or the like. The proteins may also be administered parenterally including but not limited to: subcutaneous, intravenous, intramuscular, intra-articular, intra-synovial, intrasternal, intranasal, topically, intrathecal, intrahepatic, intralesional, and intracranial injection or infusion techniques. Generally, the proteins will be intravenously or intraperitoneally, for example, by injection.

The subject can be any animal, and preferably is a mammal such as a mouse, rat, hamster, guinea pig, rabbit, cat, dog, monkey, donkey, cow, horse, pig, and the like. In some embodiments, the mammal is a human. In some embodiments, the mammal is other than a human.

All publications and other references mentioned herein are incorporated by reference in their entirety, as if each individual publication or reference were specifically and individually indicated to be incorporated by reference. Publications and references cited herein are not admitted to be prior art.

The present invention is not intended to be limited by any theory. This invention will be better understood by reference to the Experimental Details which follow, but those skilled in the art will readily appreciate that the specific experiments detailed are only illustrative of the invention as defined in the claims which follow thereafter.

EXPERIMENTAL DETAILS

Examples are provided below to facilitate a more complete understanding of the invention. The following examples illustrate the exemplary modes of making and practicing the invention. However, the scope of the invention is not limited to specific embodiments disclosed in these Examples, which are for purposes of illustration only.

Example 1

Heparin-induced thrombocytopenia (HIT) is an autoimmune thrombotic disorder caused by immune complexes containing platelet factor 4 (PF4), antibodies to PF4, and heparin or cellular glycosaminoglycans (GAGS). We solved the crystal structures of the: 1) PF4 tetramer/fondaparinux complex, 2) PF4 tetramer/KKOFab complex (a murine monoclonal HIT-like antibody), and 3) PF4 monomer/RTO-Fab complex (a non-HIT anti-PF4 monoclonal antibody). Fondaparinux binds to the 'closed' end of the PF4 tetramer and stabilizes its conformation. This interaction in turn stabilizes the epitope for KKO on the "open" end of the tetramer. Fondaparinux and KKO thereby collaborate to "stabilize" the ternary pathogenic immune complex. Binding of RTO to PF4 monomers prevents PF4 tetramerization and inhibits KKO and human HIT IgG-induced platelet activation and platelet aggregation in vitro, and thrombus progression in vivo. The atomic structures provide a basis to develop new diagnostics and non-anticoagulant therapeutics for HIT.

Introduction

Heparin-induced thrombocytopenia/thrombosis (HIT) is a potentially fatal immune complex mediated thrombotic disorder that develops in approximately 1% of patients exposed to unfractionated heparin (UFH) or, less commonly, to low-molecular-weight heparins (LMWH) (Linkins 2012). HIT is caused by antibodies to complexes that form between platelet factor 4 (PF4) released from activated platelets and heparin or cellular glycosaminoglycans (GAGS). Circulating immune complexes composed of PF4, heparin, and HIT antibodies bind to platelet and monocyte Fcy receptors and promote cellular activation, leading to generation of thrombin (Phillips 2008; Lee 2013; Lewis 2003). Anti-PF4/heparin antibodies detected by ELISA also develop in a high proportion of patients exposed to heparin, e.g., after cardiopulmonary bypass surgery, even in the absence of clinical complications. However, the basis for the distinction between pathogenic and non-pathogenic antibodies is unknown, which can lead to over-diagnosis and overtreatment (Cuker 2012).

In prior studies, we identified a murine monoclonal antibody (KKO) to PF4/heparin complexes that causes heparin-induced thrombosis and thrombocytopenia in a murine model, thus sharing salient features with the clinical disorder (Arepally 2000). Human HIT antibodies compete with KKO for binding to PF4/heparin, and KKO augments formation of pathogenic immune complexes (Sachais 2012). An isotype matched anti-PF4 antibody (RTO) that binds comparably to PF4, but does not cause pathogenic complexes (Zhang 1994), has also been identified.

Here, we describe and compare the crystal structures of PF4 in complex with Fabs derived from KKO and RTO and the structure of PF4 in complex with a heparin-mimic pentasaccharide, fondaparinux. These results suggest that by stabilizing the structure of the asymmetric PF4 tetramer, fondaparinux might foster the binding of HIT antibody and formation of the pathogenic ternary complex. Surprisingly, the non-HIT antibody RTO binds to an epitope expressed on the surface of the PF4 monomer that partly overlaps with the KKO epitope in the tetramer. Binding of RTO prevents tetramerization of PF4 and inhibits KKO-induced platelet activation and aggregation in vitro and has potent inhibitory effects on thrombus progression in vivo.

These crystallographic data lead to a model to help understand the structural basis of the pathogenic immune complex that causes HIT at the atomic level and provide a structural basis for the development of new diagnostics and non-anticoagulant therapeutics for HIT. The data described herein also provides insights into the process through which a normal human protein becomes "antigenic" to the mammalian immune system after complexing with endogenous or exogenous GAGS.

Results

Crystal Structure of the PF4/Fondaparinux Complex: Generation of the HIT Antigen Based on previously reported crystal structures, human PF4 can assume an asymmetric tetrameric configuration. Each monomer contains three-stranded antiparallel β-sheets upon which an aperiodic N-terminal domain and an amphipathic C-terminal α-helix are folded 9. NMR studies reveal that PF4 exists as an equilibrium among monomers, dimers and tetramers (Mayo 1989). The tetrameric structure of PF4 is stabilized not only by salt bridge interactions between dimers AB/CD (hereafter we use the nomenclature for the monomer chains of PF4 as in PDB: 1RHP 9), but also by the antiparallel 3-sheet-like structures in the N-termini of dimers AC or BD 9. It had been assumed that the asymmetry of the PF4 tetramer plays a role in heparin binding (Mayo 1995) and several models have been proposed to explain the interaction between heparin and PF4 (Cowan 1986; Stuckey 1992; Nguyen 2015). However, conclusive structural data at the atomic level have not been reported.

Binding of pathogenic HIT antibodies to PF4 is markedly enhanced by heparin or various glycosaminoglycans (GAGS), which are themselves highly heterogeneous in size and composition and unsuitable for crystallization. To investigate how the GAG might induce or augment neoantigen formation, we crystallized PF4 in complex with fondaparinux, a homogenous synthetic pentasaccharide heparin that forms complexes with PF4 as assessed by atomic force microscopy and photon correlation spectroscopy (Greinacher 2006). Fondaparinux induces anti-PF4/heparin antibodies as do other GAGS (Bauer 2001; Turpie 2002; Warkentin 2005) and can occasionally cause HIT (Rota 2008; Warkentin 2008; Warkentin 2007; Bhatt 2013).

Figure 1B:
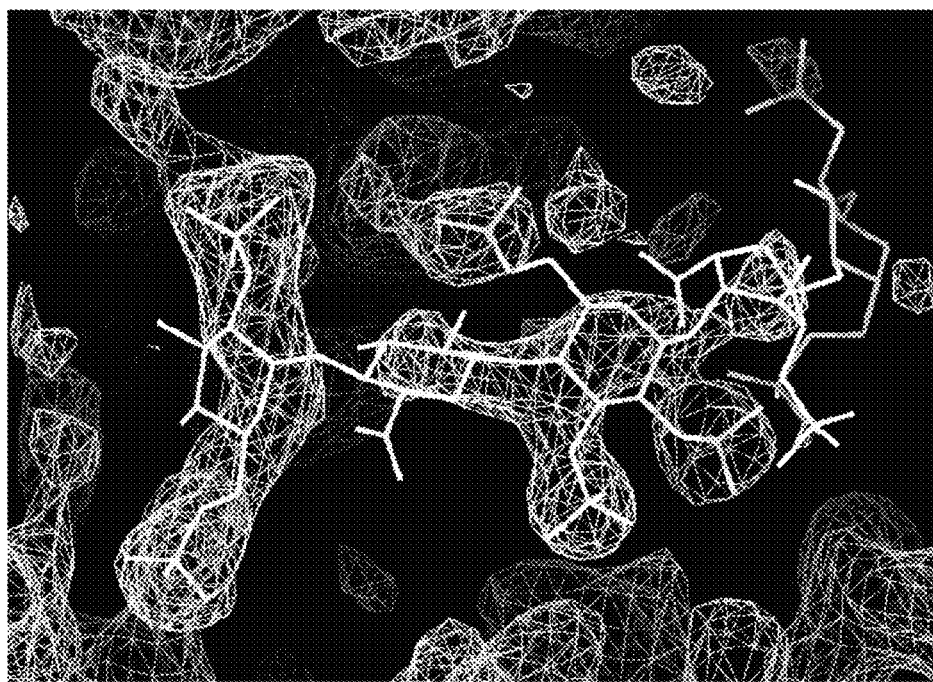
Figure 9A:
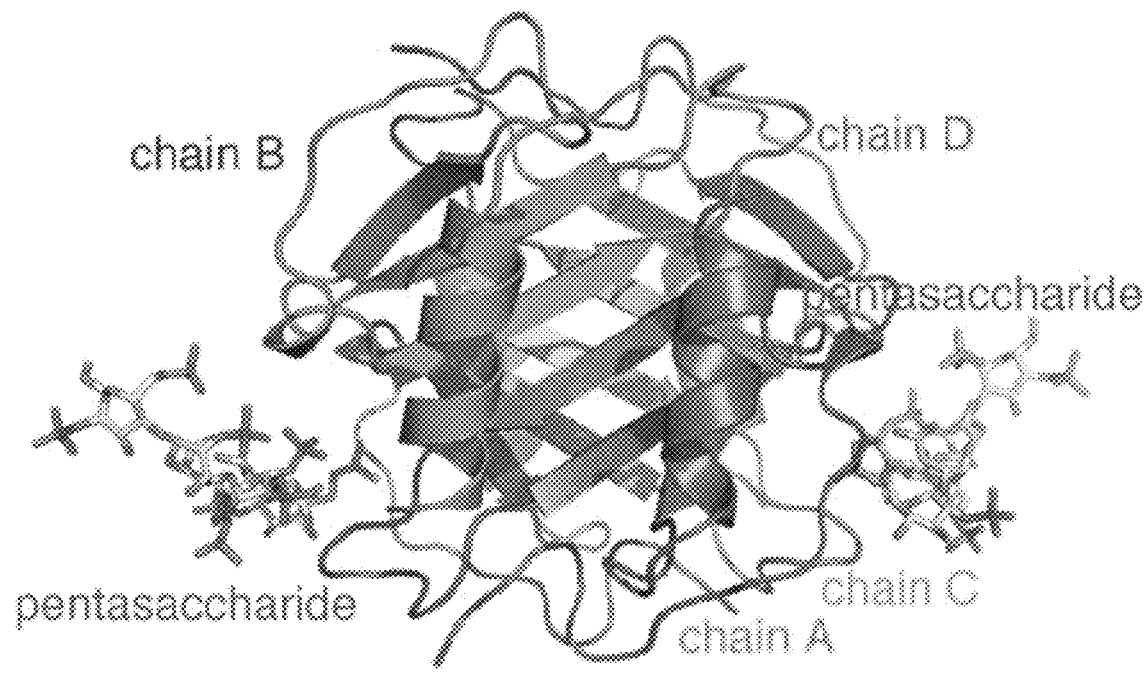
FIG. 9A, FIG. 9B, FIG. 9C, FIG. 9D, FIG. 9E, and FIG. 9F. Crystal structure of the PF4/fondaparinux complex and formation of the HIT antigen.

We solved the crystal structure of PF4 in complex with fondaparinux as a model GAG. The PF4/fondaparinux complex is a pseudo-222 tetramer formed by a pseudo 2-fold non-crystallographic symmetry (NCS) and a 2-fold crystallographic symmetry perpendicular (FIG. 9A, Table 1 for statistics). Fondaparinux appears as a well-defined molecule, evidenced by the strong and clear electron densities (FIG. 1A and FIG. 1B). Superposition of the bound and non-bound structures of PF4 tetramer (PDB:IRHP) using Ca gives a root-mean-square deviation of only 0.76 Å. This indicates that the association with fondaparinux causes minimal conformational changes in PF4 except for slight re-direction of side chains around the binding groove, which is consistent with CD studies reported recently (Brandt 2014; Kreimann 2014).

undergo close approximation (Nguyen 2015; Greinacher 2006). The crystal structure of the PF4/fondaparinux complex provides a more complete atomic understanding of this

TABLE 1

Summary of Crystalloaraphic data and Refinement Statistics

|  | PF4/Fondaparinux | KKOFab | KKOFab/PF4 tetramer | RTOFab/PF4 monomer |
|---|---|---|---|---|
| Data Collection |  |  |  |  |
| Beamline | X4A/X4C(BNL) | X6A(BNL) | X4A/X4C(BNL) | X4A/X4C(BNL) |
| wavelength (Å) | 0.9791 | 0.9795 | 0.9792 | 2.07 |
| Space group | $P3_221$ | $P2_12_12_1$ | $P2_12_12_1$ | $P2_12_12$ |
| Cell dimensions | a = 67.33 Å | a = 41.48 Å | a = 49.49 Å | a = 161.42 Å |
|  | b = 67.33 Å | b = 92.12 Å | b = 99.34 Å | b = 171.87 Å |
|  | c = 61.76 Å | c = 122.14 Å | c = 261.74 Å | c = 208.16 Å |
|  | $\alpha = \beta = 90°, \gamma = 120°$ | $\alpha = \beta = \gamma = 90°$ | $\alpha = \beta = \gamma = 90°$ | $\alpha = \beta = \gamma = 90°$ |
| Resolution * (Å) | 2.50 (2.54-2.50) | 2.20 (2.28-2.20) | 4.10 (4.17-4.10) | 3.75 (3.81-3.75) |
| Rsym or Rmerge | 0.057 (0.72) | 0.088 (0.66) | 0.089 (0.44) | 0.154 (1.65) |
| I/σI | 22.6 (3.0) | 10.8 (2.2) | 7.9 (1.9) | 6.8 (2.9) |
| Completeness (%) | 98.2 (98.6) | 94.4 (98.5) | 87.9 (61.3) | 99.4 (98.9) |
| Redundancy | 10.3 (10.0) | 5.1 (4.9) | 8.9 (4.5) | 26.5 (25.6) |
| Refinement |  |  |  |  |
| Resolution (Å) | 22.76-2.50 | 30.8-2.20 | 20-4.11 | 50-3.74 |
| No. unique reflections | 5913 | 24599 | 10642 | 60619 |
| $R_{work}/R_{free}$ | 0.224/0.245 | 0.200/0.262 | 0.317/0.382 | 0.257/0.297 |
| No. atoms |  |  |  |  |
| Protein | 973 | 3322 | 8548 | 30074 |
| Solvent | 17 | 99 | 0 | 0 |
| B-factors (Å$^2$) |  |  |  |  |
| Protein | 95 | 37 | 268 | 134 |
| ligand | 157 | NA | NA | NA |
| R.m.s deviations |  |  |  |  |
| Bond lengths (Å) | 0.006 | 0.008 | 0.006 | 0.007 |
| Bond angles (°) | 0.93 | 1.17 | 0.92 | 1.34 |
| Ramachandran (%) |  |  |  |  |
| Favored/disallowed | 100/0 | 99.4/0.3 | 97.1/0.8 | 97.4/1.0 |

* Values in the outermost shell are given in parentheses

Figures 2, 3:
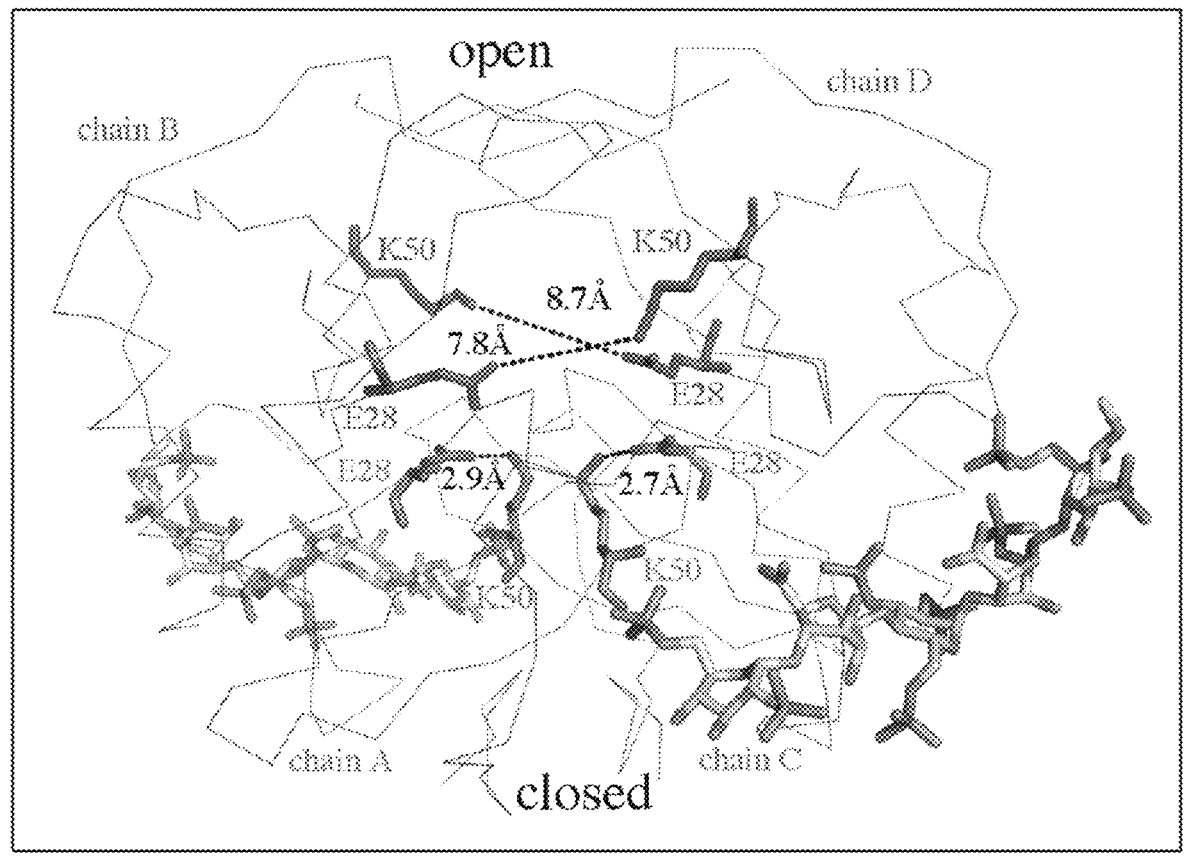
FIG. 2. The asymmetric 'open'-'close' conformation in the PF4/fondaparinux complex crystal. Measurement of the E28 to K50 distances shows that PF4 in the PF4/fondaparinux complex crystal adopts an asymmetric 'open'-'closed' conformation, which is almost same as in the apo-PF4 crystal structure. Salt bridges exist between chain A and chain C, not between chain B and chain D, in the asymetric tetramer. Fondaparinux binds only to the close end of PF4 tetramer and stabilizes the tetramer structure. Only two binding grooves for fondaparinux are present on the surface of the PF4 tetramer due to the asymmetry.
FIG. 3. Structure-based mutations of KKO epitopes on the PF4 surface. Sequence alignment of human PF4 (SEQ ID NO: 11) with mouse PF4 (SEQ ID NO: 12) guided inventors to make structure-based mutations in the KKO epitope (FIG. 2B). PF4-SCV$^{9-11}$; PF4-R$^{55}$.
Figure 9B:
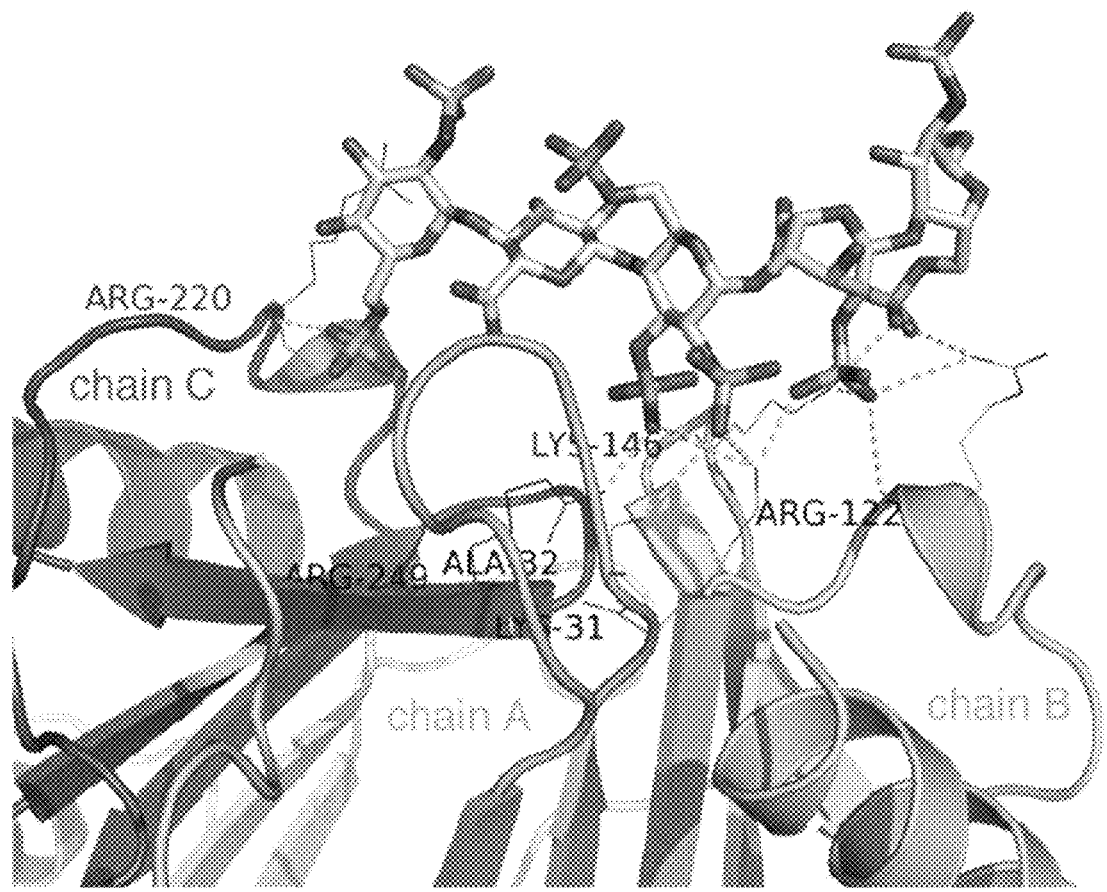
Figure 9C:
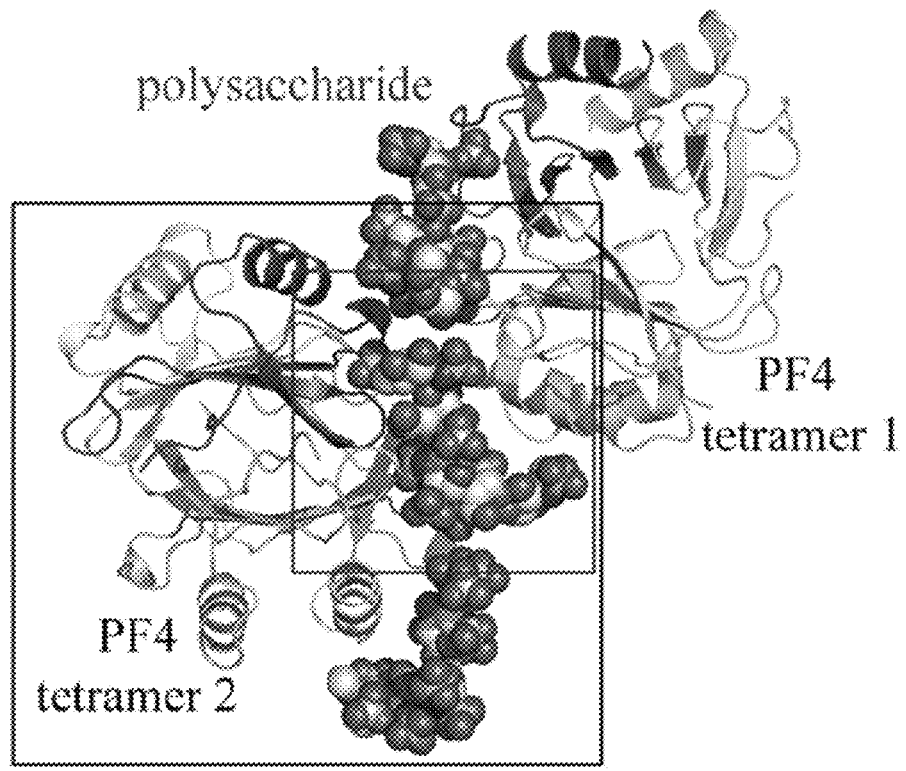
Figure 9D:
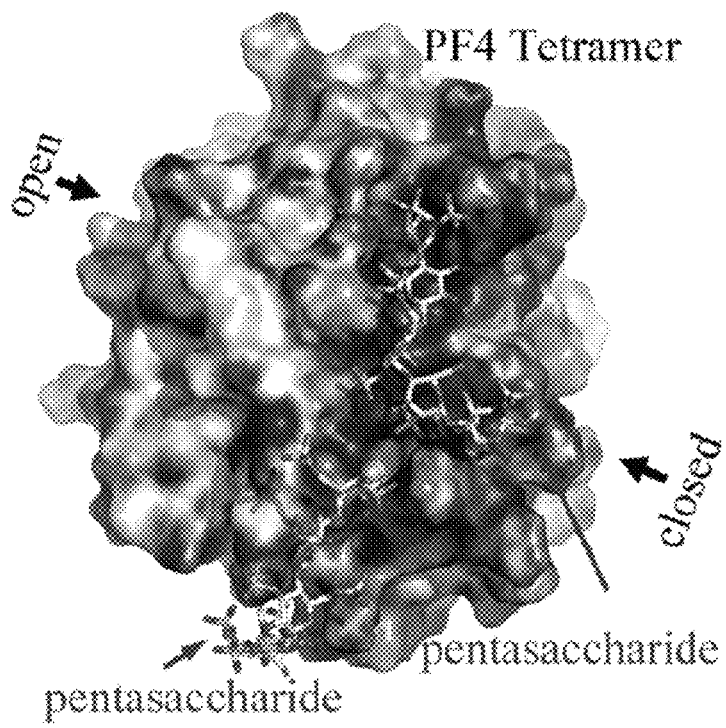
Figure 9E:
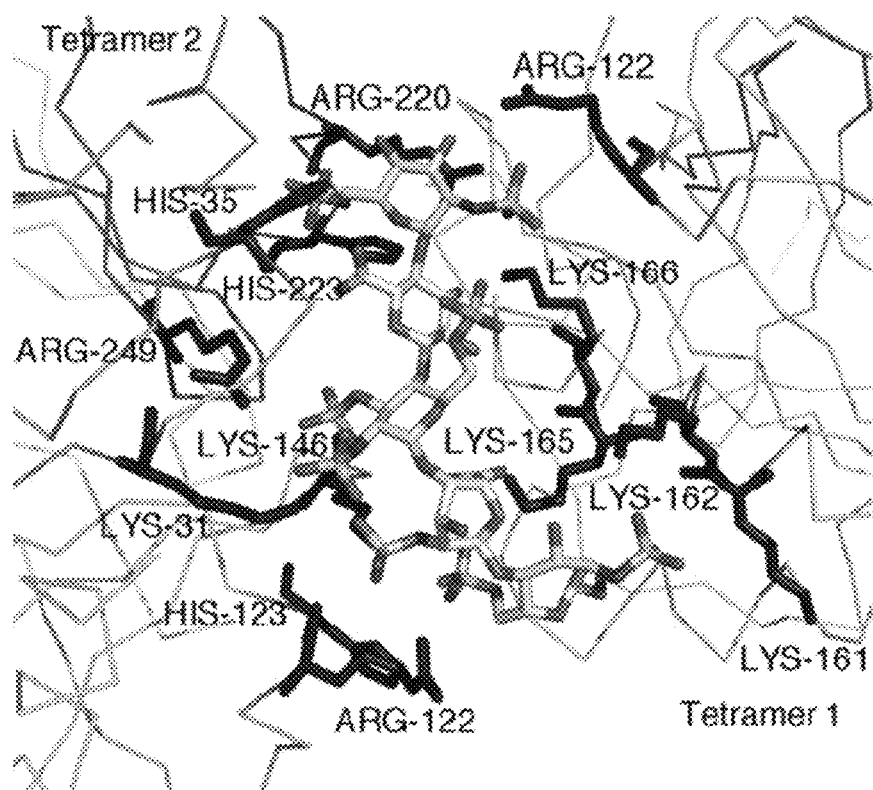

The PF4 tetramer displays a pseudosymmetry characterized by an 'open' end and a 'closed' end that can be defined by the intra-chain distances between amino acids E28 and K50. E28 and K50 are approximately 3 Å apart and form stable salt bridge pairs between chain A and chain C. However, the same inter4 chain salt bridge pairs do not form between E28 and K50 in chains B and D, which are about 8 Å apart (FIG. 2). This asymmetry in the PF4 tetramer explains why calculation of its electrostatic potential identifies only two positively charged grooves on the 'closed' side of PF4 tetramer surface to which fondaparinux can bind (FIG. 9D).

PF4 tetramers can be formed between the AB and CD dimers, or between the AC and BD dimers (Zhang 1994). Fondaparinux binds among monomers A, B and C or monomers A, C, and D (FIG. 9B). This interaction stabilizes the AB/CD association and the AC/BD association, thus further stabilizing the PF4 tetramer. We suggest that this stabilization might represent a very early step in the pathogenesis of HIT antigen.

Analysis of the crystal lattice further reveals that fondaparinux not only makes contact with a single PF4 tetramer within the groove formed by three monomers (ABC or ACD), but also at a second site involving the C-terminal helix of the third monomer (B or D). It has been proposed that the HIT antigen develops when charge neutralization by polyanions allows positively charged PF4 tetramers to undergo close approximation (Nguyen 2015; Greinacher 2006). The crystal structure of the PF4/fondaparinux complex provides a more complete atomic understanding of this process. On fondaparinux molecule not only binds within the groove on the surface of one PF4 tetramer, it is also shared with a second symmetry-related tetramer through binding to its C-terminal helix (FIG. 9C). Most of these interactions are between the sulfate groups of fondaparinux and the basic residues in PF4. The finding that two tetramers of PF4 bind to one heparin fragment provides insight into the initiation of ultralarge complex formation.

Figure 9F:
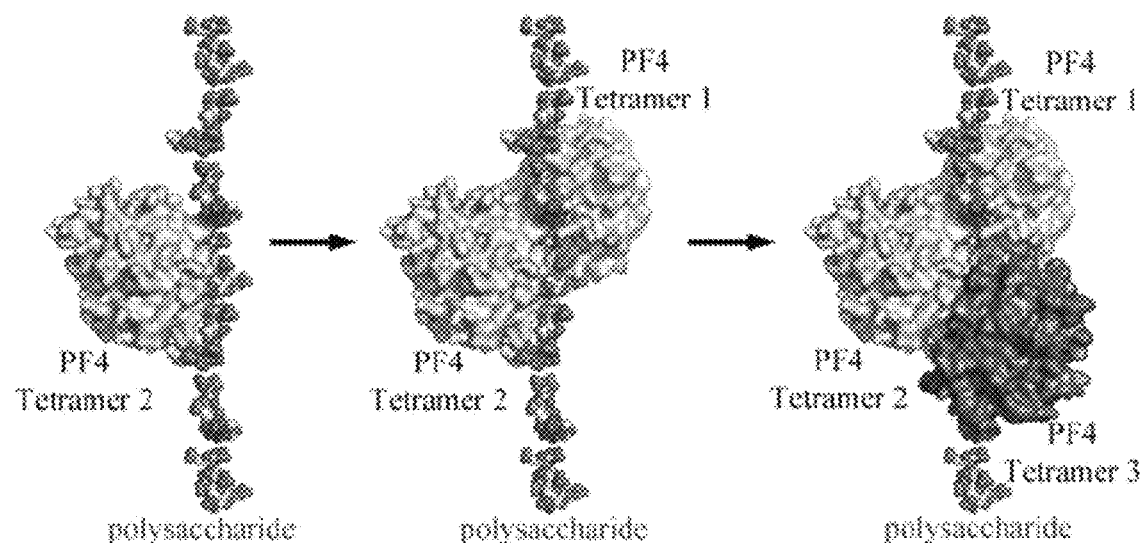

Based on what is observed in the crystal, we propose the following pathway for the formation of the heparin/PF4 complex. Heparin first binds to the groove in one PF4 tetramer. Binding of the first PF4 tetramer imparts a local linearized structure on heparin. This enhances the binding of a second tetramer. Progression of this process eventuates in the formation of the large antigenic complex in which PF4 tetramers cluster around a semi-rigid linear heparin chain (FIG. 9F). Clustering might be required for apposition of sufficient HIT antibodies to induce persistent activation of cellular FcγIIA receptors (Reilly 2001). This model provides structural insight into a recently proposed heparin/PF4 interaction model (Nguyen 2015), and is also consistent with previous NMR (Mayo 1995) and site-directed mutagenesis studies (Ziporen 1998; Li 2002). Moreover, this set of atomic structures extends other studies showing a heparin chain of about 10 saccharides is required to form a stable antigenic complex (Nguyen 2015; Kreimann 2014; Visentin 2001; Greinacher 1995).

Crystal Structure of PF4/KKO-Fab: Recognition of the "Open" End of PF4 Tetramer Leads to a Structural Model of the HIT Pathogenic Ternary Complex.

Figure 10A:
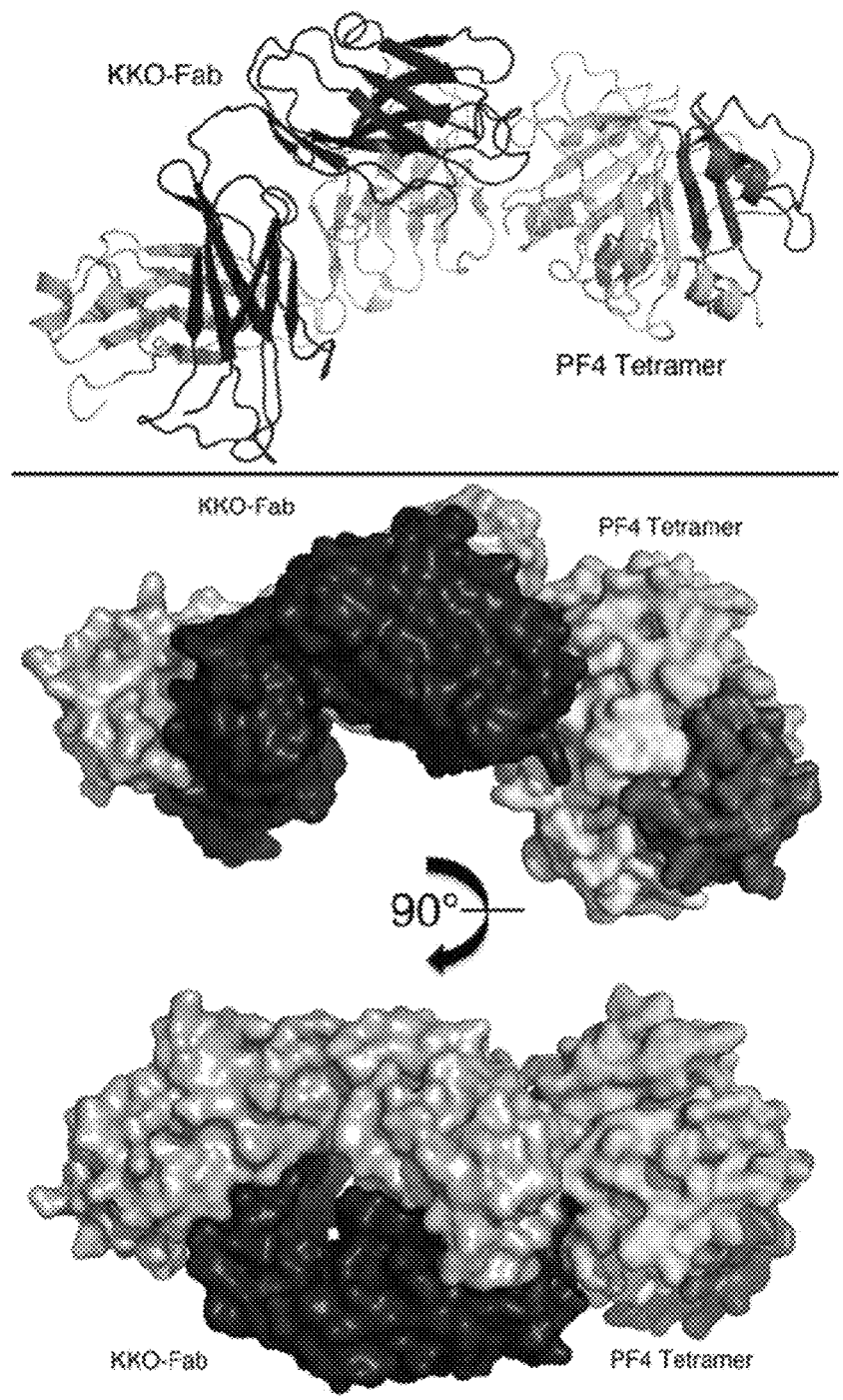
Figure 10D:
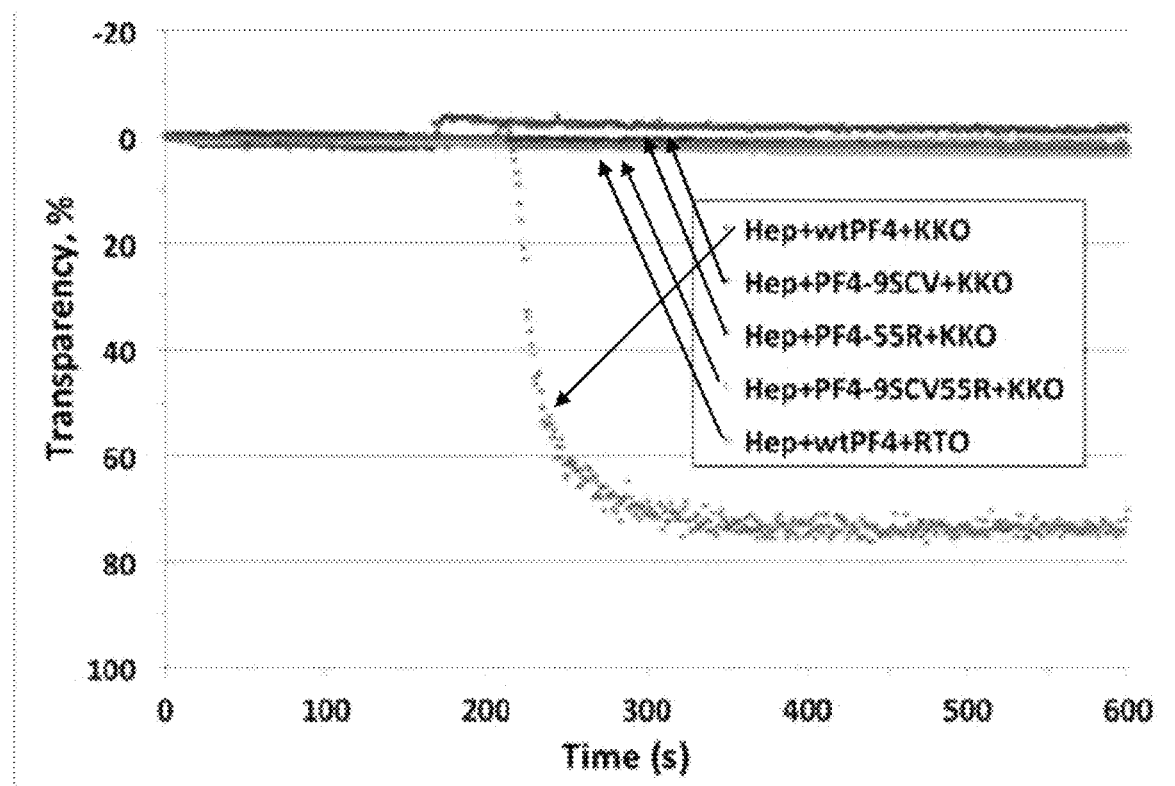

To understand the structural basis for the formation of pathogenic immune complexes, we next solved the crystal structure of human PF4 complexed with the Fab fragment of the monoclonal antibody KKO (FIG. 10A, Table 1 for statistics). KKO recapitulates the salient features of HIT in a mouse model in vivo and competes with human platelet activating anti-PF4/heparin antibodies in vitro (Cuker 2013; Reilly 2001). The KKO-Fab fragment binds to the PF4 tetramer by making contacts with three monomers (for example, chains A, B and D within one PF4 tetramer, FIG. 10A, surface representations; FIG. 10B, detail of KKO epitope on the PF4 tetramer surface). This structure provides strong support for the concept that formation of the tetramer is required for optimal binding of KKO (Amiral 1995).

KKO does not bind to murine (m) PF4 complexed with heparin. Therefore, we compared the sequence of human (h) PF4 with mPF4, and made structure based mutants based on the proposed contact sites identified in the co-crystal (FIG. 3). Mutations in the putative KKO epitope essentially abolished binding of the HIT antibody KKO to these variant PF4s by ELISA (FIG. 10C) and did not support heparin/KKO-induced platelet activation as measured by light transmission aggregometry in contrast to wild-type PF4 (Arepally 2000).

Figure 4:
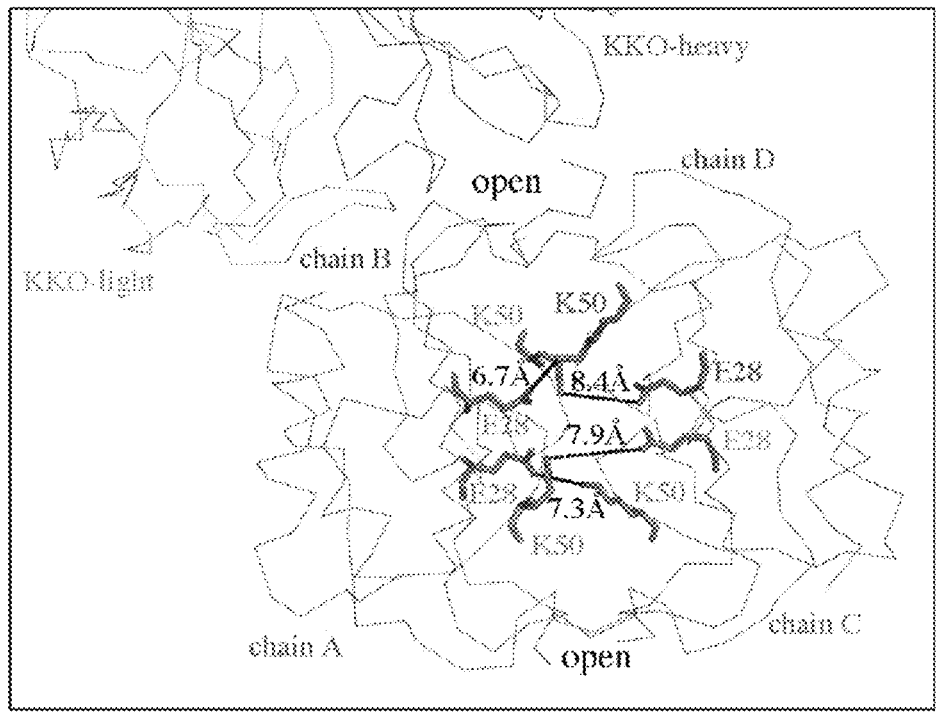
FIG. 4. KKO recognize the surface of the 'open' end on the PF4 in the KKOFab/PF4 complex crystal. Measurement of the E28 to K50 distances (salt bridges exist between chain A and chain C, not between chain B and chain D, in the asymmetric tetramer, FIG. 2) reveals that PF4 in the KKOFab/PF4 complex adopts a symmetric 'open'-'open' conformation. This finding provides evidence that the HIT antibody KKO recognizes the molecular surface of the 'open' end on a PF4 tetramer, which is exposed after the stabilization of the tetramer structure by a heparin.
Figure 10E:
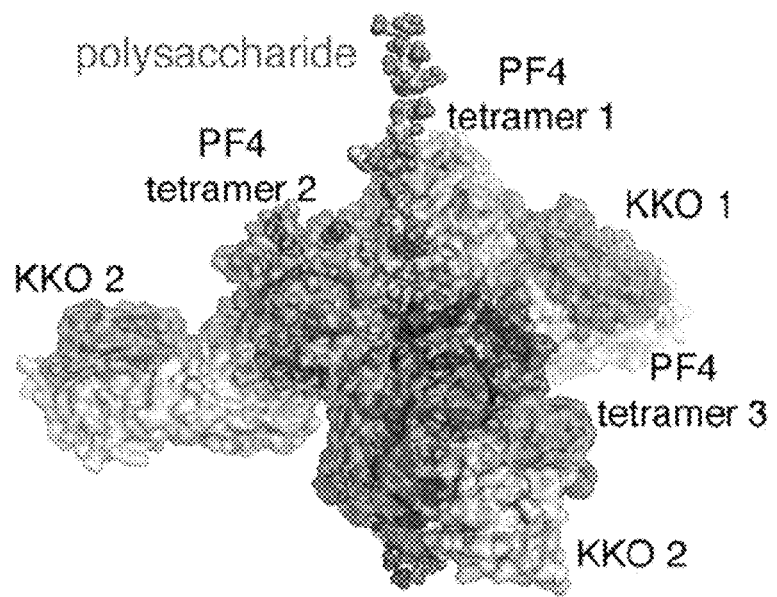

Further analysis revealed that PF4 within the PF4/KKO-Fab complex adopts a symmetric tetrameric structure, which is an 'open'-'open', possibly intermediate, conformation (FIG. 4). This result enabled us to superimpose the PF4/KKO_Fab complex onto the PF4/heparin complex model (FIG. 9F) to build a structural model of the KKO-Fab/PF4/heparin ternary complex. In this model, the polysaccharide binds to the 'closed' end of PF4, stabilizing the PF4 tetramer, which orients the 'open' end for recognition by KKO. In this way, fondaparinux and HIT-like antibody collaborate to "stabilize" the ternary complex (FIG. 10E).

These structures provide the first atomic level description of the pathological complex that might occur in HIT. The model might also help to explain why fondaparinux, a short fragment of heparin, which is antigenic, only rarely causes HIT. Although the protein-GAG interactions can in theory be propagated to additional PF4 tetramers and fondaparinux molecules, we propose that covalent bonding between pentasaccharide units in longer heparins markedly increases the stability of the holo-complex. Consequently, the more "stable" complex becomes more antigenic by enhancing antibody avidity.

Crystal Structure of PF4/RTO-Fab: A Non-Pathogenic Antibody Recognizes the PF4 Monomer RTO is an anti-PF4 antibody that possesses the same isotype as KKO, but does not cause HIT in vivo (Arepally 2000; Rauova 2006). In contrast to KKO, binding of RTO to hPF4 is not enhanced by heparin (Arepally 2000). RTO and KKO also do not compete for binding to hPF4 by ELISA (Sachais 2012). However, KKO and RTO display the same Bmax when measured by ELISA, and is thus illustrative of the difficulty in distinguishing human pathogenic and non-pathogenic antibodies using contemporary bulk equilibrium assays (Sachais 2012). The reason why RTO does not cause HIT was revealed through atomic analyses.

Figure 5:
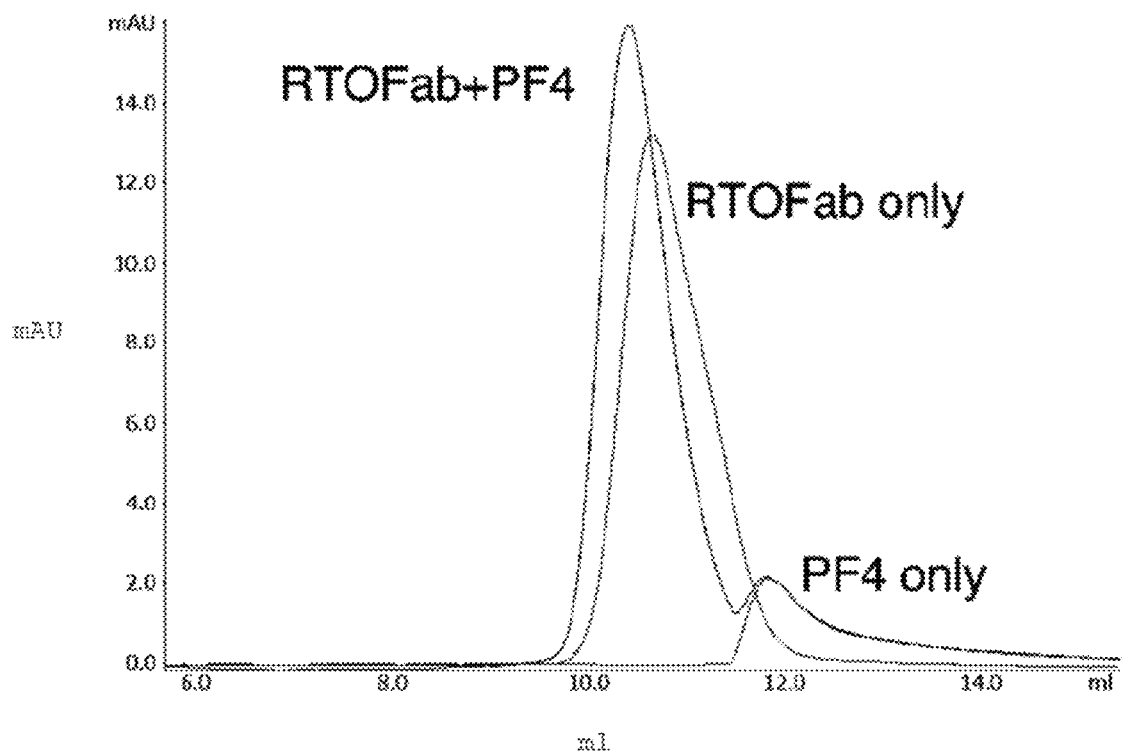
FIG. 5. FPLC profiles of the RTO-Fab/PF4 Complex. Gel filtration profiles of wild type PF4 only, RTOFab only and RTOFab/PF4 complex on a Superdex 75 (GE Healthcare) column. The Superdex 75 column was calibrated using standard proteins and then molecular weight of each peak was determined. The difference between the molecular weight of the RTOFab/PF4 complex peak and that of the RTOFab only peak is about 7,000 dalton, which corresponds to the molecular weight of a PF4 monomer.
Figures 11A, 11B:
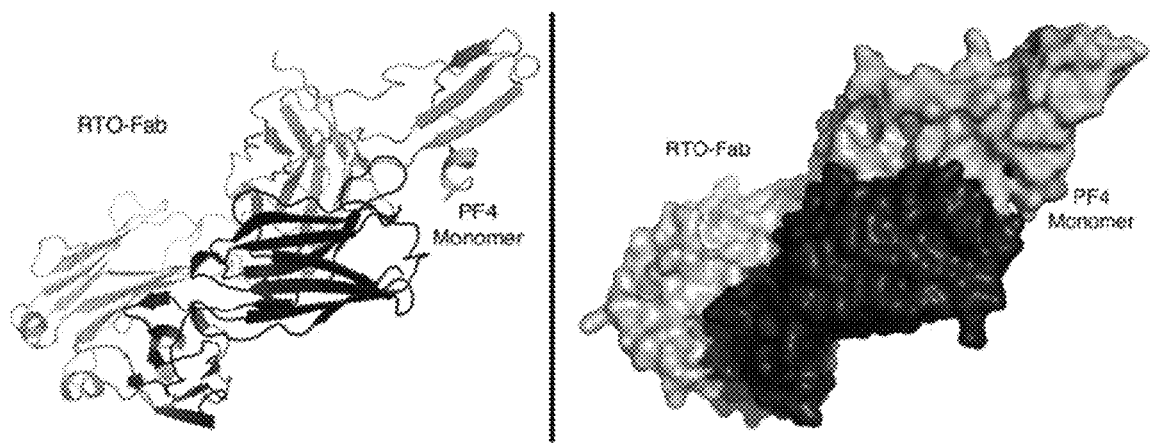
FIG. 11A, FIG. 11B, FIG. 11C, and FIG. 11D. Crystal structure of PF4/RTO-Fab.

To help understand the difference between the impacts of these two antibodies, we next solved the crystal structure of the RTO-Fab in complex with hPF4 (FIG. 11A, Table 1 for statistics). Unexpectedly, RTO-Fab binds only to the PF4 monomer. This was affirmed by a change in the migration of PF4 monomer, but not PF4 tetramer, upon addition of RTO-Fab assessed by FPLC (FIG. 5).

Figure 11C:
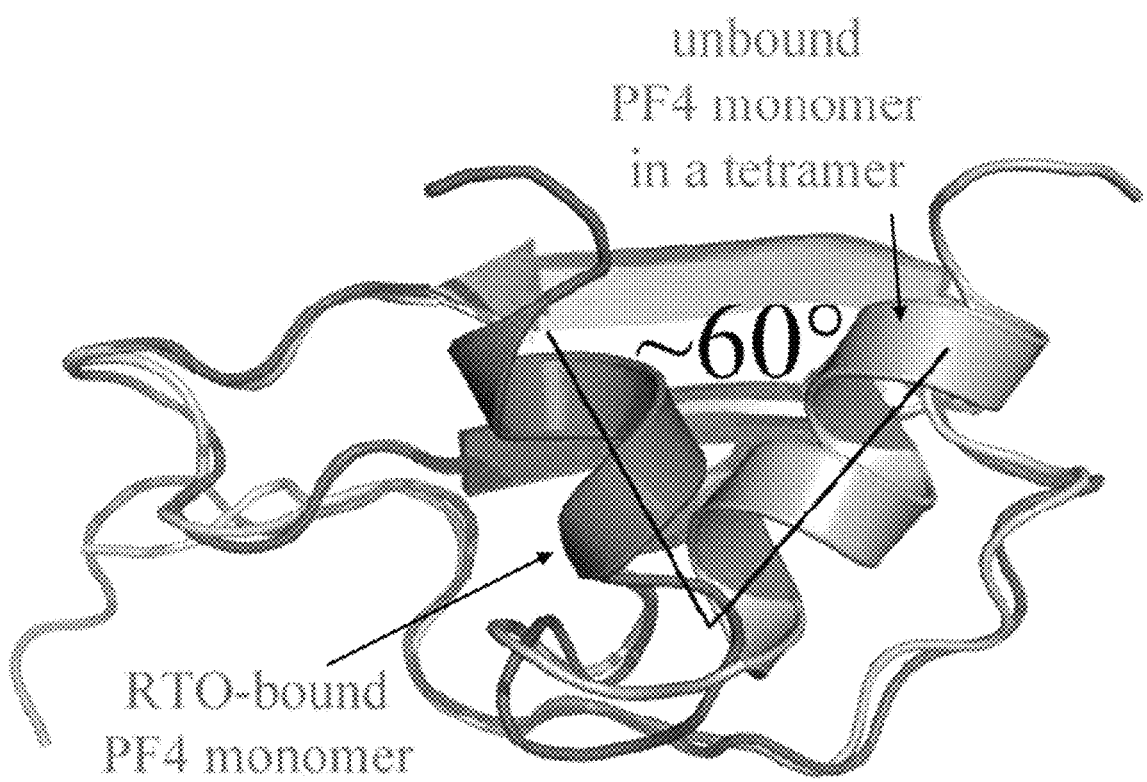
Figure 11D:
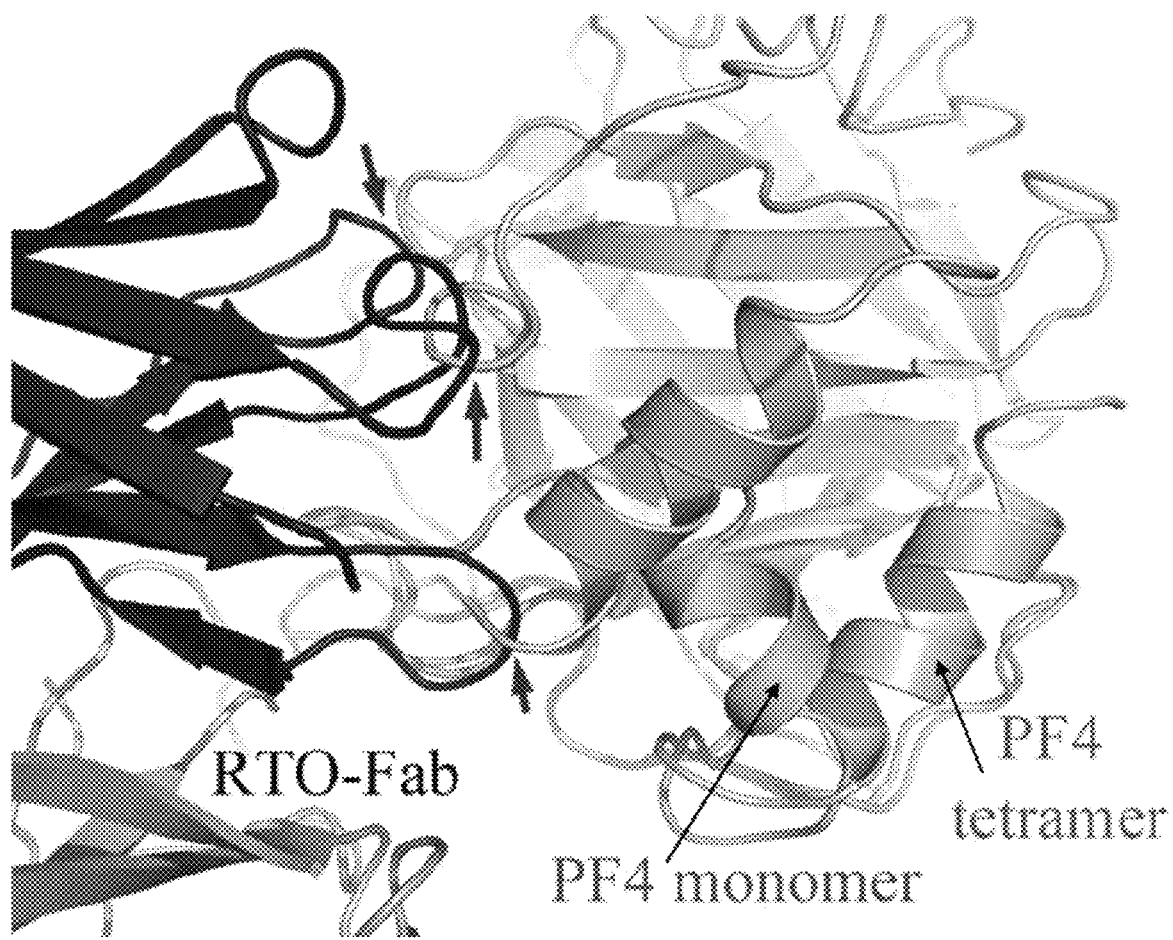

Also unexpectedly, the RTO epitope on PF4 overlapped considerably with the KKO epitope (compare FIG. 11B with FIG. 10B, FIG. 6). In the structure of the RTO-Fab/PF4 complex, the C-terminal helices still pack against the 3-sheet domain. However, the orientation of the C-terminal helices shifts approximately 60 degrees relative to the 3-sheet core domain (FIG. 11C). Superimposition of the PF4 asymmetric tetramer onto the RTO-Fab/PF4 complex reveals that RTO binds between monomer A and monomer B and prevents the formation of the AB dimer, and thereby prevents formation of the tetramer (formation of an AC dimer is still theoretically possible) (FIG. 11D). Together, these structural data lead us to propose that tetramerization of PF4, which is required to form the HIT antigen, would be disrupted by the non-HIT antibody RTO.

RTO Impedes PF4 from Forming Tetramers and Thereby Prevents KKO Induced Platelet Activation: Implications for Clinical Management.

Figure 12A:
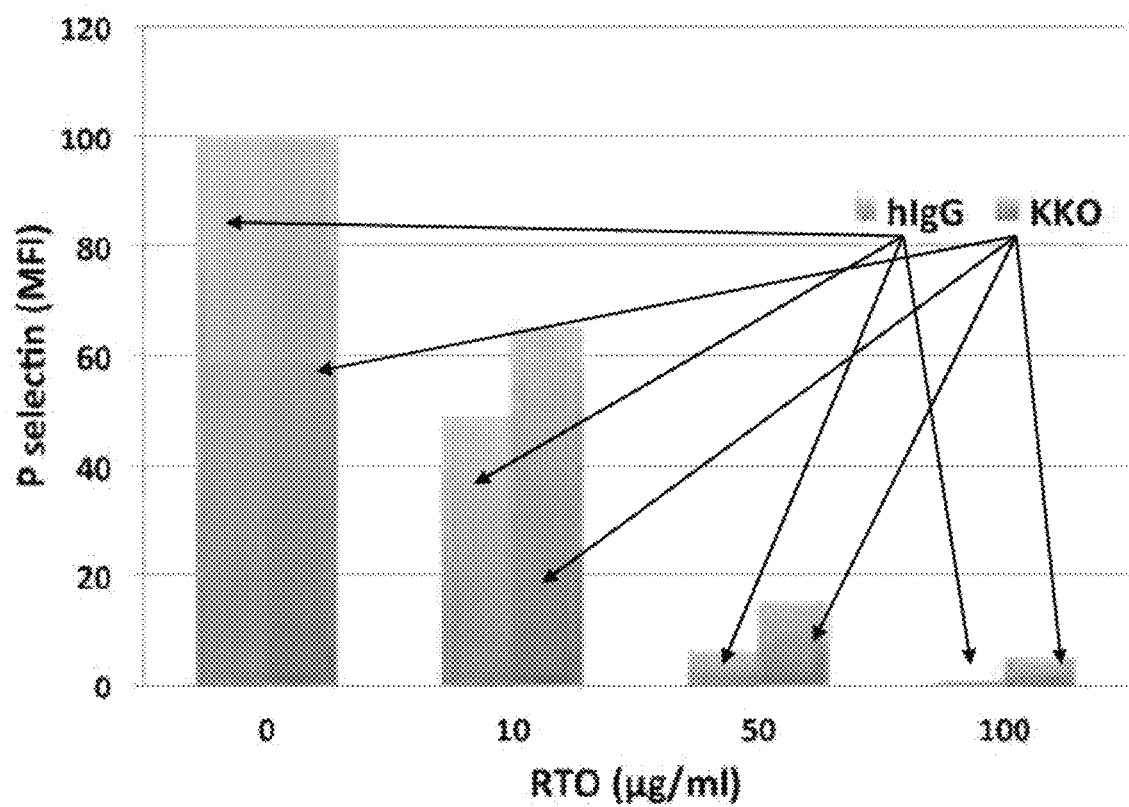
FIG. 12A, FIG. 12B, FIG. 12C, and FIG. 12D. RTO prevents KKO-induced platelet activation and platelet aggregation in vitro and thrombosis in vivo.
Figure 12B:
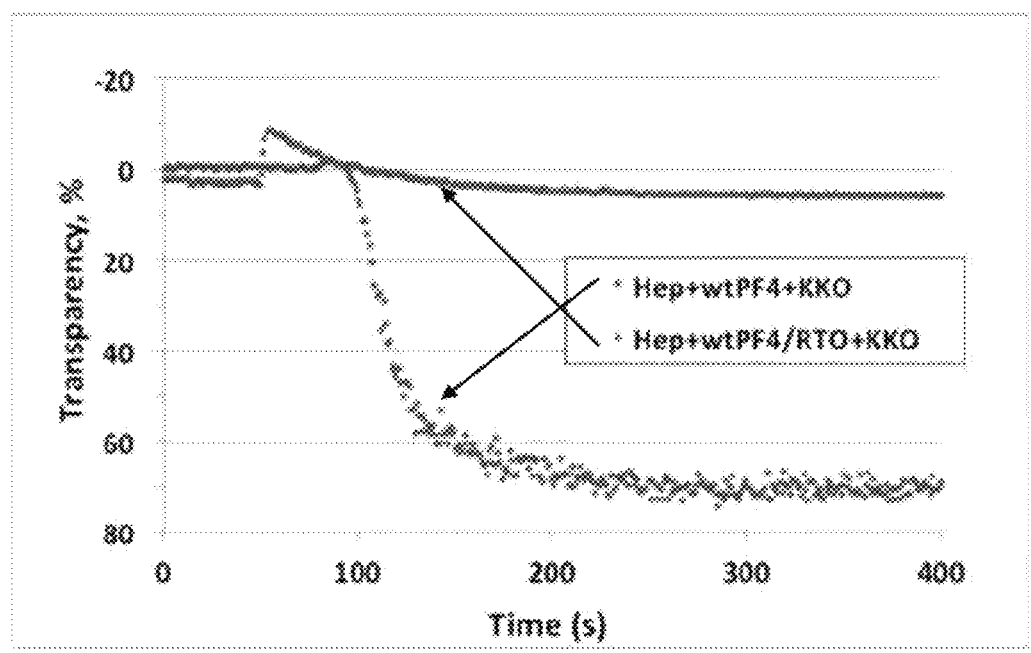

Based on the knowledge that PF4 tetramers exist in equilibrium with monomers and dimers, and with even higher ordered complexes when heparin is present, we predicted that RTO might prevent or disrupt tetramer formation and thereby prevent KKO-induced platelet activation in the presence of heparin. Indeed, RTO inhibited the activation of platelets by KKO and human HIT IgG in the presence of heparin in a dose-dependent manner, as assessed by expression of P-selectin on flow cytometry (FIG. 12A). Preincubation of PF4 with RTO also inhibited KKO-induced platelet aggregation (FIG. 12B).

Figure 12C:
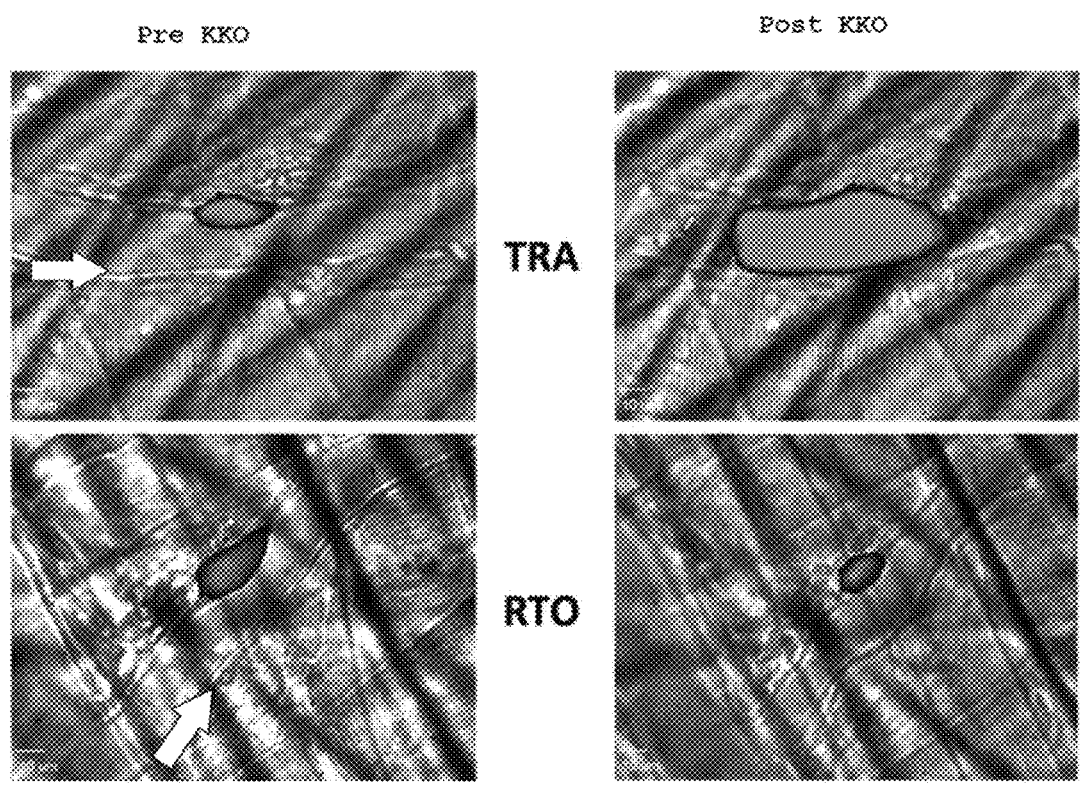
Figure 12D:
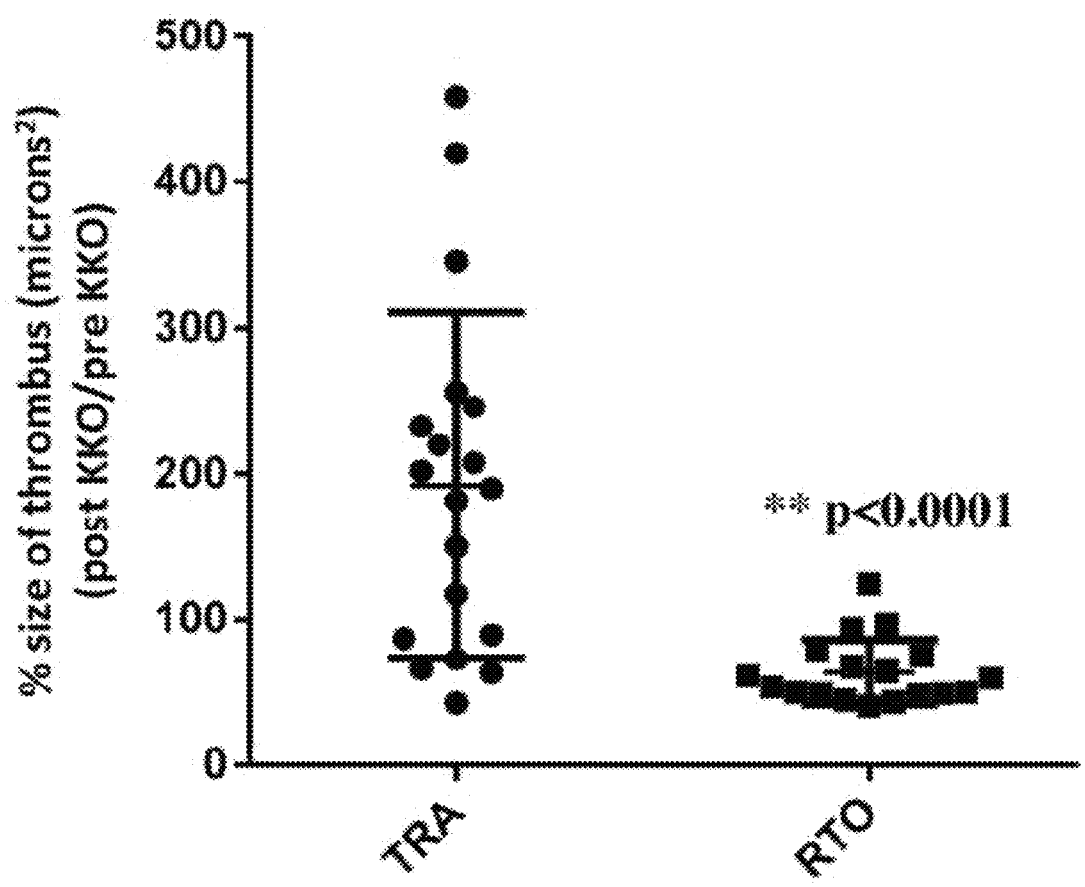
Figure 13:
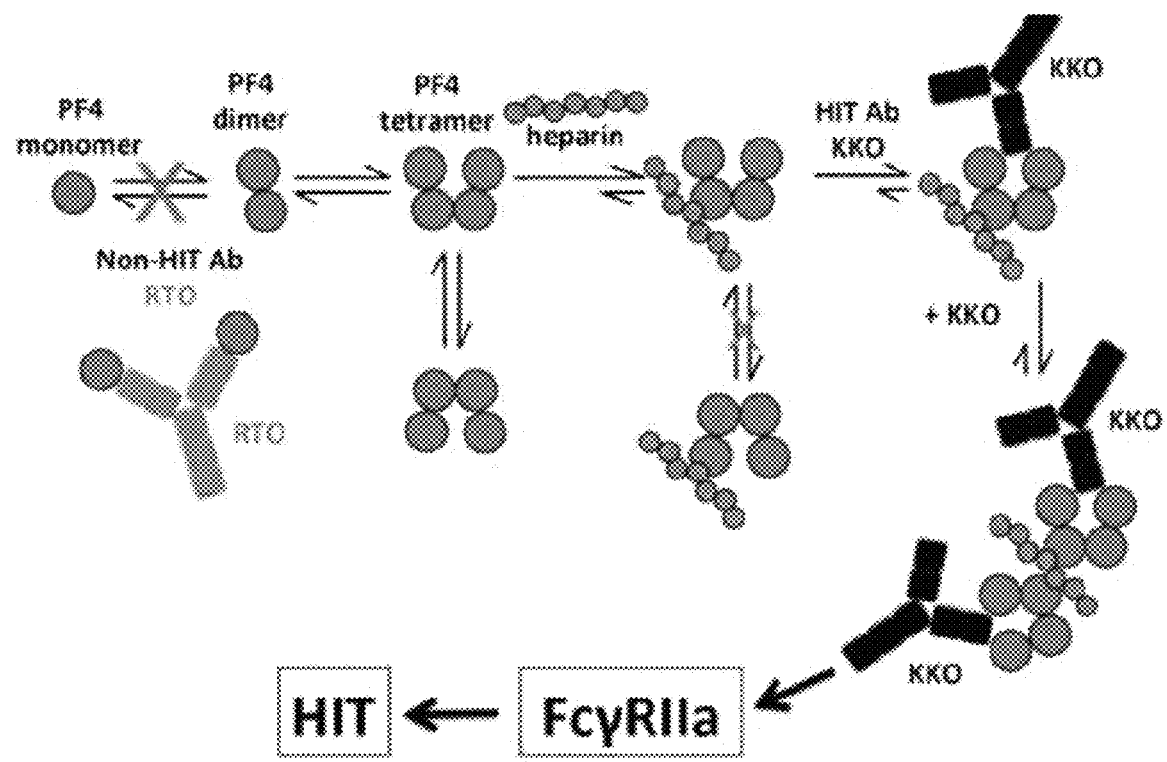
FIG. 13. A cartoon summarizing a model of the pathogenesis of heparin-induced thrombocytopenia and the use of RTO as an inhibitor. PF4 molecules (larger circles) exist in an equilibrium among monomers, dimers and tetramers. Upon binding to heparin (smaller circles), the configuration of the tetramer is stabilized. As a result, the open end of the PF4 tetramer is oriented and recognized by HIT-antibody KKO (black). KKO in turn fosters PF4 oligomerization and works collaboratively with heparin to stabilize the ternary complex. The net result is the generation of stable ultralarge immune complexes capable of sustained activation of Fcγ receptors on platelets and monocytes which consequently leads to HIT. The non-HIT isotype-matched antibody RTO (labelled, lighter gray) binds to PF4 monomers, prevents PF4 oligomerization, prevents formation of ultralarge immune complexes and as a result may prevent HIT. The cartoon assumes heparin is composed of about 7 structures similar to fondaparinux.
Figures 14A, 14B:
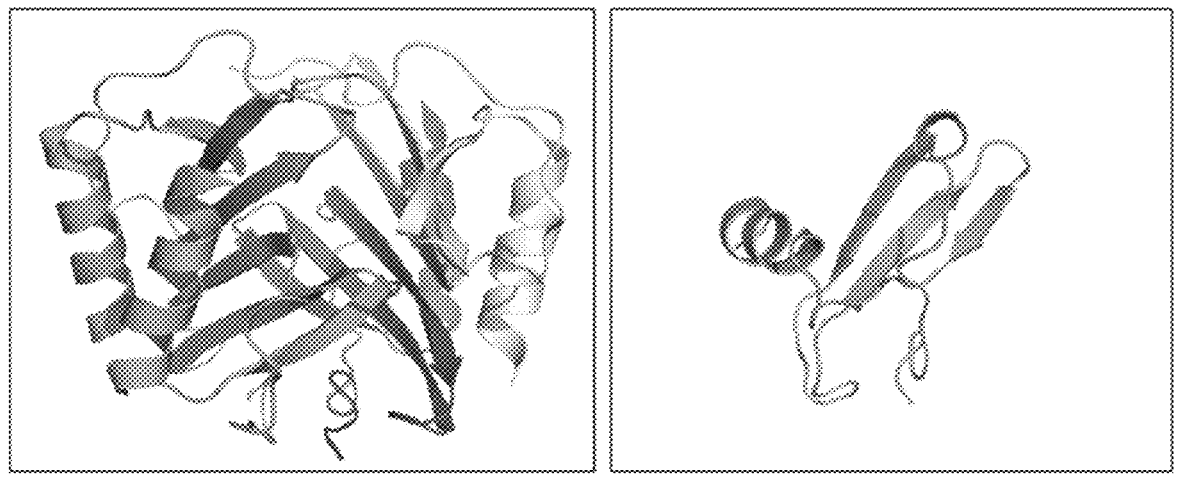
FIG. 14A and FIG. 14B.
Figure 15:
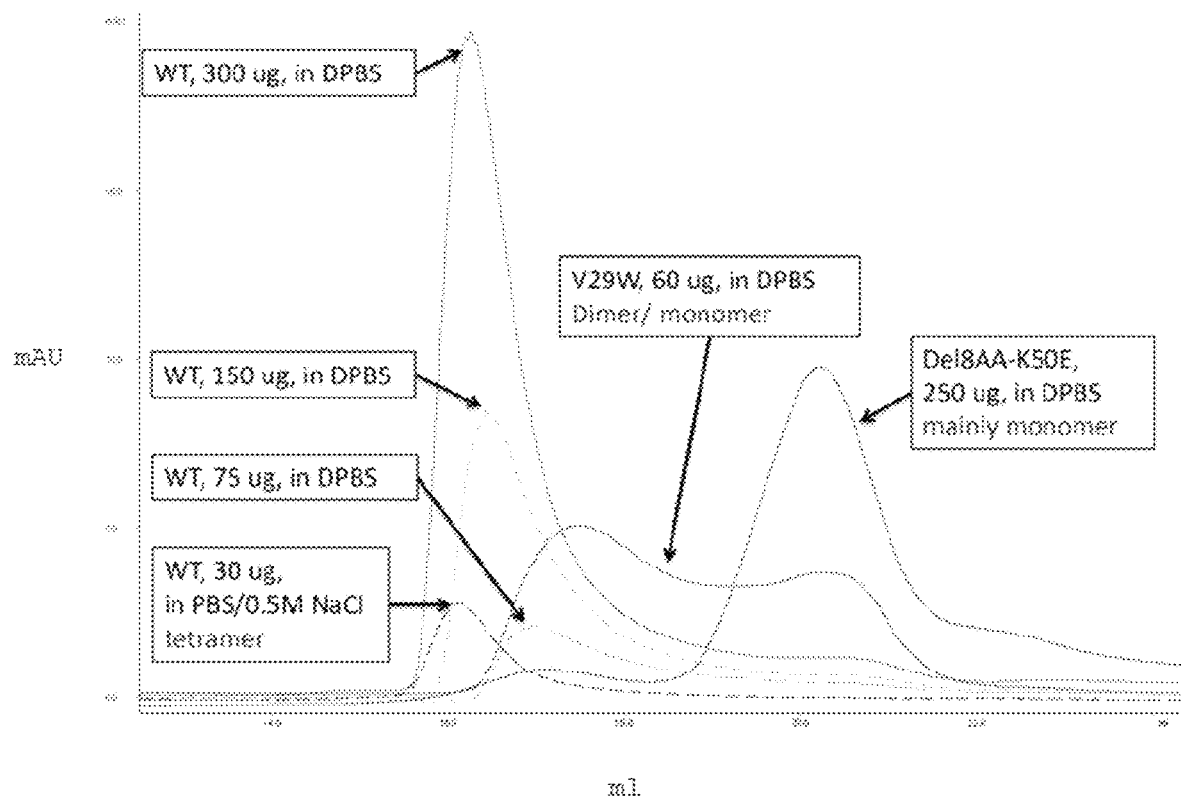
FIG. 15. FPLC profiles of wild type PF4 in DPBS, PBS/0.5M NaCl, PF4 mutant V29W, and PF4 mutant Del8AA-K50E are shown. A concentration-dependent monomer-dimer-tetramer equilibrium can be observed for wild type PF4 in DPBS. The retention time of PF4 mutant V29W corresponds to a dimer/monomer mixture. And the peak for PF4 mutant Del8AA-K50E demonstrates that the mutant Del8AA-K50E mainly exists as monomer in DPBS.
Figure 16:
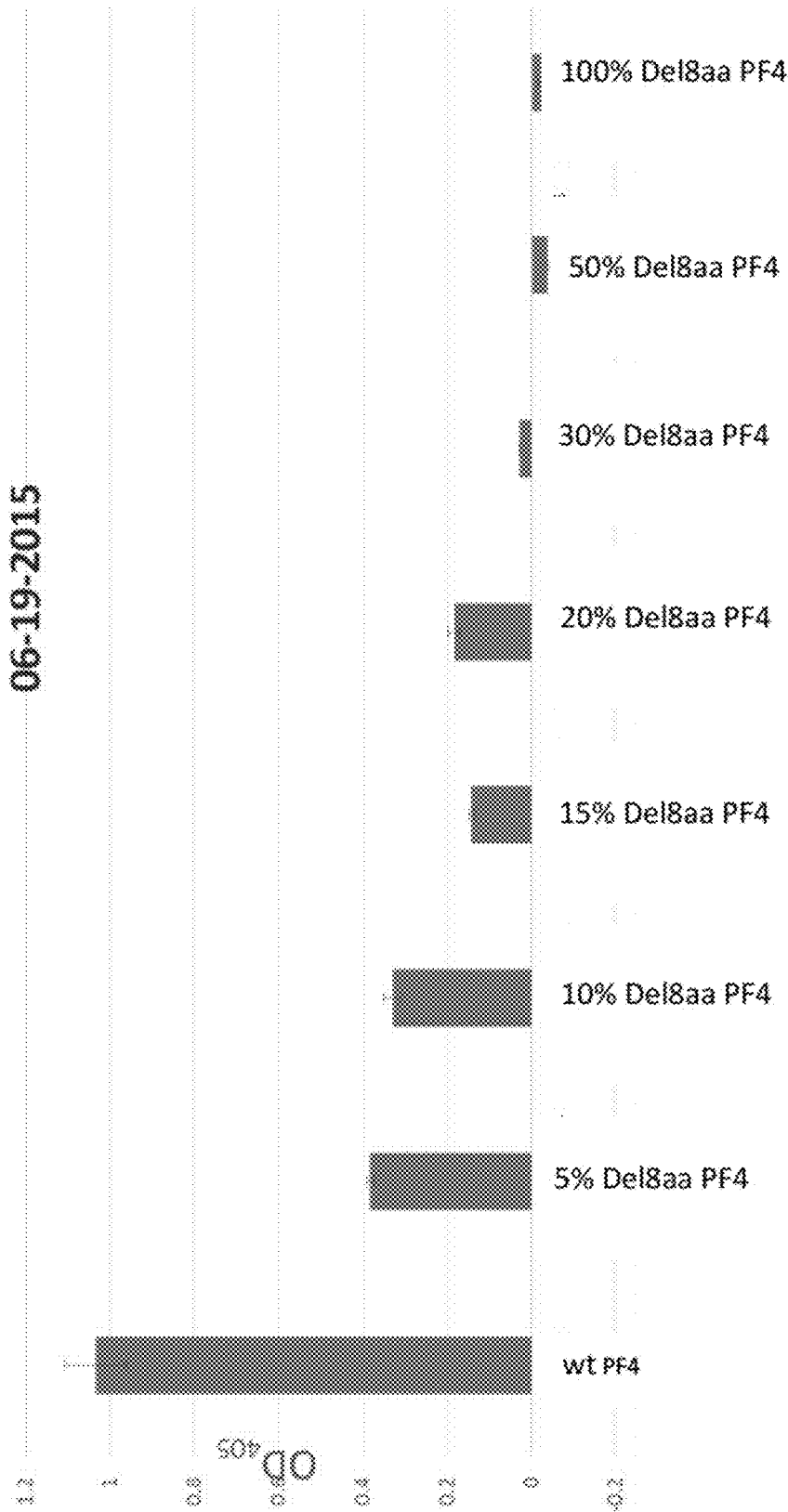
FIG. 16 and FIG. 17. PF4 and PF4 mutants were expressed in S2 insect cells and purified by heparin affinity column. The mixtures of wt PF4 and Delta 8AA PF4 were at 5 ug/ml total, with percentage of Delta 8AA PF4 in the mixture increasing from 0 to 100%. The wt PF4 and Delta 8AA PF4 were pre-incubated together for 30 min and then heparin at 0.1 u/ml (FIG. 16) or no heparin (FIG. 17) was added to the mixture. The mixtures were loaded onto ELISA plate wells overnight. The next day, KKO ELISA was performed. Data shows even 5% of Delta 8AA PF4 in the mixture is sufficient to inhibit KKO binding essentially.
Figure 17:
Figure 18A:
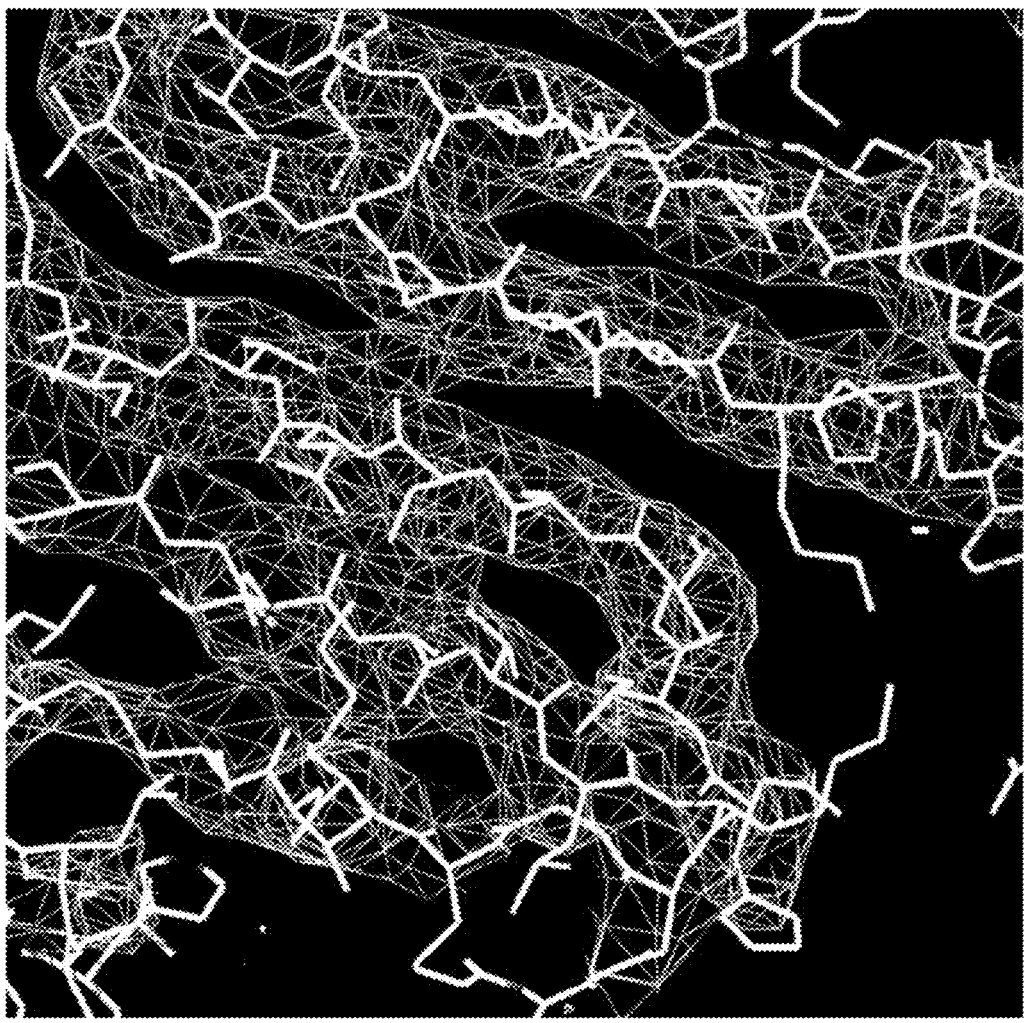
FIG. 18A and FIG. 18B. Images of a portion of the 2Fo-Fc electron density map (at 1.5a contour level) for the KKO-Fab/PF4 tetramer complex (FIG. 18A) and the 2Fo-Fc electron density map (at 1.3a contour level) for the RTO-Fab/PF4 monomer complex (FIG. 18B).
Figure 18B:
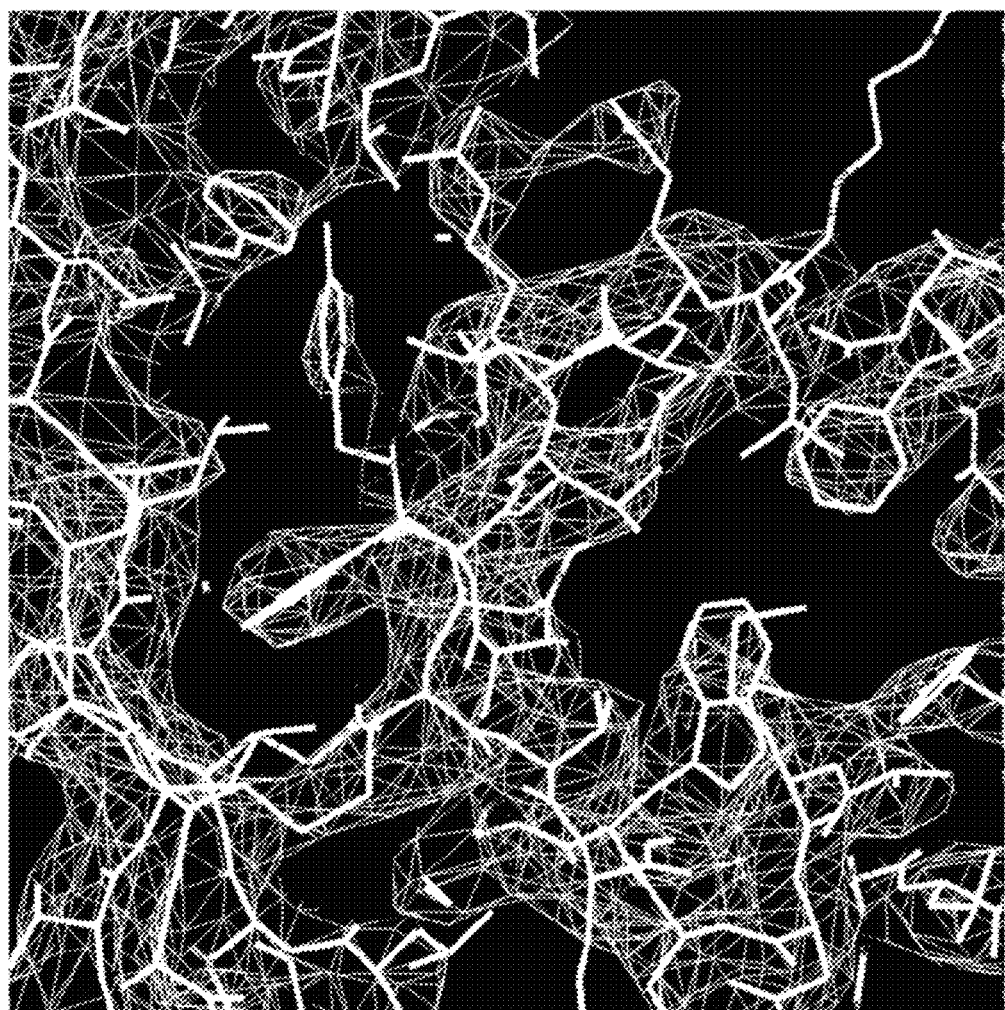

Moreover, RTO completely inhibited KKO-induced progression of thrombosis in a laser microvascular injury model in mouse PF4−/−/human PF4+/+/human FcRγIIA+ mice 26 (FIG. 12C and FIG. 12D). These data indicate that the non-HIT antibody RTO, when engineered and humanized, could provide a template for the development of non-anticoagulant intervention in HIT.

Discussion

It is uncertain how heparin or an endogenous glycosaminoglycan converts a normal host protein, PF4, into an "autoantigen". The crystallographic data provide insight into the multistep process of neoantigen formation at the atomic level. We report the first crystal structure of the PF4 monomer, here in complex with the Fab fragment of an anti-PF4 antibody RTO, which affirms that PF4 exists in solution as an equilibrium among monomers, dimers, and tetramers (Mayo 1989). In the monomeric state, the N-terminal amino acids of PF4 adopt a flexible extended conformation and the C-terminal helices swing around atop the 3-sheet core domain. In contrast, in the tetrameric state the individual monomers undergo a marked conformational change. The C-terminal helices of the PF4 monomers are all re-orientated and re-aligned and the N-termini of the monomers form antiparallel 3-sheet-like structures. The repulsive forces between the positively charged C-terminal helices of monomer A and monomer B in the AB dimer (and similarly between monomer C and monomer D in the CD dimer) might induce thermal instability in the tetramer (Nesmelova 2008). Heparin binds among PF4 monomers and also bridges PF4 tetramers, which helps overcome this instability and leads to the formation of stable individual tetramers, a fundamental first step in the expression of the neoantigen in HIT.

The data described herein also indicates that the asymmetry of the fondaparinux-bound PF4 tetramer, which has an "open" end and a "closed" end, plays an important role in forming the pathogenic antigenic complex. Based on these findings, we propose that heparin or a GAG fragment stabilizes the PF4 tetramer by clamping the monomers together through the "closed" end, orienting the "open" end in the asymmetric PF4 tetramer that comprises the binding site for KKO. Thus, in the absence of heparin, the KKO binding site on the tetramer is nonexistent or incompletely expressed on the PF4 monomer and dimer and is only transiently expressed and unstable on tetramers that form at high concentrations of PF4. Thus, stabilization of the tetramer by heparin leading to a more stable orientation of an epitope on each PF4 tetramer, compared with the transient and more random orientation of the epitope in the absence of heparin, is a second defining step in the process of generating the HIT neoantigen. Heparins or GAGs of sufficient lengths can then cluster several PF4 tetramers further enhancing stability, which helps to explain why PF4, among heparin binding proteins, is especially antigenic (Sachais 2012; Nguyen 2015). In the third step, HIT-like antibody KKO recognizes the stabilized "open" end of the PF4 tetramers, further promoting formation of the pathogenic ternary complex.

PF4 species are known to participate in coagulation, cell growth and angiogenesis (Lippi 2010; Funatsu 2001; Maione 1990).

PF4 monomers can associate into a tetrameric form as well as dissociate from that tetrameric species. The PF4 tetramer that interacts with heparin a highly sulfated glycosaminoglycan, or oligonucleotides facilitate the expression of an antigenic epitope that can bind antibodies to form a larger complex.

The ability of monomeric PF4 to form stable tetramers can be affected by deletion or amino acid substitutions. In addition while monomeric mutants may still bind heparin, they are not able to form canonical clusters with heparin as wildtype pf4 does.

PF4 which has been altered and can no longer form stable tetramers cannot form antigenic complexes when exposed to heparin, and will not be able to express the complete antigenic epitope that binds pathogenic antibodies.

The studies described herein were performed with fondaparinux because the heterogeneity of clinical heparins and GAGs preclude obtaining structural detail. Therefore, we do not exclude the possibility that low molecular weight or unfractionated heparin might induce additional changes within and between PF4 tetramers (Brandt 2014; Block 2014). Indeed, the structural model described herein predicts that when a GAG longer than about 10 saccharides binds to more than one PF4 tetramer, additional structural changes within the tetramers themselves are quite likely. These structural changes are more likely to occur within the inner surface of the PF4 tetramers in the cluster along the PF4/heparin binding interface than primarily at the HIT antibody binding epitope, which lies on the outer surface. Therefore, additional studies are needed based on this model, to determine if these additional structural changes in PF4 imparted by longer GAGs directly modulate the contact sites between antibody and antigen.

The A32-A39 loop on the PF4 monomer appears to be highly immunogenic. However, the data described herein suggest that pathogenic and non-pathogenic antibodies that bind to this region differ in how they affect the monomer-dimertetramer equilibrium. Pathogenic antibodies that act like KKO and preferentially recognize the tetrameric species display greater avidity in the presence of heparin, which approximates epitopes, and in turn the bound antibody fosters oligomerization (Sachais 2012). Binding of KKO may also shift the equilibrium from heparin wrapping around the PF4 species suggested in a previous model 13 by forcing it into a more stable linear conformation (Nguyen 2015). The net result would be the generation of stable ultralarge immune complexes (Rauova 2005) capable of sustained activation of FcγIIA receptors on platelets and monocytes (Reilly 2001; Rauova 2010). In contrast, anti-PF4 antibodies that preferentially recognize monomers in the manner of RTO are readily detected by contemporary ELISAs, but they do not generate large immune complexes that cause disease. Indeed, anti-PF4 antibodies that act like RTO may actually compete with pathogenic antibodies by preventing or disrupting tetramer formation and thereby limit formation of larger immune complexes as depicted in FIG. 5. These data provide a new mechanistic model for the development of a human autoimmune disease, in which a host-protein PF4 complexed with host GAGs assumes diverse oligomeric conformations that differentially bind autoreactive antibodies leading to diverse clinical outcomes.

The studies described herein might have implications for the diagnosis of HIT. The two prototypic antibodies we studied, RTO and KKO, bind comparably to PF4/heparin on ELISA plates at equilibrium and do not compete with each other for binding in this format (Sachai 2012; Cuker 2013). This suggests that ELISA wells might contain PF4 in diverse conformations ranging from monomer through tetramer and likely higher ordered complexes. Studies are in progress to determine if ELISA formats based on more homogenous populations of PF4 complexes and/or mutant PF4 monomers will reduce detection of non-pathogenic, potentially "blocking", anti-PF4 antibodies. Additional studies will also be needed to determine if differences in the ratio of pathogenic and "blocking" antibodies might contribute to the likelihood of developing HIT.

The studies described herein might also have implications for therapy. Anticoagulants are the standard treatment for HIT, but their efficacy is incomplete and dosing is limited by the risk of bleeding (Cuker 2012; Kang 2015) Our data indicate that RTO binds to PF4 monomers and preempts assembly of stable tetramers and, as a result, inhibits KKO (and human HIT IgG) induced platelet activation and aggregation in vitro and, importantly, progression of antibody-induced thrombosis in vivo. It is likely release of PF4 and formation of antigenic complexes extends beyond diagnosis and introduction of a direct thrombin inhibitor, as does the risk of recurrent thromboembolic complications. The inhibitory effects of RTO indicate that tetramerization of PF4 is targetable and that this antibody may provide a structural basis for developing rational non-anticoagulant HIT-specific intervention for this serious and common iatrogenic disorder.

It has been difficult to differentiate between the impact of changes within the secondary structure of individual PF4 tetramers that affect antibody affinity and effects on tetramer oligomerization that enhance avidity, because both contribute to antibody binding measured in ELISA wells that likely contain various conformations of PF4. Our use of Fab fragments that are unable (or show little ability) to oligomerize PF4 tetramers, and fondaparinux, which is antigenic but rarely pathogenic because it has a low capacity to form higher ordered structures, provided an opportunity to delineate the evolution of the antigenic site within the PF4 tetramer itself.

Nevertheless, we wish to emphasize that our studies also have potential limitations. First, the necessity of using fondaparinux as the GAG precluded possible additional relevant changes within PF4 induced by longer heparin molecules that are more likely to induce HIT. Nor can we assess the intramolecular and intermolecular effects on PF4 imparted by the complex array of cellular GAGs. Second, although most HIT antibodies compete with KKO for binding, our data do not preclude additional contact sites between polyspecific human antibodies and PF4/heparin. Third, crystallography and other biophysical approaches using purified proteins inherently explore atomic interactions in a single stable structure favored by the experimental conditions. Thus, the full range of dynamic changes in (super) oligomerization that occur during the evolution of the disease may not be captured. Thus, our study only provides a model that may help to explain sentinel events through which GAGs may induce binding of autoantibodies to a normal host protein. Fourth, in our experiments, RTO was added prior to KKO. The dynamics of RTO binding to PF4 might well be different when heparin and a pathogenic HIT antibody are already present. We are currently investigating the effect of RTO on thrombus growth in vivo following exposure to KKO.

Methods

Expression and Purification of Human PF4 and Antibodies.

Wild type (WT) hPF4 and hPF4 mutants in plasmid pMT/BiP/V5-His (Invitrogen Corp., Carlsbad CA), were expressed using the *Drosophila* Expression System (Invitrogen), purified, and characterized as described (Sachais 2012). Briefly, the protein was collected in serum-free medium Insect-Xpress (Lonza, Walkersville, MD) and isolated by affinity chromatography using a HiTrap Heparin HP column (GE Healthcare) on an AKTA Purifier (GE Healthcare) at 4° C. and eluted at 1.8 M NaCl (wtPF4) using a linear gradient. Fractions containing purified PF4 detected by silver staining of 12% polyacrylamide gels (SDS-PAGE) were pooled, concentrated and buffer exchanged into 50 mM HEPES, 0.5 M NaCl, pH ~7.2 using an Amicon Ultra filter (3000 molecular weight cut-off, Millipore). Protein was quantified using a BCA assay (Pierce). To obtain the PF4 mutants, PCR with corresponding primers (Table 2) was performed on pMT/BiP/V5/HisA-uPA plasmid under conditions recommended by The QuikChange Site-Directed Mutagenesis Kit manual (Stratagene, La Jolla, CA). The resulting plasmids were sequenced to confirm the mutation.

TABLE 2

Sequences of primers that were used to generate PF4 mutants.

| Primers | Sequences |
| --- | --- |
| 9SCV | GAA GAT GGC GAC CTG AGC TGC GTG TGT GTG AAG ACC (SEQ ID NO: 17) |
| 9SCV-anti | GGT CTT CAC ACA CAC GCA GCT CAG GTC GCC ATC TTC (SEQ ID NO: 18) |
| 55R | AGG AAA ATT TGC TTG GAC CGC CAA GCT CCG CTG TAC (SEQ ID NO: 19) |
| 55R-anti | GTA CAG CGG AGC TTG GCG GTC CAA GCA AAT TTT CCT (SEQ ID NO: 20) |

The murine anti-human PF4 IgG2bK monoclonal antibodies KKO and RTO have previously been described (Arepally 2000). The IgGs were purified from conditioned PFHM-II media (Invitrogen) using protein A-agarose (Invitrogen) as recommended by the manufacturer. IgG purity was demonstrated by SDS-PAGE on NuPAGE 4-12% Bis-Tris Gel (Invitrogen). Fab fragments were generated by papain digest using Pierce® Fab Preparation Kit (Thermo Scientific, Rockford, IL) essentially as recommended by the manufacturer, followed by three rounds of removing of Fc fragments with protein A agarose beads, and extra purification with anti-mouse IgG (Fc-specific) (Sigma M4280) and anti-mouse IgG (Fab-specific) Sigma M4155 antibodies bound to CNBr-activated Sepharose 4 Fast Flow beads (Amersham Biosciences Corp., Piscataway, NJ) as recommended by the manufacturer. KKOFab, RTOFab and PF4 were further purified by size-exclusion column on an AKTA purifier system (GE Healthcare). Human HIT IgG was purified using staph protein agarose (source) from a pheresate obtained from a patient with HIT.

ELISA Assays.

Binding of human IgG was measured essentially as previously described for KKO and RTO antibodies (Sachais 2012). Briefly, Immulon 4 HBX 96-well plates (Thermo Fisher Scientific, Waltham, MA) were coated overnight with either PF4 or PF4 mutant at 5 ug/ml. The plates were incubated for 30 min with either PBS (control) or with 0.5% glutaraldehyde at room temperature, extensively washed and blocked with 1% BSA in PBS. The plates were incubated with human patient IgG samples at experimentally selected concentration of g/ml for 30 min at 37° C. IgG 11 binding was measured as absorbance at 405 nm (A405) after incubation for 30 min at 37° C. with horseradish peroxidase-conjugated ImmunoPure Goat Anti-Human IgG (H+L), HRP Conjugated Product No. 31412 (Pierce. Rockford, IL) diluted 1:10,000 in 1% BSA/PBS. Horseradish peroxidase substrate ABTS was from Roche Applied Science, Penzberg, Germany. Absorbance was measured with a SpectraCount plate reader (Packard BioScience, Waltham, MA).

In Vitro Platelet Activation Mediated by KKO+PF4

Blood for in vitro studies (platelet activation and light transmission aggregometry) was collected after informed consent from healthy, aspirin-free volunteers using a 19-gauge butterfly needle in 129 mM sodium citrate (10:1, vol/vol) under protocols approved by the Institutional Review Board of the University of Pennsylvania and the Children's Hospital of Philadelphia. Whole blood samples were incubated in Ca++/Hepes buffer (2.5 mM CaCl2), 1.25 mM MgCl2, 150 mM NaCl, 10 mM HEPES, pH 7.5) 1/100 v/v in the presence of APC labeled antihCD41 and PE labeled anti-P-selectin, PF4 (10 µg/ml) and the concentrations of RTO MOAb indicated in the figure for 15 min at room temperature. KKO (20 µg/ml) or human HIT IgG (500 µg/mL) was added for 20 min at room temperature, samples were then diluted by adding 400 µL of HBSA/BSA/EDTA buffer and immediately measured by flow cytometry (BD LSRFortessa™). Platelets were gated based on the forward-scatter and CD41 fluorescence parameters, and binding of anti-P-selectin antibodies was quantified as geometric mean fluorescent intensity (MFI).

Light Transmission Aggregometry

Blood was centrifuged for 12 min at 210×g at 25° C. to generate platelet-rich plasma (PRP) and at 900×g for 10 min at 25° C. to produce platelet-poor plasma (PPP). Platelet aggregation was measured in PRP using a dual-channel lumiaggregometer (model 700, Chrono-log Corporation, Havertown, PA) per the manufacturer's instructions. All experiments were completed within 4 hrs of blood collection. PRP (500 l) was pre-warmed for 2 min at 37° C., heparin (Sagent Pharmaceuticals, Schaumburg, IL) was added (final concentration 0.1 U/ml) for 30 sec followed by wild type or mutant rPF4 (final concentration 10 μg/ml) for 30 sec followed by KKO or RTO (100 μ/ml) for up to 10 min. The final volume of added reagents did not exceed 5% of the starting volume of PRP. To examine inhibition of KKO induced platelet aggregation, 100 μg RTO was preincubated with 5 μg PF4 for 15 min at 25° C. Heparin (final concentration 0.1 U/ml) was added to pre-warmed PRP. Thirty seconds later PF4 or PF4/RTO complex was added (final concentrations in PRP 10 μg/ml and 10 μg/ml/200 μg/ml, respectively). KKO (final concentration of 100 μg/ml) was added 30 sec later and aggregation was assessed as above.

Inhibition of KKO-Induced Thrombosis In Vivo.

Transgenic male C57BL mice, lacking mouse PF4 but expressing human PF4 and human FcγRIIA (Reilly 2001) were studied. Mice were matched littermates between 6-10 weeks of age. The cremaster laser injury model (Rauova 2006; Falati 2002) was used to visualize in vivo thrombus formation. After surgical preparation, Alexa 647 (BD Biosciences) labeled mouse CD41-F(ab')2 fragments were infused intravenously to label circulating platelets. Each mouse then received 50 μg/g of either RTO or the IgGK2B isotype control TRA intravenously followed by 7-8 focal arterial injuries. A brightfield and fluorescence snapshot of each injury was taken 15 minutes after the initial injury. KKO was then injected intravenously at a dose of 2.5 μg/g. Fifteen minutes after injection of KKO, a second brightfield and fluorescence snapshot of the same injuries was taken to compare platelet deposition before and after KKO. Image analysis was performed using Slidebook 6 (31 Intelligent Imaging Innovations, Denver, CO). The size of the thrombus was determined by having the software automatically segment the image using Otsu thresholding to remove background and then calculate and export the size of the platelet fluorescence in microns (Phillips 2008). The investigator was not blinded during these studies. All experiments were performed in compliance with the institutional guidelines for the care and handling of experimental animals were approved by the Children's Hospital of Philadelphia Institutional Animal Care and Use Committee.

Statistical Analysis

Statistical analysis of in vivo injuries was performed using Prism 6 (GraphPad, La Jolla, CA). A two-tailed Student's t-test under non-parametric conditions with Mann Whitney correction was performed to assess statistical significance. P values <0.05 were considered significant. There was no randomization of mice. The mice used were selected based on availability. There was no exclusion criteria established prior to experimentation, available healthy mice were selected for use. No tests of normality or power analyses were conducted.

Crystallization and Data Collection

Purified KKOFab (5 mg/ml) and RTOFab (5 mg/ml) were mixed with hPF4 at different ratios and incubated on ice overnight before setting up crystallization trials. The hPF4/fondaparinux complex was prepared by adding 6-fold molar excess fondaparinux (Arixtra, Sanofi-Synthelabo LLC) into purified hPF4 (7 mg/ml); the mixture was incubated on ice in a buffer containing PBS and 0.3 M NaCl.

Crystallizations of hPF4/fondaparinux, KKOFab, hPF4/KKOFab, and hPF4/RTOFab were performed using the hanging-drop vapor diffusion method by mixing the protein and well solution at 1:1 volume ratio at 16° C. Crystallization kits from Hampton Research and Molecular Dimensions were used for initial crystallization trials. Optimized hPF4/fondaparinux complex crystals were obtained in the well solution containing 2% PEG4000, 17% MPD, 0.1 M sodium acetate pH 5.6. hPF4/fondaparinux complex crystals were then directly flashcooled in liquid nitrogen by using the MiTeGen micromounts (MiTeGen, LLC).

Diffraction quality KKOFab crystals were obtained in the well solution containing 14% PEG2000, 0.06 M zinc acetate, 0.1 M sodium cacodylate, pH6.8. KKOFab crystals were transferred into the well solution supplemented with 25% glycerol, soaked for one second, and then flash-cooled in liquid nitrogen. Diffraction quality hPF4/KKOFab crystals were obtained in the well solution containing 7% PEG6000, 0.1 M Tris-HCl, pH 7.8. hPF4/KKOFab complex crystals were flashcooled in liquid nitrogen similarly as KKOFab crystals. hPF4/RTOFab complex crystals were obtained in the well solution containing 0.2 M ammonium sulfate, 0.1 M BIS-TRIS, pH 6.5, 25% w/v Polyethylene glycol 3350. The diffraction quality PF4/RTOFab crystals were optimized by macro-seeding. hPF4/RTOFab complex crystals were transferred into the well solution supplemented with 20% glycerol, soaked for one second, and then flash-cooled in liquid nitrogen.

All crystallographic data sets were collected at 100 K with ADSC CCD detectors. The long-wavelength (A-2.07 Å) sulfur anomalous diffraction data sets for hPF4/fondaparinux complex and hPF4/RTOFab complex were collected at beamline X4A at National Synchrotron Light Source (NSLS) at Brookhaven National Laboratory (Upton, NY USA). Other data sets were collected at NSLS beamlines X6A and X4C at Brookhaven National Laboratory. All diffraction data were processed by using the HKL-2000 package (Otwinowski 1997).

Structure Determination and Refinement.

All structures were solved by molecular replacement. The structure of the hPF4/fondaparinux complex was solved by CCP4 program MOLREP (Winn 2011; Vagin 2010) with AB dimer from the hPF4 structure (PDB ID code:1F9Q) as a search model. The structure of KKOFab was also solved by MOLREP with the Fab structure from the DsbB-Fab complex (PDB ID code:2ZUQ) as a search model. The structure of the hPF4/KKOFab complex was solved by CCP4 program Phaser (McCoy 2007) with the refined KKOFab structure and hPF4 (PDB ID code: 1RHP) structure as search models. The structure of the hPF4/RTOFab complex was solved by Phaser using the structure of 2H2 Fab fragment of immature Dengue virus (PDB ID code:4KVC) and the structure of the A chain of the hPF4 monomer (PDB ID code: 1F9Q) as search models. The final solution has 8 hPF4/RTOFab complexes, related by noncrystallographic symmetry (NCS), in an asymmetric unit.

All models were iteratively built in COOT (Emsley 2010) and refined by REFMAC (Murshudov 1997; Murshudov 2011) or PHENIX (Afonine 2012). Refinement of the hPF4/KKOFab complex at low resolution was performed using deformable elastic network (DEN)-assisted refinement (Schroder 2010), REFMAC and OPUS-XREF (Lu 2006). To assist model building, the low resolution electron density maps for the hPF4/KKOFab complex were optimized using Bfactor sharpening. The anomalous diffraction data collected at long wavelength were used to assist model building and refinement of the hPF4/fondaparinux and hPF4/RTOFab complexes. The quality of refined models was checked by program PROCHECK (Laskowski 1993) and MOLPOBITY (Chen 2010). All structural figures were prepared in PyMol (The PyMOL Molecular Graphics System, Schrödinger, LLC., available on the world wide web at pymol.org). The electrostatics potentials were calculated by program APBS, an adaptive Poisson-Boltzmann solver (Baker 2001; M 2006). Data collection and refinement statistics are listed in Table 1.

Acknowledgement

We thank scientists at National Synchrotron Light Source X4A, X4C and X6A at the Brookhaven National Laboratory for their assistance in data collection. We thank Drs. Bruce S. Sachais, Ann H. Rux, Rustem I. Litvinov and John W. Weisel for advice and discussions. This work was supported in part by NIH grant P01HL110860 (DBC).

Accession Numbers

Atomic coordinates and structure factor files have been deposited in the Protein Data Bank (PDB) under the accession codes 4R9W for hPF4/pentasaccharide complex, 4R97 for KKOFab, 4R9Y for hPF4/KKOFab complex, 4RAU for hPF4/RTOFab complex.

References

Afonine, P. V., Grosse-Kunstleve, R. W., Echols, N., Headd, J. J., Moriarty, N. W., Mustyakimov, M., Terwilliger, T. C., Urzhumtsev, A., Zwart, P. H., and Adams, P. D. (2012). Towards automated crystallographic structure refinement with phenix.refine. Acta Crystallogr D Biol Crystallogr 68, 352-367.

Amiral, J., et al. Antibodies to macromolecular platelet factor 4-heparin complexes in heparin-induced thrombocytopenia: a study of 44 cases. Thromb Haemost 73, 21-28 (1995).

Arepally, G. M., Kamei, S., Park, K. S., Kamei, K., Li, Z. Q., Liu, W., Siegel, D. L., Kisiel, W., Cines, D. B., and Poncz, M. (2000). Characterization of a murine monoclonal antibody that mimics heparin-induced thrombocytopenia antibodies. Blood 95, 1533-1540.

Baker, N. A., Sept, D., Joseph, S., Holst, M. J., and McCammon, J. A. (2001). Electrostatics of nanosystems: application to microtubules and the ribosome. Proc Natl Acad Sci USA 98, 10037-10041.

Bauer, K. A., Eriksson, B. I., Lassen, M. R., and Turpie, A. G. (2001). Fondaparinux compared with enoxaparin for the prevention of venous thromboembolism after elective major knee surgery. N Engl J Med 345, 1305-1310.

Bhatt, V. R., Aryal, M. R., Shrestha, R., and Armitage, J. O. (2013). Fondaparinux-associated heparin-induced thrombocytopenia. Eur J Haematol 91, 437-441.

Block, S., Greinacher, A., Helm, C. A. & Delcea, M. Characterization of bonds formed between platelet factor 4 and negatively charged drugs using single molecule force spectroscopy. Soft Matter 10, 2775-2784 (2014).

Brandt, S., Krauel, K., Gottschalk, K. E., Renné, T., Helm, C. A., Greinacher, A., and Block, S. (2014). Characterisation of the conformational changes in platelet factor 4 induced by polyanions: towards in vitro prediction of antigenicity. Thromb Haemost 112, 53-64.

Burch, M., and Cooper, B. (2012). Fondaparinux-associated heparin-induced thrombocytopenia. Proc (Bayl Univ Med Cent) 25, 13-15.

Chen, V. B., 3rd, W. B. A., Headd, J. J., Keedy, D. A., Immormino, R. M., Kapral, G. J., Murray, L. W., Richardson, J. S., and Richardson, D. C. (2010). MolProbity: all-atom structure validation for macromolecular crystallography. Acta Crystallogr D Biol Crystallogr 66, 12-21.

Cowan, S. W., Bakshi, E. N., Machin, K. J., and Isaacs, N. W. (1986). Binding of heparin to human platelet factor 4. Biochem J 234, 485-488.

Cuker, A., and Cines, D. B. (2012). How I treat heparin-induced thrombocytopenia. Blood 119, 2209-2218.

Cuker, A., Rux, A. H., Hinds, J. L., Dela, C. M., Yarovoi, S. V., Brown, I. A., Yang, W., Konkle, B. A., Arepally, G. M., Watson, S. P., et al. (2013). Novel diagnostic assays for heparin-induced thrombocytopenia. Blood 121, 3727-3732.

Eke, Sankar, Heparin-Induced Thrombocytopenia, Medscape, ed. Emmanuel Besa, 2014, available at emedicine.medscape.com/article/1357846-overview Emsley, P., Lohkamp, B., Scott, W. G., and Cowtan, K. (2010). Features and development of Coot. Acta Crystallogr D Biol Crystallogr 66, 486-501.

Falati, S., Gross, P., Merrill-Skoloff, G., Furie, B. C. & Furie, B. Real-time in vivo imaging of platelets, tissue factor and fibrin during arterial thrombus formation in the mouse. Nat Med 8, 1175-1181 (2002).

Funatsu, H et al. Stimulation and inhibition of angiogenesis in diabetic retinopathy. Jpn J Ophthalmol. 2001 November-December; 45(6):577-84.

Greinacher, A., Alban, S., Dummel, V., Franz, G. & Mueller-Eckhardt, C. Characterization of the structural requirements for a carbohydrate based anticoagulant with a reduced risk of inducing the immunological type of heparin-associated thrombocytopenia. Thromb Haemost 74, 886-892 (1995).

Greinacher, A., Gopinadhan, M., Gunther, J. U., Omer-Adam, M. A., Strobel, U., Warkentin, T. E., Papastavrou, G., Weitschies, W., and Helm, C. A. (2006). Close approximation of two platelet factor 4 tetramers by charge neutralization forms the antigens recognized by HIT antibodies. Arterioscler Thromb Vasc Biol 26, 2386-2393.

Kang, M., Alahmadi, M., Sawh, S., Kovacs, M. J. & Lazo-Langner, A. Fondaparinux for the treatment of suspected heparin-induced thrombocytopenia: a propensity score-matched study. Blood 125, 924-929 (2015).

Kreimann, M., et al. Binding of anti-platelet factor 4/heparin antibodies depends on the thermodynamics of conformational changes in platelet factor 4. Blood 124, 2442-2449 (2014).

Laskowski, R. A., MacArthur, M. W., Moss, D. S., and Thornton, J. M. (1993). PROCHECK: a program to check the stereochemical quality of protein structures. J Appl Cryst 26, 283-291.

Lee, G. M., and Arepally, G. M. (2013). Heparin-induced thrombocytopenia. Hematology Am Soc Hematol Educ Program 2103, 668-674.

Lewis, B. E., Wallis, D. E., Leya, F., Hursting, M. J., Kelton, J. G., and Investigators, A.-. (2003). Argatroban anticoagulation in patients with heparin-induced thrombocytopenia. Arch Intern Med 163, 1849-1856.

Li, Z. Q., et al. Defining a second epitope for heparin-induced thrombocytopenia/thrombosis antibodies using KKO, a murine HIT-like monoclonal antibody. Blood 99, 1230-1236 (2002).

Linkins, L. A., Dans, A. L., Moores, L. K., Bona, R., Davidson, B. L., Schulman, S., Crowther, M., and Physicians, A.C.o.C. (2012). Treatment and prevention of heparin-induced thrombocytopenia: Antithrombotic Therapy and Prevention of Thrombosis, 9th ed: American College of Chest Physicians Evidence-Based Clinical Practice Guidelines. Chest 141, e495S-530S.

Lippi, G et al. Recombinant platelet factor 4: a therapeutic, anti-neoplastic chimera? Semin Thromb Hemost. 2010 July; 36(5):558-69. doi: 10.1055/s-0030-1255450. Epub 2010 Jul. 14.

Lu, M., Poon, B., and Ma, J. (2006). A New Method for Coarse-Grained Elastic Normal-Mode Analysis. J Chem Theory Comput 2, 464-471.

M, S., M R, S., S, W., M, P., D, C., and D, E. (2006). Toward the structural genomics of complexes: crystal structure of a PE/PPE protein complex from *Mycobacterium tuberculosis*. Proc Natl Acad Sci USA 103, 8060-8065.

Maione, T E et al., Inhibition Of Angiogenesis By Recombinant Human Platelet Factor-4 And Related Peptides. Science 5 Jan. 1990: Vol. 247 no. 4938 pp. 77-79DOI: 10.1126/science.1688470

Mayo, K. H., and Chen, M. J. (1989). Human platelet factor 4 monomer-dimertetramer equilibria investigated by 1H NMR spectroscopy. Biochemistry 28, 9469-9478.

Mayo, K. H., Ilyina, E., Roongta, V., Dundas, M., Joseph, J., Lai, C. K., Maione, T., and Daly, T. J. (1995a). Heparin binding to platelet factor-4. An NMR and sitedirected mutagenesis study: arginine residues are crucial for binding. Biochem J 312, 357-365.

Mayo, K. H., Roongta, V., Ilyina, E., Milius, R., Barker, S., Quinlan, C., Rosa, G. L., and Daly, T. J. (1995b). NMR solution structure of the 32-kDa platelet factor 4 ELR-motif N-terminal chimera: a symmetric tetramer. Biochemistry 34, 11399-11409.

McCoy, A. J., Grosse-Kunstleve, R. W., Adams, P. D., Winn, M. D., Storoni, L. C., and Read, R. J. (2007). Phaser crystallographic software. J Appl Crystallogr 40, 658-674.

Murshudov, G. N., Skubik, P., Lebedev, A. A., Pannu, N. S., Steiner, R. A., Nicholls, R. A., Winn, M. D., Long, F., and Vagin, A. A. (2011). REFMAC5 for the refinement of macromolecular crystal structures. Acta Crystallogr D Biol Crystallogr 67, 355-367.

Murshudov, G. N., Vagin, A. A., and Dodson, E. J. (1997). Refinement of macromolecular structures by the maximum-likelihood method. Acta Crystallogr D Biol Crystallogr 53, 240-255.

Nesmelova, I. V., Sham, Y., Gao, J., and Mayo, K. H. (2008). CXC and CC chemokines form mixed heterodimers: association free energies from molecular dynamics simulations and experimental correlations. J Biol Chem 283, 24155-24166.

Nguyen, T. H., Greinacher, A. & Delcea, M. Quantitative description of thermodynamic and kinetic properties of the platelet factor 4/heparin bonds. Nanoscale 7, 10130-10139 (2015).

Otwinowski, Z., and Minor, W. (1997). Processing of X-ray Diffraction Data Collected in Oscillation Mode. Methods in Enzymology 276, 307-326.

Phillips, K. W., Dobesh, P. P., and Haines, S. T. (2008). Considerations in using anticoagulant therapy in special patient populations. Am J Health Syst Pharm 65, 513-21.

R. H. Heparin is not required for detection of antibodies associated with heparin-induced thrombocytopenia/ thrombosis. J Lab Clin Med 138, 22-31 (2001).

Rauova, L., et al. Role of platelet surface PF4 antigenic complexes in heparin-induced thrombocytopenia pathogenesis: diagnostic and therapeutic implications. Blood 107, 2346-2353 (2006).

Rauova, L., Hirsch, J. D., Greene, T. K., Zhai, L., Hayes, V. M., Kowalska, M. A., Cines, D. B., and Poncz, M. (2010). Monocyte-bound PF4 in the pathogenesis of heparin-induced thrombocytopenia. Blood 116, 5021-5031.

Rauova, L., Poncz, M., McKenzie, S. E., Reilly, M. P., Arepally, G., Weisel, J. W., Nagaswami, C., Cines, D. B., and Sachais, B. S. (2005). Ultralarge complexes of PF4 and heparin are central to the pathogenesis of heparin-induced thrombocytopenia. Blood 105, 131-138.

Reilly, M. P., Taylor, S. M., Hartman, N. K., Arepally, G. M., Sachais, B. S., Cines, D. B., Poncz, M., and McKenzie, S. E. (2001). Heparin-induced thrombocytopenia/thrombosis in a transgenic mouse model requires human platelet factor 4 and platelet activation through FcgammaRIIA. Blood 98, 2442-2447.

Rota, E., Bazzan, M., and Fantino, G. (2008). Fondaparinux-related thrombocytopenia in a previous low-molecular-weight heparin (LMWH)-induced heparin-induced thrombocytopenia (HIT). Thromb Haemost 99, 779-781.

Sachais, B. S., Litvinov, R. I., Yarovoi, S. V., Rauova, L., Hinds, J. L., Rux, A. H., Arepally, G. M., Poncz, M., Cuker, A., Weisel, J. W., et al. (2012a). Dynamic antibody-binding properties in the pathogenesis of HIT. Blood 120, 1137-1142.

Sachais, B. S., Rux, A. H., Cines, D. B., Yarovoi, S. V., Garner, L. I., Watson, S. P., Hinds, J. L., and Rux, J. J. (2012b). Rational design and characterization of platelet factor 4 antagonists for the study of heparin-induced thrombocytopenia. Blood 119, 5955-5962.

Schrader, G. F., Levitt, M., and Brunger, A. T. (2010). Super-resolution biomolecular crystallography with low-resolution data. Nature 464, 1218-1222.

Stuckey, J. A., Charles, R. S., and Edwards, B. F. (1992). A model of the platelet factor 4 complex with heparin. Proteins 14, 277-287.

Turpie, A. G., Bauer, K. A., Eriksson, B. I., Lassen, M. R., and Committee., P. S. S. (2002). Postoperative fondaparinux versus postoperative enoxaparin for prevention of venous thromboembolism after elective hip-replacement surgery: a randomised double-blind trial. Lancet 359, 1721-1726.

Vagin, A., and Teplyakov, A. (2010). Molecular replacement with MOLREP. Acta Crystallogr D Biol Crystallogr 66.

Visentin, G. P., Moghaddam, M., Beery, S. E., McFarland, J. G. & Aster, Warkentin, T. E., and Lim, W. (2008). Can heparin-induced thrombocytopenia be associated with fondaparinux use? Reply to a rebuttal. J Thromb Haemost 6, 1243-1246.

Warkentin, T. E., Cook, R. J., Marder, V. J., Sheppard, J. A., Moore, J. C., Eriksson, B. I., Greinacher, A., and Kelton, J. G. (2005). Anti-platelet factor 4/heparin antibodies in orthopedic surgery patients receiving antithrombotic prophylaxis with fondaparinux or enoxaparin. Blood 106, 3791-3796.

Warkentin, T. E., Maurer, B. T., and Aster, R. H. (2007). Heparin-induced thrombocytopenia associated with fondaparinux. N Engl J Med 356, 2653-2655.

Winn, M. D., Ballard, C. C., Cowtan, K. D., Dodson, E. J., Emsley, P., Evans, P. R., Keegan, R. M., Krissinel, E. B., Leslie, A. G., McCoy, A., et al. (2011). Overview of the CCP4 suite and current developments. Acta Crystallogr D Biol Crystallogr 67, 235-242.

Zhang, X., Chen, L., Bancroft, D. P., Lai, C. K., and Maione, T. E. (1994). Crystal structure of recombinant human platelet factor 4. Biochemistry 33, 8361-8366.

Ziporen, L., et al. Defining an antigenic epitope on platelet factor 4 associated with heparin-induced thrombocytopenia. Blood 92, 3250-3259 (1998).

Discussion

Heparin-induced thrombocytopenia (HIT) is thrombotic disorder caused by immune complexes containing antibodies to an antigen composed of platelet factor 4 (PF4) and heparin or cellular glycosaminoglycans (GAGS). The structure of these immune complexes and how their composition might contribute to the difference between pathogenic and non-pathogenic anti-PF4 antibodies are unknown. To address these questions, the inventors solved the crystal structures of human recombinant PF4 in complex with Fabs derived from KKO (a murine monoclonal HIT-like antibody that competes with pathogenic human HIT antibodies) and RTO (an isotype-matched non-HIT anti-PF4 antibody) combined with the crystal structure of PF4 complexed with the heparin-mimic pentasaccharide fondaparinux as a model sugar. The PF4 tetramer is asymmetric and is capable of accommodating only two fondaparinux molecules. Fondaparinux binds between monomers A, B and C or between monomers A, C, and D, which stabilizes the AB/CD and AC/BD associations and the resultant tetramer. KKO-Fab binds to the PF4 tetramer by making contacts with now identified residues within each of three PF4 monomers, indicating that tetramerization of PF4 is a critical initiating step in antigen formation. Mutations in the putative KKO epitopes in PF4 abolished antibody binding. Unexpectedly, RTO-Fab binds to the PF4 monomer between the AB dimer interface. Importantly, the amino acid sequence recognized by RTO and KKO show considerable overlap. However, the epitope for RTO is obscured upon tetramer formation, in direct contrast to binding of KKO, which requires tetramer formation to bind. Binding of RTO to the PF4 monomer prevents formation of AB dimers and subsequent tetramerization. In support of these findings, preincubation of PF4 with RTO inhibits KKO induced platelet activation and platelet aggregation in vitro. Without wishing to be bound by any scientific theory, based on the analyses of crystal lattices, the present disclosure proposes a new model of the heparin/PF4 complex, in which PF4 tetramers cluster around a semi-rigid linear heparin subunit. Clustering of PF4 on heparin might be required for apposition of sufficient HIT antibodies to induce persistent activation of cellular FcγIIA receptors. Heparin and pathogenic HIT antibodies collaborate to stabilize the ternary immune complex, which leads to the disappearance of binding sites for at least some non-pathogenic HIT antibodies. The balance between anti-monomer and anti-tetramer PF4 antibodies may help determine the probability of clinical disease. This model also helps to explain why RTO-like anti-PF4 antibodies are found so commonly in asymptomatic patients exposed to heparin and why fondaparinux may be antigenic but rarely causes HIT, whereas longer heparin fragments and GAGS extend and render the holo-complex more stable and thereby foster the formation of pathogenic immune complexes. In summary, without wishing to be bound by any scientific theory, these crystallographic studies lead to a new model to explain the formation of pathogenic immune complexes that lead to HIT. The inhibitory effect of the anti-PF4 antibody RTO provides a structural basis for the development of new diagnostics and non-anticoagulant therapeutics.

PF4 monomers can associate into a tetrameric form as well as dissociate from that tetrameric species. The PF4 tetramer that interacts with heparin a highly sulfated glycosaminoglycan, or oligonucleotides facilitate the expression of an antigenic epitope that can bind antibodies to form a larger complex.

The ability of monomeric PF4 to form stable tetramers can be affected by deletion or amino acid substitutions. In addition while monomeric mutants may still bind heparin, they are not able to form canonical clusters with heparin as wildtype pf4 does.

PF4 which has been altered and can no longer form stable tetramers cannot form antigenic complexes when exposed to heparin, and will not be able to express the complete antigenic epitope that binds pathogenic antibodies.

Example 1 hereinabove describe and compare the crystal structures of PF4 with Fabs derived from KKO and RTO and the structure of a heparin-mimic pentasaccharide in complex with human PF4. Without wishing to be bound by any scientific theory, these structural studies reveal that the tetramerization of the antigen PF4 induced by heparin is a critical initiating step in the pathogenesis of HIT. KKO recognizes tetrameric PF4 and stabilizes the pathogenic ternary complex with heparin. Surprisingly, the non-HIT antibody RTO binds to an epitope that overlaps with the KKO epitope on the surface of PF4, prevents PF4 from being tetramerized, and inhibits KKO induced platelet activation in vitro and thrombocytopenia in vivo.

The information presented herein indicates a potential alternative approach to diagnosing and treating HIT. Example 1 described hereinabove provides the first crystal structures of PF4 in a complex with a specific part RTO or KKO (the fragment antigen binding region). These structures give novel insight into how each antibody interacts with PF4, and this knowledge indicates a new approach for diagnosing and treating HIT. For example, the present invention provides methods and compositions for the treatment of HIT based on the non-pathogenic antibody, which blocks the action of the pathogenic antibody and limits the development of HIT. The present invention also provides risk assessment and diagnostic tests for HIT.

The knowledge of KKO and RTO presented herein is useful in generating antibody assays to diagnose and/or monitor the progression of HIT as described herein. Furthermore, insight into the non-pathogenic RTO antibody (specifically, how it prevents KKO-induced HIT) is useful for generating antibody-based therapies for HIT.

EXEMPLARY EMBODIMENTS

The present invention provides a humanized antibody or antibody fragment comprising (a) a humanized light chain comprising 1) Complementarity Determining Region (CDR)-L, the sequence of which is identical to the sequence of SEQ ID NO:3; 2) CDR-L2, the sequence of which is identical to the sequence of SEQ ID NO: 4; and 3) CDR-L3, the sequence of which is identical to the sequence of SEQ ID NO: 5, and (b) a humanized heavy chain comprising 1) CDR-H1, the sequence of which is identical to the sequence of SEQ ID NO: 6; 2) CDR-H2, the sequence of which is identical to the sequence of SEQ ID NO: 7; and 3) CDR-H3, the sequence of which is identical to the sequence of SEQ ID NO: 8, as well as methods for treating, diagnosing, and monitoring the progression of HIT. The present invention also provides methods for assessing the antigenicity and ability to cause HIT of anionic anticoagulants. The present invention also provides a mutant protein which has the same amino acid sequence of a wild type PF4 monomer except that (i) at least one amino acid of the wild type PF4 monomer has been deleted, (ii) at least one amino acid of the wild type PF4 monomer has been replaced by another amino acid, or (iii) a combination of such changes has been made. The present invention also provides methods of treating or reducing the likelihood of HIT, treating angiogenesis, treating abnormal cellgrowth, or affecting coagulation pathologies that lead to thrombus formation, by administering such mutant proteins to a patient.

What is claimed is:

1. A mutant platelet factor 4 (PF4) monomer comprising amino acids 9 to 70 of SEQ ID NO: 11 and having a Q9S substitution relative to the amino acid sequence of SEQ ID NO: 11.

2. The mutant PF4 monomer of claim 1, further comprising a L11V substitution relative to the amino acid sequence of SEQ ID NO: 11.

3. The mutant PF4 monomer of claim 1, further comprising a K50E substitution relative to SEQ ID NO: 11.

4. The mutant PF4 monomer of claim 1, further comprising a L55R substitution relative to the amino acid sequence of SEQ ID NO: 11.

5. The mutant PF4 monomer of claim 1, further comprising a L11V substitution and a L55R substitution relative to the amino acid sequence of SEQ ID NO: 11.

* * * * *

UNITED STATES PATENT AND TRADEMARK OFFICE
CERTIFICATE OF CORRECTION

| | |
|---|---|
| PATENT NO. | : 12,282,028 B2 |
| APPLICATION NO. | : 18/420177 |
| DATED | : April 22, 2025 |
| INVENTOR(S) | : Mark I. Greene et al. |

It is certified that error appears in the above-identified patent and that said Letters Patent is hereby corrected as shown below:

On the Title Page

In item (56) Other Publications,

Under Column no. 2, Line no. 3, Replace:
""Monocytebound"
With:
--"Monocyte-bound--

Under Column no. 1, Page 2, Line no. 16, Replace:
"Superresolution"
With:
--Super-resolution--

Under Column no. 1, Page 2, Line no. 28, Replace:
"UnitProt"
With:
--UniProt--

Under Column no. 1, Page 2, Line no. 37, Replace:
"Enoxaparina","
With:
--Enoxaparin",--

Under Column no. 1, Page 2, Line no. 42, Replace:
""Heparininduced"
With:
--"Heparin-induced--

Signed and Sealed this
Second Day of September, 2025

Coke Morgan Stewart
*Acting Director of the United States Patent and Trademark Office*

CERTIFICATE OF CORRECTION (continued)
U.S. Pat. No. 12,282,028 B2

Under Column no. 1, Page 2, Line no. 53, Replace:
"Factor4","
With:
--Factor 4",--

Under Column no. 2, Page 2, Line no. 32, Replace:
""HOW |"
With:
--"How I--

Under Column no. 2, Page 2, Line no. 56, Replace:
"Vase"
With:
--Vasc--

Under Column no. 1, Page 3, Line no. 17, Replace:
"Hitlike"
With:
--HIT like--

Under Column no. 2, Page 3, Line no. 7, Replace:
"Monomerdimertetramer"
With:
--Monomer-dimer-tetramer--

Under Column no. 2, Page 3, Line no. 11, Replace:
"Sitedirected"
With:
--Site-directed--

In the Specification

Under Column no. 4, Line no. 27, Replace:
"1.4a"
With:
--1.4σ--

Under Column no. 4, Line no. 40, Replace:
"asymetric"
With:
--asymmetric--

Under Column no. 4, Line no. 53, Replace:
"asymetric"
With:
--asymmetric--

Under Column no. 7, Line no. 30, Replace:
"1.5a"
With:
--1.5σ--

Under Column no. 7, Line no. 32, Replace:
"1.3a"
With:
--1.3σ--

Under Column no. 11, Line no. 23, Replace:
"is"
With:
--as--

Under Column no. 12, Line no. 12, Replace:
"extent"
With:
--extent.--

Under Column no. 19, Line no. 46, Replace:
"Fcy"
With:
"Fcγ"

Under Column no. 20, Line no. 36 (Approx.), Replace:
"3-sheet"
With:
--β-sheet--

Under Column no. 20, Line no. 64, Replace:
"(PDB:IRHP)"
With:
--(PDB:1RHP)--

Under Column no. 20, Line no. 64, Replace:
"Ca"
With:
--Cα--

Under Column nos. 21-22, Line no. 5 (Table 1), Replace:
"Crystalloaraphic"
With:
--Crystallographic--

CERTIFICATE OF CORRECTION (continued)
U.S. Pat. No. 12,282,028 B2

Under Column no. 21, Line no. 46, Replace:
"inter4 chain"
With:
--inter-chain--

Under Column no. 22, Line no. 41, Replace:
"On"
With:
--One--

Under Column no. 23, Line nos. 31-32, Replace:
"PF4/KKO_Fab"
With:
--PF4/KKO-Fab--

Under Column no. 24, Line no. 6, Replace:
"3-sheet"
With:
--β-sheet--

Under Column no. 24, Line no. 8, Replace:
"3-sheet"
With:
--β-sheet--

Under Column no. 24, Line no. 50, Replace:
"3-sheet"
With:
--β-sheet--

Under Column no. 24, Line no. 55, Replace:
"3-sheet"
With:
--β-sheet--

Under Column no. 25, Line nos. 62-63, Replace:
"monomer-dimertetramer"
With:
--monomer-dimer-tetramer--

Under Column no. 28, Line nos. 15-16, Replace:
"pheresate"
With:
--pheresis--

CERTIFICATE OF CORRECTION (continued)
U.S. Pat. No. 12,282,028 B2

Under Column no. 28, Line no. 27, Replace:
"g/ml"
With:
--20 µg/ml--

Under Column no. 28, Line no. 65, Replace:
"(500 l)"
With:
--(500 µl)--

Under Column no. 30, Line no. 2, Replace:
"flashcooled"
With:
--flash-cooled--

Under Column no. 30, Line no. 6, Replace:
"pH6.8."
With:
--pH 6.8.--

Under Column no. 30, Line no. 13 (Approx.), Replace:
"flashcooled"
With:
--flash-cooled--

Under Column no. 30, Line no. 23, Replace:
"(A-2.07"
With:
--(Λ-2.07--

Under Column no. 30, Line no. 59, Replace:
"Bfactor"
With:
--B-factor--

Under Column no. 30, Line no. 63, Replace:
"MOLPOBITY"
With:
--MOLPROBITY--

Under Column no. 32, Line no. 6, Replace:
"overview"
With:
--overview.--

CERTIFICATE OF CORRECTION (continued)
U.S. Pat. No. 12,282,028 B2

Under Column no. 33, Line no. 6, Replace:
"1688470"
With:
--1688470.--

Under Column no. 33, Line no. 8, Replace:
"monomer-dimertetramer"
With:
--monomer-dimer-tetramer--

Under Column no. 33, Line no. 12, Replace:
"sitedirected"
With:
--site-directed--

Under Column no. 33, Line no. 24, Replace:
"Skubik,"
With:
--Skubàk,--

Under Column no. 33, Line no. 48, Replace:
"513-21."
With:
--S13-21.--

Under Column no. 34, Line no. 18, Replace:
"Schrader,"
With:
--Schröder,--

Under Column no. 36, Line no. 65, Replace:
"cellgrowth,"
With:
--cell-growth,--

SEQUENCE LISTING

```
Sequence total quantity: 20
SEQ ID NO: 1                moltype = AA   length = 216
FEATURE                     Location/Qualifiers
REGION                      1..216
                            note = Light Chain RTO-Fab
source                      1..216
                            mol_type = protein
                            organism = synthetic construct
SEQUENCE: 1
ELDIELTQSP KSMSMSVGER VTLTCKASEN VVTYVSWYQQ KPEQSPKLLI YGASNRYTGV   60
PDRFTGSGSA TDFTLTISSV QAEDLADYHC GQGYSYPYTF GGGTKLEIKR ADAAPTVSIF  120
PPSSEQLTSG GASVVCFLNN FYPKDINVKW KIDGSERQNG VLNSWTDQDS KDSTYSMSST  180
LTLTKDEYER HNSYTCEATH KTSTSPIVKS FNRNEC                           216

SEQ ID NO: 2                moltype = AA   length = 457
FEATURE                     Location/Qualifiers
REGION                      1..457
                            note = Heavy Chain RTO-Fab
source                      1..457
                            mol_type = protein
                            organism = synthetic construct
SEQUENCE: 2
SLEVQLVESG GGLVKPGGSL KLSCAASGFA FSRYDMSWVR QTPEKRLEWV ATITSGDNYT   60
YYPDSVKGRF TISRDNARNT LYLQMSRLRS EDTALYYCTR QGLLYYAMDY WGQGTSVNVF  120
SAKTTPPSVY PLAPGCGDTT GSSVTLGCLV KGYFPESVTV TWNSGSLSSS VHTFPALLQS  180
GLYTMSSSVT VPSSTWPSQT VTCSVAHPAS STTVDKKLEP SGPISTINPC PPCKECHKCP  240
APNLEGGPSV FIFPPNIKDV LMISLTPKVT CVVVDVSEDD PDVQISWFVN NVEVHTAQTQ  300
THREDYNSTI RVVSTLPIQH QDWMSGKEFK CKVNNKDLPS PIERTISKIK GLVRAPQVYI  360
LPPPAEQLSR KDVSLTCLVV GFNPGDISVE WTSNGHTEEN YKDTAPVLDS DGSYFIYSKL  420
NMKTSKWEKT DSFSCNVRHE GLKNYYLKKT ISRSPGK                          457

SEQ ID NO: 3                moltype = AA   length = 11
FEATURE                     Location/Qualifiers
REGION                      1..11
                            note = RTO CDR-L1
source                      1..11
                            mol_type = protein
                            organism = synthetic construct
SEQUENCE: 3
KASENVVTYV S                                                       11

SEQ ID NO: 4                moltype = AA   length = 7
FEATURE                     Location/Qualifiers
REGION                      1..7
                            note = RTO CDR-L2
source                      1..7
                            mol_type = protein
                            organism = synthetic construct
SEQUENCE: 4
GASNRYT                                                             7

SEQ ID NO: 5                moltype = AA   length = 9
FEATURE                     Location/Qualifiers
REGION                      1..9
                            note = RTO CDR-L3
source                      1..9
                            mol_type = protein
                            organism = synthetic construct
SEQUENCE: 5
GQGYSYPYT                                                           9

SEQ ID NO: 6                moltype = AA   length = 10
FEATURE                     Location/Qualifiers
REGION                      1..10
                            note = RTO CDR-H1
source                      1..10
                            mol_type = protein
                            organism = synthetic construct
SEQUENCE: 6
GFAFSRYDMS                                                         10

SEQ ID NO: 7                moltype = AA   length = 17
FEATURE                     Location/Qualifiers
REGION                      1..17
                            note = RTO CDR-H2
source                      1..17
                            mol_type = protein
                            organism = synthetic construct
```

```
SEQUENCE: 7
TITSGDNYTY YPDSVKG                                                17

SEQ ID NO: 8            moltype = AA  length = 10
FEATURE                 Location/Qualifiers
REGION                  1..10
                        note = RTO CDR-H3
source                  1..10
                        mol_type = protein
                        organism = synthetic construct
SEQUENCE: 8
QGLLYYAMDY                                                        10

SEQ ID NO: 9            moltype = AA  length = 65
FEATURE                 Location/Qualifiers
REGION                  1..65
                        note = Sequence within detailed binding interface of HIT
                         antibody KKO to a PF4 Tetramer
source                  1..65
                        mol_type = protein
                        organism = synthetic construct
SEQUENCE: 9
GDLQCLCVKT TSQVRPRHIT SLEVIKAGPH CPTAQLIATL KNGRKICLDL QAPLYKKIIK  60
KLLES                                                             65

SEQ ID NO: 10           moltype = AA  length = 65
FEATURE                 Location/Qualifiers
REGION                  1..65
                        note = Sequence within detailed binding interface of the
                         non-HIT antibody RTO to a PF4 monomer
source                  1..65
                        mol_type = protein
                        organism = synthetic construct
SEQUENCE: 10
EDGDLQCLCV KTTSQVRPRH ITSLEVIKAG PHCPTAQLIA TLKNGRKICL DLQAPLYKKI  60
IKKLL                                                             65

SEQ ID NO: 11           moltype = AA  length = 70
FEATURE                 Location/Qualifiers
source                  1..70
                        mol_type = protein
                        organism = Homo sapiens
SEQUENCE: 11
EAEEDGDLQC LCVKTTSQVR PRHITSLEVI KAGPHCPTAQ LIATLKNGRK ICLDLQAPLY  60
KKIIKKLLES                                                        70

SEQ ID NO: 12           moltype = AA  length = 71
FEATURE                 Location/Qualifiers
source                  1..71
                        mol_type = protein
                        organism = Mus musculus
SEQUENCE: 12
PEESDGDLSC VCVKTISSGI HLKHITSLEV IKAGRHCAVP QLIATLKNGR KICLDRQAPL  60
YKKVIKKILE S                                                      71

SEQ ID NO: 13           moltype = AA  length = 214
FEATURE                 Location/Qualifiers
REGION                  1..214
                        note = Humanized Light Chain (huRTO-L)
source                  1..214
                        mol_type = protein
                        organism = synthetic construct
SEQUENCE: 13
DIQMTQSPSS LSASVGDRVT ITCKASENVV TYVSWYQQKP GKAPKLLIYG ASNRYTGVPS  60
RFSGSGSGTD FTLTISSLQP EDFATYYCGQ GYSYPYTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                             214

SEQ ID NO: 14           moltype = AA  length = 220
FEATURE                 Location/Qualifiers
REGION                  1..220
                        note = Humanized Heavy Chain (huRTO-H)
source                  1..220
                        mol_type = protein
                        organism = synthetic construct
SEQUENCE: 14
EVQLVESGGG LVQPGGSLRL SCAASGFAFS RYDMSWVRQA PGKGLEWVAT ITSGDNYTYY  60
PDSVKGRFTI SRDNSKNTLY LQMNSLRAED TAVYYCTRQG LLYYAMDYWG QGTLVTVSSA  120
STKGPSVFPL APSSKSTSGG TAALGCLVKD YFPEPVTVSW NSGALTSGVH TFPAVLQSSG  180
```

```
LYSLSSVVTV PSSSLGTQTY ICNVNHKPSN TKVDKKVEPK                              220

SEQ ID NO: 15           moltype = AA  length = 70
FEATURE                 Location/Qualifiers
REGION                  1..70
                        note = M11-PF4:(9-11QCL to SCV and 55L to R) sequence
source                  1..70
                        mol_type = protein
                        organism = synthetic construct
SEQUENCE: 15
EAEEDGDLSC VCVKTTSQVR PRHITSLEVI KAGPHCPTAQ LIATLKNGRK ICLDRQAPLY        60
KKIIKKLLES                                                              70

SEQ ID NO: 16           moltype = AA  length = 62
FEATURE                 Location/Qualifiers
source                  1..62
                        mol_type = protein
                        organism = Homo sapiens
SEQUENCE: 16
QCLCVKTTSQ VRPRHITSLE VIKAGPHCPT AQLIATLKNG RKICLDLQAP LYKKIIKKLL        60
ES                                                                      62

SEQ ID NO: 17           moltype = DNA  length = 39
FEATURE                 Location/Qualifiers
misc_feature            1..39
                        note = 9SCV
source                  1..39
                        mol_type = other DNA
                        organism = synthetic construct
SEQUENCE: 17
gaagaagatg gcgacctgag ctgcgtgtgt gtgaagacc                               39

SEQ ID NO: 18           moltype = DNA  length = 39
FEATURE                 Location/Qualifiers
misc_feature            1..39
                        note = 9SCV anti
source                  1..39
                        mol_type = other DNA
                        organism = synthetic construct
SEQUENCE: 18
ggtcttcaca cacgcagc tcaggtcgcc atcttcttc                                 39

SEQ ID NO: 19           moltype = DNA  length = 36
FEATURE                 Location/Qualifiers
misc_feature            1..36
                        note = 55R
source                  1..36
                        mol_type = other DNA
                        organism = synthetic construct
SEQUENCE: 19
aggaaaattt gcttggaccg ccaagctccg ctgtac                                  36

SEQ ID NO: 20           moltype = DNA  length = 36
FEATURE                 Location/Qualifiers
misc_feature            1..36
                        note = 55R-anti
source                  1..36
                        mol_type = other DNA
                        organism = synthetic construct
SEQUENCE: 20
gtacagcgga gcttggcggt ccaagcaaat tttcct                                  36
```